United States Patent [19]
Grieve et al.

[11] Patent Number: 6,060,281
[45] Date of Patent: May 9, 2000

[54] PARASITIC HELMINTH PLA2 PROTEINS AND NUCLEIC ACID MOLECULES

[75] Inventors: Robert B. Grieve, Fort Collins; Glenn R. Frank, Wellington; Nancy Wisnewski, Ft. Collins, all of Colo.

[73] Assignees: Heska Corporation; Colorado State University Research Foundation, both of Ft. Collins, Colo.

[21] Appl. No.: 08/482,304

[22] Filed: Jun. 7, 1995

Related U.S. Application Data

[63] Continuation-in-part of application No. 08/408,120, Mar. 20, 1995, Pat. No. 5,804,200, which is a continuation of application No. 08/003,257, Jan. 12, 1993, abandoned, which is a continuation-in-part of application No. 07/654,226, Feb. 12, 1991, abandoned, and a continuation-in-part of application No. 08/225,479, Apr. 8, 1994, abandoned, and a continuation-in-part of application No. 08/101,283, Aug. 3, 1993, abandoned, which is a continuation of application No. 07/654,226, and a continuation-in-part of application No. PCT/US94/00679, Jan. 12, 1994, abandoned.

[51] Int. Cl.$^7$ .................... C12N 15/30; A61K 39/002; A61K 39/00; C07K 14/44

[52] U.S. Cl. .................... 435/69.3; 435/69.1; 435/122.1; 435/342; 435/325; 435/252.3; 435/320.1; 435/69.7; 435/71.1; 536/23.1; 536/23.2; 536/23.4; 536/23.7; 424/265.1; 424/184.1; 424/185.1; 424/94.64; 424/269.1; 424/191.1; 424/130.1; 424/151.1; 424/94.1; 530/300; 530/330; 530/350

[58] Field of Search .................... 536/73.1, 23.1, 536/23.2, 23.4, 23.7; 435/69.3, 69.1, 71.1, 172.1, 342, 325, 252.3, 320.1, 69.7; 514/44; 424/94.1, 265.1, 184.1, 185.1, 94.64, 269.1, 191.1, 130.1, 151.1; 530/300, 350, 330

[56] References Cited

U.S. PATENT DOCUMENTS

| | | |
|---|---|---|
| 4,842,999 | 6/1989 | Fuller et al. . |
| 5,021,342 | 6/1991 | Greene et al. . |
| 5,804,200 | 9/1998 | Grieve et al. . |

FOREIGN PATENT DOCUMENTS

| | | |
|---|---|---|
| 8776729 | 2/1988 | Australia . |
| 9003433 | 4/1990 | WIPO . |

OTHER PUBLICATIONS

Burgess etal. J. Cell. Biol (1990) vol. III (Nov.) 2129–2138.
Rogers etal. Infection & Immunity (1990) vol. 59 (4), 1442–1447.
Lucknow etal. Bio/Technology (1988) vol. 6, 47–55.
Draz–Sanches et al. Immunology (1991) vol. 72, 297–303.
Lazar et al. Molecular and Cell. Biolo. (1988) vol. 8 (3), 1247–1252.
Abraham, et al., "Passive Transfer of Protective Immunity to Larval Dirofilaria Immitis from Dogs to Balb/C Mice", pp. 254–257, 1991, *J. Parasitol.*, vol. 77(2).
Abraham, et al., "Genetic Control of Murine Immune Responses to Larval Dirofilaria Immitis", pp. 523–528, 1990, *J. Parasitol.*, vol. 76(4).
Abraham, et al., "Dirofilaria Immitis: Molting Process of Third–Stage Larvae", pp. 314–322, 1990, *Exp. Parasitol.*, vol. 70.
Abraham, et al., "Active and Passive Immunization of Mice Against Larval Dirofilaria Immitis", pp. 275–282, 1988, *J. Parasitol.*, vol. 74(2).
Amiri, et al., "The Schistosomatium Douthitti Cerarial Elastase is Biochemically and Structurally Distinct from that of Schistosoma Mansoni," pp. 113–120, 1988, *Mol. Biochem. Parasitol.*, vol. 28.
Awobuluyi, et al., "Immunureactivity of Cloned Dirofilaria Immitis Proteins in Dogs Following Vaccnation with Irradiated Infective Larvae," p. 139, 1989, 38th Annual Meeting, *Am. J. Trop. Med. Hyg.*, Abstract #150, Dec.
Bianco, et al., "Developmentally Regulated Expression and Secretion of a Polymorphic Antigen by Onchocerca Infective–Stage Larvae", pp. 203–212, 1990, *Mol. Biochem. Parasitol.*, vol. 39.
Blair, et al., "Immunization of Dogs Against Dirofilaria Immitis by Means of Chemically Abbreviated Infections", 1982, *Fifth International Congress of Parasitol.*, Toronto, Canada, Aug.
Boyer, et al., "Differential Antigen Content and Isotype Recognition of O. Volvulvus Antigens from Nodules Removed from Guatemalan Children", p. 169, 1990, 39th Annual Meeting, *Am. J. Trop. Med. Hyg.*, Abstract #221, Nov.
Chomczynski, et al., "Single–Step Method of RNA Isolation by Acid Guanidinium Thiocyanate–Phenol–Chloroform Extraction", pp. 156–159, 1987, *Anal. Biochem.*, vol. 162.
Coleman, et al., "Use of Implantable Intraperitoneal Diffusion Chambers to Study Bordetella Pertussis Pathogenesis: Growth and Toxin Production in Vivo", pp. 33–39, 1986, *J. Infect. Dis.*, vol. 154(1), Jul.
Culpepper, et al., "Molecular Characterization of a Dirofilaria Immitis cDNA Encoding a Highly Immunoreactive Antigen", pp. 51–62, 1992, *Mol. Biochem. Parasitol.*, vol. 54.
Dalton, et al., "Thiol Proteases Released in Vitro by Fasciola Hepatica", pp. 161–166, 1989, *Mol. Biochem. Parisitol.*, vol. 35.

(List continued on next page.)

*Primary Examiner*—Nita Minnifield
*Assistant Examiner*—Khalid Masood
*Attorney, Agent, or Firm*—Sheridan Ross P.C.

[57] ABSTRACT

The present invention relates to parasitic helminth PLA2 proteins; to parasitic helminth PLA2 nucleic acid molecules, including those that encode such proteins; to antibodies raised against such proteins; and to compounds that inhibit parasitic helminth phospholipase A$_2$ activity. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect animals from diseases caused by parasitic helminths.

10 Claims, 13 Drawing Sheets

OTHER PUBLICATIONS

Davis, et al., "Purification and Biochemical and Immunologic Characterization of a 25KD Glycoprotein from the Surface of Dirofilaria Immitis Fourth Stage Larvae", p. 256, 1988, 37th Annual Meeting, *Am. Soc. Trop. Med. Hyg.*, Abstract #404.

Delves, et al., "Neurosecretory–Like Material in 3rd– and 4th–Stage Dirofilaria Immitis Larvae (Nematoda: Filarioidea)", pp. 99–104, 1989, *J. Parasitol.*, vol. 99.

Denham, "Vaccination Against Filarial Worms Using Radiation–Attenuated Vaccines", pp. 105–111, 1980, *Inter. J. Nucl. Med. Biol.*, vol. 7.

Frank, et al., "Metabolic Labeling of Dirofilaria Immitis Third– and Fourth–Stage Larvae and Their Excretory–Secretory Products", pp. 950–956, 1991, *J. Parasitol.*, vol. 77(6).

Gamble, et al., "Purification of a 44 Kilodalton Protease which Mediates the Ecdysis of Infective Haemonchus Contortus Larvae", pp. 49–58 (1989), *Mol. Biochem. Parasitol.*, vol. 33.

Grieve, et al., "Identification of Dirofilaria Immitis Larval Antigens with Immunoprophylactic Potential Using Sera from Immune Dogs", pp. 2511–2515, 1992, *J. Immunol.*, vol. 148(8), Apr.

Grieve, "Potential for Immunoprophylaxis Against Heartworm (Dirofilaria Immitis) Infection", pp. 187–190, 1989, *Proc. Heartworm Symp.*

Grieve, et al., "Induction of Protective Immunity in Dogs to Infection with Dirofilaria Immitis Using Chemically–Abbreviated Infections", pp. 373–379, 1988, *Am. J. Trop. Med. Hyg.*, vol. 39(4).

Grieve, et al., "Epidemiology of Canine Heartworm Infection", pp. 220–246, 1983, *Epidem. Rev.*, vol. 5.

Hewick, et al., "A Gas–Liquid Solid Phase Peptide and Protein Sequenator", pp. 7990–7997, 1981, *J. Biol. Chem.*, vol. 256(15).

Hotez, et al., "Isolation and Characterization of a Proteolytic Enzyme from the Adult Hookworm Ancylostoma Caninum", pp. 7343–7348, 1985, *J. Biol. Chem.*, vol. 260(12).

Ibrahim, et al., "Antigen Shedding from the Surface of the Infective Stage Larvae of Dirofilaria Immitis", pp. 89–97, 1989, *J. Parasitol.*, vol. 99.

Jwo, et al., "Fractionated Sera from Schistosoma Mansoni Infected Patients Confers Passive Protection in Mice", pp. 553–562, 1989, *Am. J. Trop. Med. Hyg.*, vol. 41(5).

Kassis, et al., "Antibody–Dependent Complement–Mediated Killing of Schistosomula in Intraperitoneal Diffusion Chambers in Mice", pp. 1659–1662, 1979, *J. Immunol.*, vol. 123(4), Oct.

Lackey, et al., "Extracellular Proteases Of Onchocerca", pp. 176–185, 1989, *Exp. Parasitol.*, vol. 68.

Lal, et al, "Characterization of Stage–Specific Antigens of Infective of the Filarial Parasite Brugia Malayi", pp. 2032–2038, 1988, *J. Immunol.*, vol. 140.

Maki, et al., "Demonstration of Carboxyl and Thiol Protease Activities in Adult Schistosoma Mansoni, Dirofilaria Immitis, Angiostrongylus Cantonensis and Ascaris Suum", pp. 31–37, 1986, *J. Helminthol.*, vol. 60.

McKerrow, et al., "Proteinases From Invasive Larvae Of The Trematode Parasite Schistosoma Mansoni Degrade Connective–Tissue And Basement–Membrane Macromolecules", pp. 47–51, 1985, *Biochem J.*, vol. 231.

McKerrow, et al., "Schistosoma Mansoni: Cercarial Degradation of a Radioactively Labeled Collagen Gel", pp. 249–254, 1982, *Exp. Parasitol.*, vol. 53.

McReynolds, et al., "A Large Cuticular Protein from D. Immitis that is Also an Excretory or Secretory Product," pp. 173–174, 1989, 38th Annual Meeting, *Am. J. Trop. Med. Hyg.*, Abstract #233, Dec.

McReynolds, et al., "Cloning of a Highly Repeated Protein Located in the Gut of Filarial Parasites," p. 295, 1989, 38th Annual Meeting, *Am. J. Trop. Med. Hyg.*, Abstract #445, Dec.

Mok, et al., "Solubilization of Epicuticular Antigen from Dirofilaria Immitis Third–Stage Larvae", pp. 173–182, 1988, *Mol. Biochem. Parasitol.*, vol. 31.

Noble, et al., "Phylum Nematoda", pp. 256–322, 1982 (See page 256), *Parasitol.: The Biology of Animal Parasites*, Section V.

Parab, et al., "Characterization of a Monoclonal Antibody Against Infective Larvae of Brugia Malayi", pp. 169–174, 1988, *J. Immunol.*, vol. 64.

Petralanda, et al., "Studies on a Filarial Antigen With Collagenase Activity", pp. 51–59, 1986, *Mol. Biochem. Parasitol.*, vol. 19.

Philipp, et al., "Biochemical and Immunologic Characterization of a Major Surface Antigen of Dirofilaria Immitis Infective Larvae", pp. 2621–2627, *J. Immunol.*, vol. 136(7), Apr.

Richer, et al., "Dirofilaria Immitis: Proteases Produced By Third– And Fourth–Stage Larvae", pp. 213–222, 1992, *Exp. Parasitol.*, vol. 75.

Robertson, et al., "Toxocara Canis: Proteolytic Enzymes Secreted by the Infective Larvae in Vitro", pp. 30–36, 1989, *Exp. Parasitol.*, vol. 69.

Rogers, "Enzymes in the Exsheathing Fluid of Nematodes and Their Biological Significance," pp. 495–502, 1982, *J. Parasitol.*, vol. 12(6).

Scott, et al., "Surface–Associated Antigens of Second, Third and Fourth Stage Larvae of Dirofilaria Immitis", pp. 339–353, 1990, *Acta Tropica*, vol. 47.

Sher, et al., "Passive Transfer of Acquired Resistance to Schistosoma Mansoni in Laboratory Mice", pp. 347–357, 1975, *J. Parasitol.*, vol. 70.

Sim, et al., ,"Immune Responses in Human Brugia Malayi Infections: Serum Dependent Cell–Mediated Destruction of Infective Larvae in Vitro", pp. 362–370, 1982, *Trans. Roy. Soc. Trop. Med. Hyg.*, vol. 76(3).

Strosberg, et al., "Receptor–Based Assays", pp. 30–36, 1991, *Current Opin. in Biotech.*, vol. 2.

Tamashiro, et al., "Proteolytic Cleavage Of IgG and Other Protein Substrates By Dirofilaria Immitis Microfilarial Enzymes", pp. 149–154, 1987, *J. Parasitol.*, vol. 73.

Tanner, et al., "Dipetalonema Viteae (Filarioidea): Development of the Infective Larvae in Micropore Chambers Implanted Into Normal, Infected and Immunized Jirds", pp. 173–174, 1981, *Trans. Roy. Soc. Trop. Med. Hyg.*, vol. 75(1).

Wang, et al., "Parenteral Formulations of Proteins and Peptides: Stability and Stabilizers", pp. S3–S26, 1988, *J. Parent. Sci. Tech.*, vol. 42.

Willadsen, et al., "Immunologic Control of a Parasitic Arthropod, Identification of a Protective Antigen from Boophilus Microplus", pp. 1346–1351, 1989, *J. Immunol.*, vol. 143, Aug.

Wolff, et al., "Direct Gene Transfer into Mouse Muscle In Vivo", pp. 1465–1468, 1990, *Science*, vol. 247, Mar.

Wong, et al., "Dirofilaria Immitis: Fate and Immunogenicity of Irradiated Infective Stage Larvae in Beagles", pp. 465–474, 1974, *Exp. Parasitol.*, vol. 35.

Young, et al., "Efficient Isolation of Genes by Using Antibody Probes", pp. 1194–1198. 1983, *Proc. Natl. Acad. Sci. USA*, vol. 80, Mar.

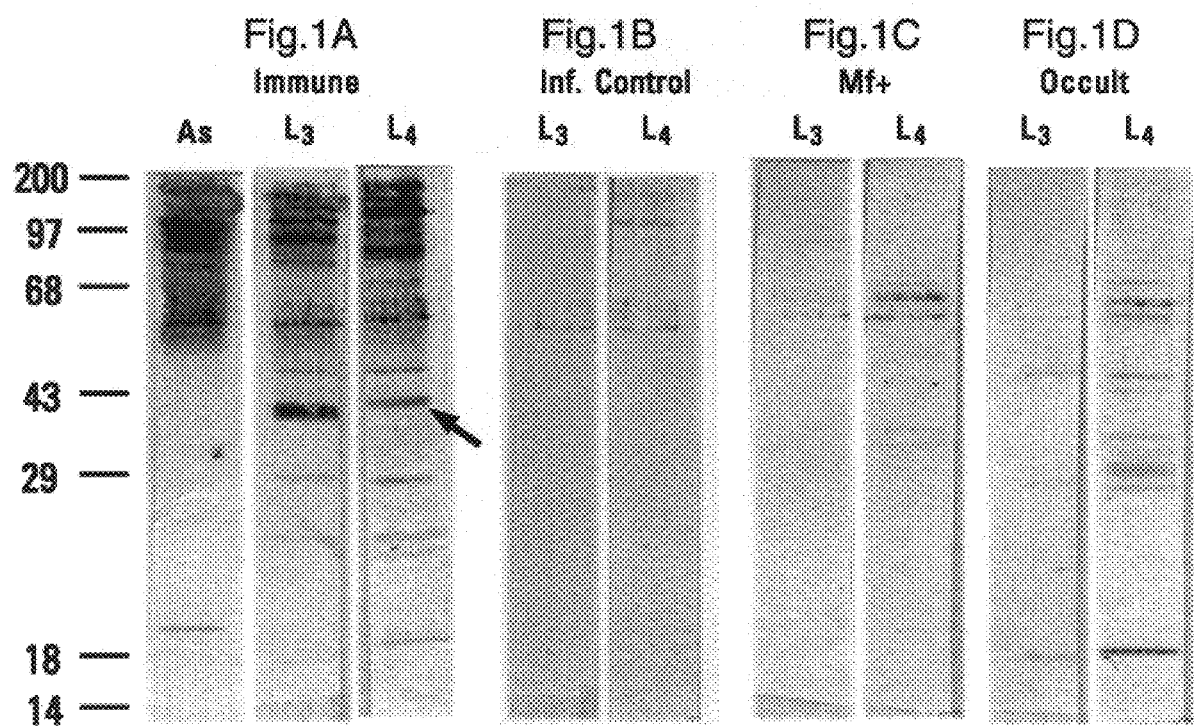

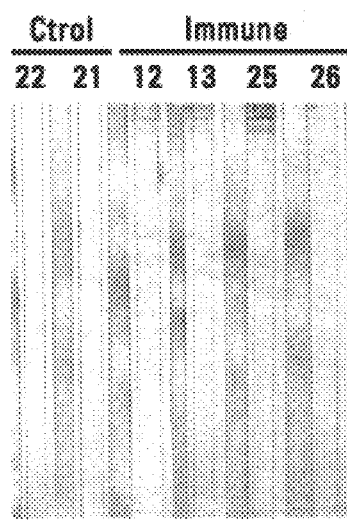
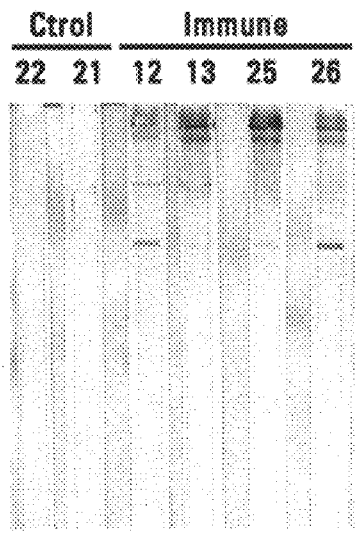
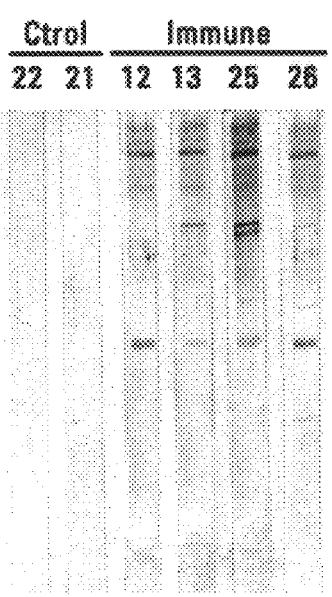
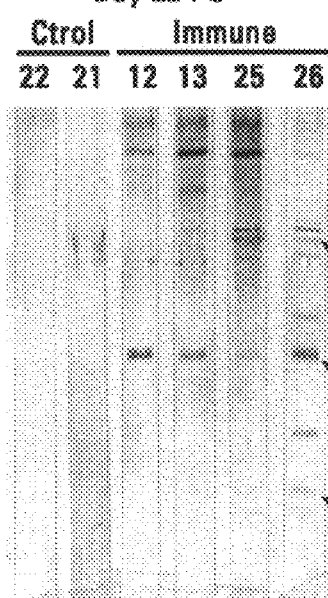
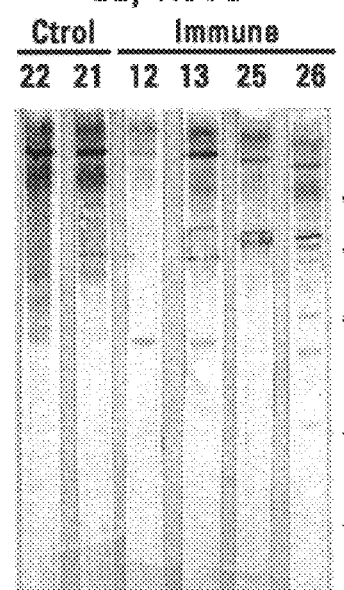

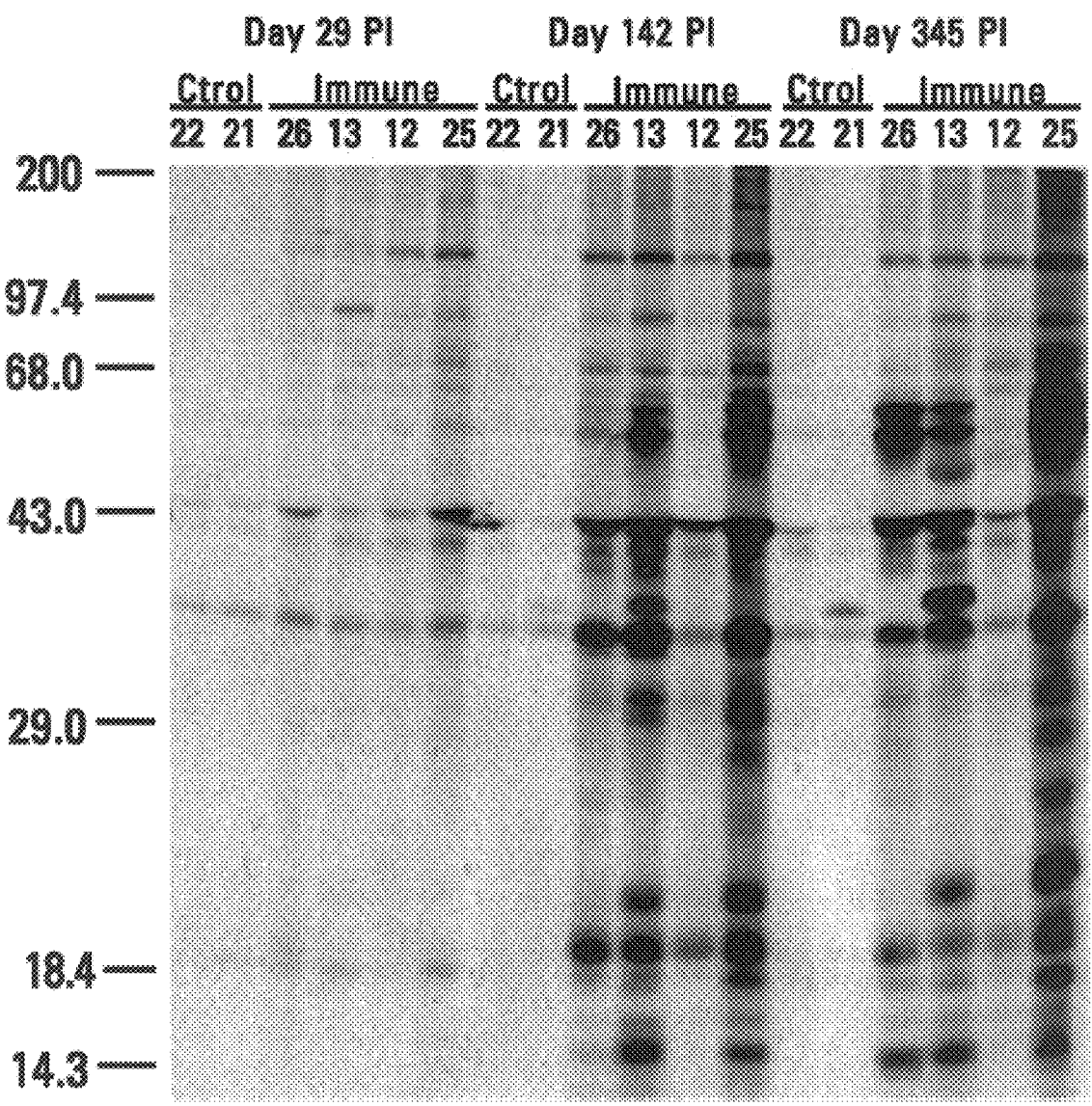

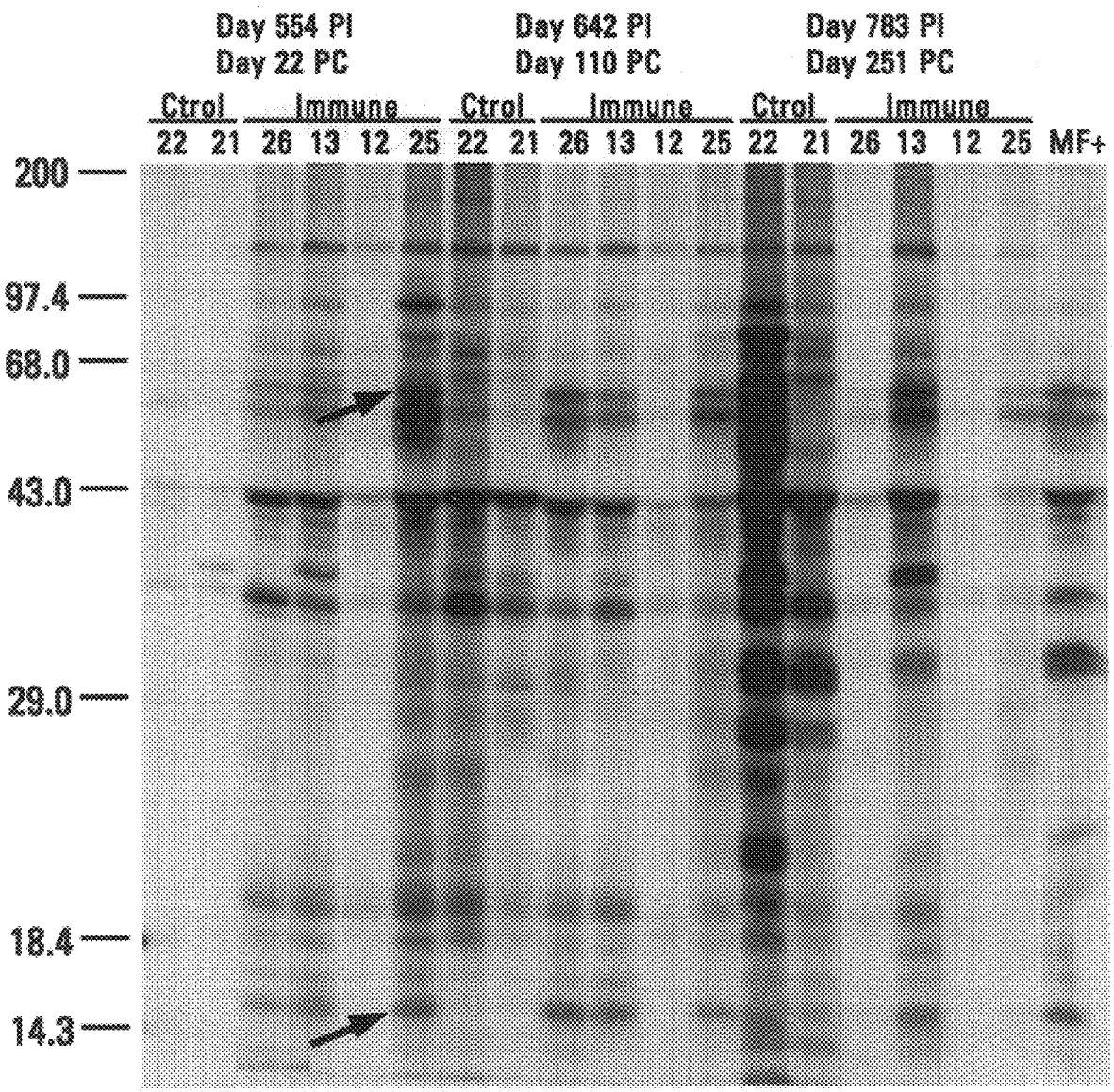

PARASITIC HELMINTH PLA2 PROTEINS AND NUCLEIC ACID MOLECULES

CROSS-REFERENCE TO RELATED APPLICATIONS

The present application is a continuation-in-part of U.S. patent application Ser. No. 08/408,120, (U.S. Pat. No. 5,804, 200) filed Mar. 20, 1995, which is a continuation of U.S. patent application Ser. No. 08/003,257, (abandoned) filed Jan. 12, 1993, which is a continuation-in-part of U.S. patent application Ser. No. 07/654,226, (abandoned) filed Feb. 12, 1991. The present application is also a continuation-in-part of U.S. patent application Ser. No. 08/225,479, (abandoned) filed Apr. 8, 1994. The present application is also a continuation-in-part of U.S. patent application Ser. No. 08/101,283, (abandoned) filed Aug. 3, 1993, which is a continuation of U.S. patent application Ser. No. 07/654,226, (abandoned) filed Feb. 12, 1991. The present application is also a continuation-in-part of PCT/US94/00679, the international filing date of which is Jan. 12, 1994. PCT/US94/00679 claims priority to U.S. patent application Ser. No. 08/408,120, (U.S. Pat. No. 5,804,200) ibid., to U.S. patent application Ser. No. 08/003,389, (abandoned) filed Jan. 12, 1993, and to U.S. patent application Ser. No. 08/109,391, (U.S. Pat. No. 5,639,896) filed Aug. 19, 1993. Each of the patent applications referred to in this section is incorporated by reference herein in its entirety.

FIELD OF THE INVENTION

The present invention relates to novel parasitic helminth phospholipase $A_2$-like (i.e., PLA2) proteins, nucleic acid molecules encoding such proteins and antibodies raised against such proteins. The present invention also includes a method to obtain such nucleic acid molecules, proteins and antibodies as well as use of such compounds to protect animals from infections caused by parasitic helminths. The present invention particularly relates to certain *Dirofilaria immitis, Onchocerca volvulus,* and *Brugia malayi* PLA2 nucleic acid molecules, proteins and antibodies as well as their use to protect animals from parasitic helminth infection.

BACKGROUND OF THE INVENTION

Parasitic helminth infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasitic helminth infections, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

It is particularly difficult to develop vaccines against parasitic helminth infections both because of the complexity of the parasite's life cycle and because, while administration of parasites or parasite antigens can lead to the production of a significant antibody response, the immune response is typically not sufficient to protect the animal against infection.

As an example of the complexity of parasitic helminths, the life cycle of *D. immitis,* the helminth that causes heartworm, includes a variety of life forms, each of which presents different targets, and challenges, for immunization. Adult forms of the parasite are quite large and preferentially inhabit the heart and pulmonary arteries of an animal. Sexually mature adults, after mating, produce microfilariae which traverse capillary beds and circulate in the vascular system of the dog. One method of demonstrating infection in the dog is to detect the circulating microfilariae.

If the dog is maintained in an insect-free environment, the life cycle of the parasite cannot progress. However, when microfilariae are ingested by the female mosquito during blood feeding on an infected dog, subsequent development of the microfilariae into larvae occurs in the mosquito. The microfilariae go through two larval stages (L1 and L2) and finally become mature third stage larvae (L3) which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilariae can be detected, but the existence of the adult heartworms can be determined through thoracic examination.

Heartworm not only is a major problem in dogs, which typically cannot even develop immunity upon infection (i.e., dogs can become reinfected even after being cured by chemotherapy), but is also becoming increasingly widespread in other companion animals, such as cats and ferrets. Heartworm infections have also been reported in humans. Other parasitic helminthic infections are also widespread, and all require better treatment, including a preventative vaccine program. *O. volvulus,* for example, causes onchocerciasis (also known as river blindness) in humans. Up to 50 million people throughout the world are reported to be infected with *O. volvulus,* with over a million being blinded due to infection. Brugia filariids can infect humans and other animals, causing diseases including filariasis (including lymphatic filariasis), elephantiasis and tropical eosinophilia.

Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. A large number of materials are immunogenic and produce sera which test positive in immunoassays for ability to react with the immunizing antigen, but which fail to protect the hosts against infection. Accordingly, the use of serum simply resulting from immunization or from infection by a parasitic helminth to screen for candidate vaccines does not provide sufficient specificity to identify protective immunogens. On the other hand, serum or other components of blood from immunized animals which is demonstrably protective against infection would contain antibodies, cells, or other factors that could selectively bind to potential antigens that, if used as therapeutic compositions, would elicit immune responses that protect against challenge. A method to use serum from immune animals to identify candidate parasitic helminth vaccines is disclosed in U.S. patent application Ser. No. 08/101,283, (abandoned) ibid., also published as PCT International Publication No. WO 92/13560, by Grieve et al., on Aug. 20, 1992.

An alternative approach to finding a suitable parasitic helminth vaccine has been to attempt to identify prominent antigens in the infective stage of the helminth. Researchers have identified several proteins in the infective stage of *D. immitis.*, including, for example, a 35-kilodalton (kD) major surface antigen of *D. immitis* third stage larvae (Philipp, et al., 1986, *J. Immunol.* 136, 2621–2627; Ibrahim, et al., 1989, *Parasitol.* 99, 89–97; Scott, et al, 1990, *Acta Tropica* 47, 339–353) as well as three major surface proteins of the L4 having molecular weights of 150 kD, 52 kD, and 25 kD (Davis, et al., 1988, Abstract 404, 37th Annual Meeting, *Am. Soc. Trop. Med. Hyg.*). Scott et al., ibid., also identified a number of other proteins on the surface of *D. immitis* having molecular weights ranging from 3 kD to 66 kD. None of these proteins has yet been shown to be an effective vaccine.

Furthermore, although several Onchocerca genes have been isolated, genes encoding antigens targeted specifically to L3 and L4 stage larvae have apparently not been reported. In particular, genes encoding antigens that selectively bind to serum obtained from a host that is immune to Onchocerca infection (e.g., *O. volvulus* infection), apparently have not been isolated, nor apparently have such antigens been characterized.

As such, there remains a need to identify an efficacious composition that protects animals against diseases caused by parasitic helminths and that, preferably, also protects animals from infection by such helminths.

SUMMARY OF THE INVENTION

The present invention relates to parasitic helminth PLA2 proteins; to parasitic helminth PLA2 nucleic acid molecules, including those that encode such proteins; to antibodies raised against such proteins (anti-parasitic helminth PLA2 antibodies), and to inhibitors of phospholipase $A_2$ activity. The present invention also includes methods to obtain such proteins, nucleic acid molecules, antibodies and inhibitors. Also included in the present invention are therapeutic compositions comprising such proteins, nucleic acid molecules, antibodies and/or inhibitors, as well as use of such therapeutic compositions to protect animals from diseases caused by parasitic helminths.

One embodiment of the present invention is an isolated parasitic helminth nucleic acid molecule that hybridizes under stringent hybridization conditions with a Dirofilaria immitis PLA2 gene, an *Onchocerca volvulus* PLA2 gene, and/or a *Brugia malayi* PLA2 gene. A *D. immitis* PLA2 gene preferably includes nucleic acid SEQ ID NO:1; an *O. volvulus* PLA2 gene preferably includes nucleic acid sequence SEQ ID NO:8; and a *B. malayi* PLA2 gene preferably includes nucleic acid sequence SEQ ID NO:15 and/or SEQ ID NO:18. A PLA2 nucleic acid molecule of the present invention can include a regulatory region of a parasitic helminth PLA2 gene and/or can encode a parasitic helminth PLA2 protein. Particularly preferred PLA2 nucleic acid molecules include nucleic acid sequence SEQ ID NO:1, nucleic acid sequence SEQ ID NO:3, nucleic acid sequence SEQ ID NO:4, nucleic acid sequence SEQ ID NO:6, nucleic acid sequence SEQ ID NO:8, nucleic acid sequence SEQ ID NO:10, nucleic acid sequence SEQ ID NO:11, nucleic acid sequence SEQ ID NO:13, nucleic acid sequence SEQ ID NO:15, nucleic acid sequence SEQ ID NO: 16, nucleic acid sequence SEQ ID NO: 18, and/or nucleic acid sequence SEQ ID NO:19, as well as allelic variants of one or more of those nucleic acid molecules.

The present invention also relates to recombinant molecules, recombinant viruses and recombinant cells that include parasitic helminth PLA2 nucleic acid molecules of the present invention. Also included are methods to produce such nucleic acid molecules, recombinant molecules, recombinant viruses and recombinant cells.

Another embodiment of the present invention includes an isolated parasitic helminth PLA2 protein, including a protein that includes a parasitic helminth PLA2 protein. A preferred parasitic helminth PLA2 protein, when administered to an animal, is capable of eliciting an immune response against a natural parasitic helminth PLA2 protein and/or of selectively binding to immune serum derived from an animal that is immune to infection by the parasitic helminth. A preferred parasitic helminth PLA2 protein is a third stage or fourth stage larval protein. In one embodiment, a preferred PLA2 protein has a molecular weight of about 22 kD or of about 20.5 kD as determined by Tris-glycine SDS PAGE. Particularly preferred PLA2 proteins are proteins that include amino acid sequence SEQ ID NO:2, amino acid sequence SEQ ID NO:5, amino acid sequence SEQ ID NO:7, amino acid sequence SEQ ID NO:9, amino acid sequence SEQ ID NO:12, amino acid sequence SEQ ID NO:14, amino acid sequence SEQ ID NO:17, and/or amino acid sequence SEQ ID NO:20, as well as proteins that are encoded by nucleic acid molecules that are allelic variants of the nucleic acid molecules that encode proteins having any of those SEQ ID NO's.

The present invention also relates to mimetopes of parasitic helminth PLA2 proteins as well as to isolated antibodies that selectively bind to parasitic helminth PLA2 proteins or mimetopes thereof. Also included are methods, including recombinant methods, to produce proteins, mimetopes and antibodies of the present invention.

Yet another embodiment of the present invention is a therapeutic composition that is capable of protecting an animal from disease caused by a parasitic helminth. Such a therapeutic composition includes one or more of the following protective compounds: an isolated parasitic helminth PLA2 protein or a mimetope thereof; an isolated parasitic helminth nucleic acid molecule that hybridizes under stringent hybridization conditions with a *Dirofilaria immitis* PLA2 gene, an *Onchocerca volvulus* PLA2 gene, and/or a *Brugia malayi* PLA2 gene; an isolated antibody that selectively binds to a parasitic helminth PLA2 protein; and an inhibitor of phospholipase $A_2$ activity identified by its ability to inhibit parasitic helminth phospholipase $A_2$ activity. A preferred therapeutic composition of the present invention also includes an excipient, an adjuvant and/or a carrier. Preferred PLA2 nucleic acid molecule compounds of the present invention include naked nucleic acid vaccines, recombinant virus vaccines and recombinant cell vaccines. Also included in the present invention is a method to protect an animal from disease caused by a parasitic helminth. The method includes the step of administering to the animal a therapeutic composition of the present invention.

Suitable parasitic helminths to use in the production (e.g., recombinant, natural, or synthetic production) of nucleic acid molecules, proteins and antibodies of the present invention include nematodes, cestodes and trematodes, with nematodes (such as filariid, ascarid, strongyle and trichostrongyle nematodes) being preferred, with filariids being more preferred, and with *D. immitis, O. volvulus,* and *B. malayi* being even more preferred.

Suitable and preferred parasitic helminths from which to protect animals are as disclosed for use in the production of nucleic acid molecules, proteins and antibodies of the present invention. As such, preferred diseases from which to protect animals include diseases caused by nematodes, cestodes and/or trematodes, with diseases caused by nematodes being more preferred targets, and with diseases caused by filariids being even more preferred targets. Particularly preferred diseases from which to protect animals include heartworm, onchocerciasis and filariasis.

Another embodiment of the present invention is a method to identify a compound capable of inhibiting phospholipase $A_2$ activity of a parasitic helminth. The method includes the steps of: (a) contacting an isolated parasitic helminth PLA2 protein with a putative inhibitory compound under conditions in which, in the absence of the compound, the protein has phospholipase $A_2$ activity; and (b) determining if the putative inhibitory compound inhibits the phospholipase $A_2$ activity. Also included in the present invention is a test kit to identify a compound capable of inhibiting phospholipase $A_2$ activity of a parasitic helminth. Such a test kit includes an isolated parasitic helminth PLA2 protein having phospholipase $A_2$ activity and a means for determining the extent of inhibition of that activity in the presence of a putative inhibitory compound.

BRIEF DESCRIPTION OF THE FIGURES

FIG. 1 shows Western blots of *D. immitis* proteins immunoreacted with canine sera derived from immune and non-immune dogs.

FIG. 2 shows Western blots of *D. immitis* proteins immunoreacted with canine sera at various time points (days) after immunization.

FIGS. 3A–B shows the results of SDS-PAGE on proteins labeled with S-35 methionine extracted from *D. immitis* L4 larvae and reacted with control and immune sera at various time points after immunization.

DETAILED DESCRIPTION OF THE INVENTION

Figure 4A:
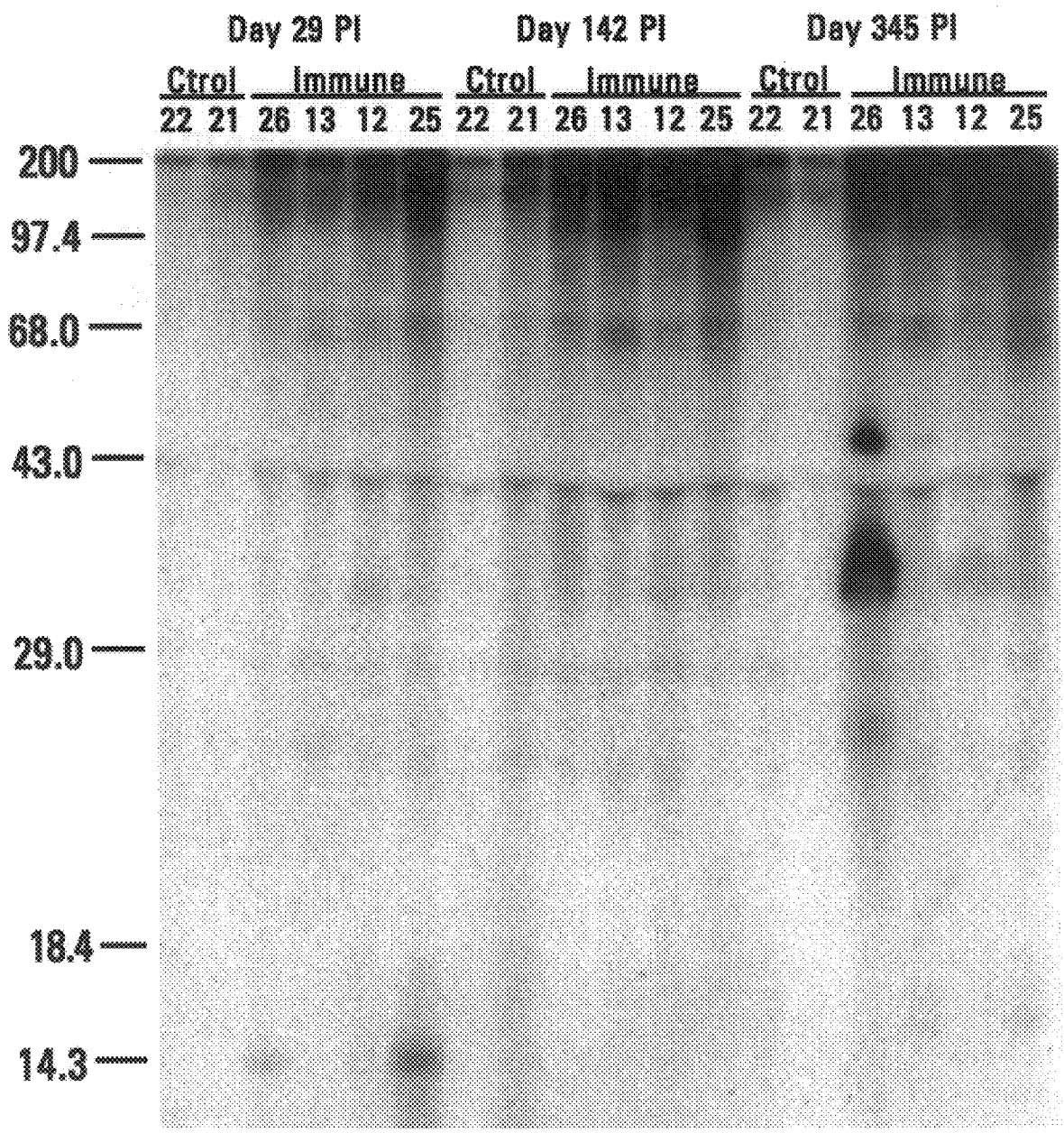
FIGS. 4A–B shows the results of proteins analyzed as set forth in FIG. 3, but wherein the larval surface proteins are labeled with I-125.

The present invention includes isolated parasitic helminth proteins that, at least in the carboxyl-terminal halves, show similarity in amino acid sequence to at least certain snake and mammalian phospholipase $A_2$ (PLA$_2$) enzymes, the similarities being particularly well conserved with respect to the cysteines and amino acids comprising the active site. As such, isolated parasitic helminth proteins of the present invention are referred to as parasitic helminth PLA2 proteins and the domain of a parasitic helminth PLA2 protein sharing at least some amino acid sequence homology (or identity) with phospholipase $A_2$ enzymes is referred to as a phospholipase $A_2$-related domain, or PLA$_2$-related domain.

The enzyme PLA$_2$ catalyzes the hydrolysis of the 2-acyl ester group of sn-3-glycerophospholipids. Potential roles of a PLA$_2$ activity in parasites include effecting lipid metabolism; membrane synthesis, remodeling and/or separation (e.g., as part of the molting process); and/or migration (e.g., PLA$_2$ could aid in disrupting host cell membranes during the tissue migration that occurs during L4). As such, the finding of similar sequences between the C-terminal half of a parasitic helminth PLA2 protein and several known snake and mammalian PLA$_2$ enzymes suggests the targeting of such sequences in the development of anti-parasite therapeutics that block PLA$_2$ activity, thereby protecting animals from parasite helminth infections. Such therapies could be particularly beneficial in disrupting molting by nematodes in general and tissue migration by those nematodes capable of such migration. That parasitic helminth PLA2 proteins have utility as therapeutic compositions is also supported by the ability of parasitic helminth PLA2 proteins of the present invention to selectively bind to serum from animals that are immune to infection by a parasitic helminth.

The present invention includes not only parasitic helminth PLA2 proteins but also parasitic helminth PLA2 nucleic acid molecules, antibodies directed against parasitic helminth PLA2 proteins and other inhibitors of PLA2 proteins. Also included is the use of these proteins, nucleic acid molecules, antibodies and other inhibitors as therapeutic compositions to protect animals from parasitic helminth diseases as well as in other applications, such as those disclosed below.

One embodiment of the present invention is an isolated parasitic helminth PLA2 protein. According to the present invention, an isolated, or biologically pure, protein, is a protein that has been removed from its natural milieu. As such, "isolated" and "biologically pure" do not necessarily reflect the extent to which the protein has been purified. An isolated PLA2 protein of the present invention can be obtained from its natural source, can be produced using recombinant DNA technology or can be produced by chemical synthesis. As used herein, an isolated parasitic helminth PLA2 protein can be a full-length protein or any homologue of such a protein. Examples of PLA2 homologues include PLA2 proteins in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue includes at least one epitope capable of eliciting an immune response against a parasitic helminth PLA2 protein. That is, when the homologue is administered to an animal as an immunogen, using techniques known to those skilled in the art, the animal will produce a humoral and/or cellular immune response against at least one epitope of a parasitic helminth PLA2 protein. PLA2 homologues can also be selected by their having a PLA$_2$-related domain and or by their ability to selectively bind to immune serum. Methods to measure such activities are disclosed herein.

Parasitic helminth PLA2 protein homologues can be the result of natural allelic variation or natural mutation. PLA2 protein homologues of the present invention can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to elicit an immune response against parasitic helminth PLA2 proteins. Examples of such identification techniques are disclosed herein.

Isolated parasitic helminth PLA2 proteins and mimetopes thereof of the present invention preferably are capable of selectively binding to serum collected from an animal that is immune to infection by the helminth, the serum being capable of inhibiting helminth development; that is, the protein is immunoreactive with at least one component in immune serum which is validated as protective in an immune host using, for example, the method disclosed in Grieve et al. in WO 92/13560, ibid. The ability of such proteins and mimetopes to selectively bind to components in such a serum is believed to suggest the ability of such proteins and mimetopes to protect an animal from parasite infection when such proteins and/or mimetopes are administered to an animal in an effective manner.

Animals that are immune to infection by parasitic helminths are animals that exhibit an immune response that is sufficient to protect the animal from such infection. Immune animals typically are animals that have been administered larval, adult and/or microfilarial helminths in a manner effective to elicit a protective response, preferably using irradiated helminths or a chemically-abbreviated infection protocol. For example, dogs receiving chemically abbreviated D. immitis larval infections exhibit significant immunity to challenge infections. Furthermore, sera obtained from such dogs are effective in passively transferring larval killing and stunting capabilities to mice. Preferred immune animals are those that have been immunized against helminth larvae, particularly against L3 and/or L4 larvae, since, in accordance with the present invention, it is particularly desirable to prevent L3 larvae introduced into an animal from developing into adult parasites. It should be noted, however, that immune animals do not preclude naturally-infected animals that generate protective antibodies.

In accordance with the present invention, a mimetope refers to any compound that is able to mimic the ability of an isolated parasitic helminth PLA2 protein of the present invention to selectively bind to anti-parasitic helminth immune serum (i.e., to bind to at least one component in immune serum that is protective against parasitic helminths) and/or to elicit an immune response against a parasitic helminth PLA2 protein of the present invention. A mimetope can be a peptide that has been modified to decrease its susceptibility to degradation but that still retains its selective binding ability. Other examples of mimetopes include, but are not limited to, anti-idiotypic antibodies or fragments thereof, that include at least one binding site that mimics one or more epitopes of an isolated protein of the present invention; non-proteinaceous immunogenic portions of an isolated protein (e.g., carbohydrate structures); and synthetic or natural organic molecules, including nucleic acids, that have a structure similar to at least one epitope of an isolated protein of the present invention. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

As used herein, the term "selectively binds to" immune serum refers to the ability of isolated proteins and mimetopes thereof to bind to serum collected from animals that are immune to parasitic helminth infection but essentially not to bind, according to standard detection techniques (such as those described in Sambrook et al., *Molecular Cloning: A Laboratory Manual,* Cold Spring Harbor Labs Press, 1989) to serum collected from animals that are not immune to parasitic helminth infection. Preferably, the isolated proteins and mimetopes are able to bind to anti-parasitic helminth immune serum with high affinity. The ability of a protein or mimetope thereof to selectively bind to anti-parasitic helminth immune serum can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy. It should be noted that the ability of an isolated protein or mimetope thereof to selectively bind to immune serum raised against a certain stage of helminth development does not preclude the isolated protein or mimetope from being able to also bind to immune serum raised against other stages of helminth development. For example, the ability of an isolated protein or mimetope thereof to selectively bind to an anti-larval immune serum does not preclude the isolated protein or mimetope from being able to also bind to anti-microfilarial and/or anti-adult immune serum.

As used herein, the phrases "capable of selectively binding to at least one component of a serum collected from an animal that is immune to infection by the helminth", "capable of selectively binding to immune serum", and "specifically immunoreactive with validated components of immune host serum or tissue" have similar meanings. "Validated components" are components which have been shown in the method of the invention, as described herein, to exert a deleterious effect on parasitic nematodes when supplied in a diffusion chamber to a host which has been administered the component. By "specifically immunoreactive" is meant that the immunogen is capable of binding the validated component as derived from an immune susceptible host, but is incapable of binding components found in nonimmune counterparts in this species. By "susceptible host" is meant a host species that is ordinarily susceptible to infestation by the nematode parasite in question. Individual members of the susceptible host species may have acquired immunity to this infestation.

One embodiment of the present invention is the use of anti-parasitic helminth immune serum to identify isolated proteins and mimetopes of the present invention, a technique referred to herein as an immune serum screening assay. Immune serum can be raised against a parasitic helminth by administering the helminth to an animal under conditions that elicit an immune response. Immune serum can be raised against larval, microfilarial, and/or adult helminths, preferably against larvae, and more preferably against L3 and/or L4 larvae. Immune sera of the present invention are capable not only of inhibiting development of the species of helminth that elicited the immune response, but also of helminth species that immunologically cross-react with the immune sera. Due to the similarity between helminths, immune sera of the present invention are capable of reacting with a large variety of helminths. Inhibiting the development of helminths includes killing, reducing the growth of, blocking the maturation of, altering the morphology of, altering the metabolism of, and/or otherwise being detrimental to the helminth.

Any animal that is capable of mounting an immune response to protect itself from helminth infection is a suitable animal to which helminths can be administered and from which immune serum can be collected. For example, a preferred animal from which to collect serum capable of inhibiting the development of D. immitis is a dog that has been administered L3 and/or L4 D. immitis larvae under conditions that elicit an immune response.

The ability of immune serum of the present invention to inhibit parasitic helminth development can be determined in a number of ways. A preferred method to monitor the ability of immune serum to inhibit the development of an infectious agent is disclosed by Grieve et al., WO 92/13560, ibid., and in the Examples. As disclosed therein, for example, the ability of an anti-parasitic helminth larval immune serum to inhibit larval development can be determined as follows. Briefly, a naive animal (i.e., an animal not previously exposed to parasitic helminth larvae) is implanted with at least one diffusion chamber containing helminth larvae, preferably L3 larvae. The animal is also administered either the anti-larval immune serum to be tested or a control non-immune serum, preferably at a site near the diffusion chambers. After a suitable period of time, for example, from about three to about four weeks for *D. immitis* larvae implanted in mice, the diffusion chambers are removed, and the effects of the immune serum on larval growth and development are determined by, for example, comparing larval growth and survival in chambers exposed to anti-larval immune serum with the growth and survival of larvae in diffusion chambers exposed to non-immune serum. A significant number of larvae exposed to anti-larval immune serum are either killed or stunted compared to larvae exposed to non-immune serum.

Grieve et al., WO 92/13560, ibid., further discloses use of the immune serum screening assay to screen for, and hence identify, desired proteins that selectively bind to the immune serum. Briefly, the immune serum can be contacted with a protein-containing composition under conditions that permit selective binding by desired proteins to components in the serum. Complexes between the proteins and serum components are recovered, the proteins are separated from the serum components and are then analyzed. Nucleic acid sequences encoding such proteins can be identified using known recombinant DNA techniques, such as those described in Sambrook et al., ibid. In another embodiment, the immune serum screening assay can be used to identify nucleic acid sequences encoding isolated proteins of the present invention by screening parasite helminth expression cDNA libraries with immune sera of the present invention to identify proteins expressed by individual clones that are capable of selectively binding to the immune sera. The immune serum screening assay can also be used to identify mimetopes capable of selectively binding to immune serum, such as to anti-L3 and/or L4 larval immune serum. Mimetopes can also be designed or improved using information derived from proteins identified by the immune serum screening assay. It should be appreciated that not only serum, but also other immunogenic components of bodily fluids collected from animals immune to helminth infection, such as cells, specific antibodies, and fragments thereof, can be used in the immune serum screening assay.

As disclosed in Grieve et al., WO 92/13560, ibid., anti-larval immune serum has been used to identify nematode *D. immitis* proteins expressed during L3 and/or L4 that have molecular weights of 66 kD, 65 kD, 59 kD, 39 kD, 33 kD, 23/24 kD, 22/20.5 kD and 14 kD, as determined by their migration patterns when subjected to Tris-glycine SDS PAGE (i.e., polyacrylamide gel electrophoresis conducted in the presence of a Tris-glycine buffer containing sodium dodecyl sulfate). It is to be noted that U.S. patent application Ser. No. 08/408,120, (U.S. Pat. No. 5,840,200) ibid. reports the isolation of three proteins in the "22/20.5" region of the gel, that are referred to therein as 22U, 22L and 20.5 kD proteins; the isolation of these proteins is described in more detail in the Examples section. Both 22L and 20.5 kD proteins are referred to herein as examples of parasitic helminth PLA2 proteins of the present invention, namely PDiPLA2$_{150}$ also referred to herein as P22L) and PDiPLA2$_{129}$ (also referred to herein as P20.5) The two proteins are related in that PDiPLA2$_{150}$ includes PDiPLA2$_{129}$ plus a putative signal peptide of about 21 amino acids. The 22U kD protein (also referred to herein as P22U) is a different protein (by, for example, both sequence and iso-electric point (pI) analysis) that co-migrated with the 22L kD protein when subjected to Tris glycine SDS PAGE as described herein; i.e., 22U refers to the upper band migrating at about 22 kD and 22L refers to the lower band migrating at about 22 kD in such a system. The 22U protein is a basic protein, whereas both PDiPLA2$_{150}$ and PDiPLA2$_{129}$ are acidic proteins; for details, see the Examples.

Parasitic helminth PLA2 proteins of the present invention, including homologues of the full-length protein, have the further characteristic of being encoded by nucleic acid molecules that hybridize under stringent hybridization conditions to at least one of the following genes: (a) a gene encoding a *Dirofilaria immitis* PLA2 protein (i.e., a *D. immitis* PLA2 gene); (b) a gene encoding an *Onchocerca volvulus* PLA2 protein (i.e., an *O. volvulus* PLA2 gene; and (c) a gene encoding a *Brugia malayi* PLA2 protein (i.e., a *B. malayi* PLA2 gene). It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., *Molecular Cloning: A Laboratory Manual,* Cold Spring Harbor Labs Press, 1989. Examples of such conditions are provided in the Examples section of the present application.

As used herein, a *D. immitis* PLA2 gene includes all nucleic acid sequences related to a natural *D. immitis* PLA2 gene such as regulatory regions that control production of the *D. immitis* PLA2 protein encoded by that gene (such as, but not limited to, transcription, translation or post-translation control regions) as well as the coding region itself. In one embodiment, a *D. immitis* PLA2 gene includes the nucleic acid sequence SEQ ID NO:1. Nucleic acid sequence SEQ ID NO:1 represents the deduced sequence of a cDNA (complementary DNA) nucleic acid molecule denoted herein as nDiPLA2$_{586}$, the production of which is disclosed in the Examples. It should be noted that since nucleic acid sequencing technology is not entirely error-free, SEQ ID NO:1 (as well as other sequences presented herein), at best, represents an apparent nucleic acid sequence of the nucleic acid molecule encoding a *D. immitis* PLA2 protein of the present invention.

In another embodiment, a *D. immitis* PLA2 gene can be an allelic variant that includes a similar but not identical sequence to SEQ ID NO:1. An allelic variant of a *D. immitis* PLA2 gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given parasitic helminth since the genome is diploid and/or among a group of two or more parasitic helminths. The extent and type of amino acid sequence heterogeneity demonstrated in the sequencing of the amino-terminus and several tryptic fragments of a population of D. immitis PLA2 proteins isolated from D. immitis larvae supports the existence of several D. immitis PLA2 allelic variants; details are provided in the Examples.

Similarly, an O. volvulus PLA2 gene includes all nucleic acid sequences related to a natural O. volvulus PLA2 gene such as regulatory regions that control production of the O. volvulus PLA2 protein encoded by that gene as well as the coding region itself. In one embodiment, an O. volvulus PLA2 gene includes the nucleic acid sequence SEQ ID NO:8. Nucleic acid sequence SEQ ID NO:8 represents the deduced sequence of a cDNA nucleic acid molecule denoted herein as nOvPLA2$_{557}$, the production of which is disclosed in the Examples. In another embodiment, an O. volvulus PLA2 gene can be an allelic variant that includes a similar but not identical sequence to SEQ ID NO:8.

Similarly, a B. malayi PLA2 gene includes all nucleic acid sequences related to a natural B. malayi PLA2 gene such as regulatory regions that control production of the B. malayi PLA2 protein encoded by that gene as well as the coding region itself. In one embodiment, a B. malayi PLA2 gene includes the nucleic acid sequence SEQ ID NO:15. Nucleic acid sequence SEQ ID NO:15 represents the deduced sequence of a B. malayi genomic library-derived nucleic acid molecule denoted herein as nBmPLA2(19)$_{242}$, the production of which is disclosed in the Examples. In another embodiment, a B. malayi PLA2 gene can be an allelic variant that includes a similar but not identical sequence to SEQ ID NO:15. An example provided herein is B. malayi nucleic acid molecule nBmPLA2(25)$_{2551}$ the deduced nucleic acid sequence of which is represented herein as SEQ ID NO:18.

The minimal size of a parasitic helminth PLA2 protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of a nucleic acid molecule such nucleic acid molecules is typically at least about 12 to about 15 nucleotides in length if the nucleic acid molecules are GC-rich and at least about 15 to about 17 bases in length if they are AT-rich.

As such, the minimal size of a nucleic acid molecule used to encode a PLA2 protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a PLA2 protein homologue of the present invention is from about 4 to about 6 amino acids in length, with preferred sizes depending on whether a full-length, fusion, multivalent, or functional portions of such proteins are desired.

Parasitic helminth proteins of the present invention, including homologues thereof, preferably are capable of eliciting an immune response against a parasitic helminth PLA2 protein and/or of selectively binding to immune serum. The minimum size of such a protein is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

One embodiment of the present invention is a parasitic helminth PLA2 protein that includes a phospholipase A$_2$-related domain, also referred to herein as a PLA$_2$-related domain. As disclosed herein, the C-terminal half of full-length parasitic helminth PLA2 proteins of the present invention, and particularly full-length D. immitis, O. volvulus, and B. malayi PLA2 proteins, are structurally similar to snake and mammalian PLA$_2$ enzymes. PLA$_2$-related domains can be identified by amino acid sequence analysis or by the ability of proteins having such domains to display PLA$_2$ activity.

Any parasitic helminth PLA2 protein is a suitable protein of the present invention. Suitable parasitic helminths from which to isolate PLA2 proteins (including isolation of the natural protein or production of the protein by recombinant or synthetic techniques) include nematodes, cestodes, and trematodes, with tissue-migrating nematodes being preferred. Preferred nematodes from which to isolate PLA2 proteins include filariid, ascarid, strongyle and trichostrongyle nematodes. Particularly preferred nematodes are those of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred nematodes include parasitic helminths of the genera Capillaria, Chabertia, Cooperia, Enterobius, Haemonchus, Nematodirus, oesophagostomum, Ostertagia, Trichostrongylus and Trichuris. Preferred filariid nematodes include Dirofilaria, Onchocerca, Acanthocheilonema, Brugia, Dipetalonema, Loa, Parafilaria, Setaria, Stephanofilaria and Wuchereria filariid nematodes. Particularly preferred parasitic helminths are nematodes of the genera Dirofilaria, Onchocerca, and Brugia. A preferred Dirofilaria species is D. immitis, ; which causes heartworm. Preferred Onchocerca species include O. volvulus (which infects humans), O. lienalis (which infects cattle), O. gutterosa (which infects cattle), O. gibsoni (which infects cattle), O. ochengi (which infects cattle) and O. cervicalis (which infects horses), with O. volvulus being more preferred. Preferred Brugia species include B. malayi (which infects humans) and B. pahangi (which infects cats), with B. malayi being more preferred.

A preferred parasitic helminth PLA2 protein of the present invention is a compound that when administered to an animal in an effective manner, is capable of protecting that animal from disease caused by a parasitic helminth. As such, the parasitic helminth is incapable (i.e., essentially unable) of causing disease in an animal that is immunized with a parasitic helminth PLA2 protein of the present invention. In accordance with the present invention, the ability of a PLA2 protein of the present invention to protect an animal from disease by a parasitic helminth refers to the ability of that protein to treat, ameliorate and/or prevent disease, including infection leading to disease, caused by the parasitic helminth, preferably by eliciting an immune response against the parasitic helminth and/or by reducing phospholipase $A_2$ activity. As used herein, an immune response can include humoral and/or cellular immune responses.

Suitable parasites to target include any parasite that is incapable of causing disease in an animal administered a PLA2 protein of the present invention. As such, a parasite to target includes any parasite that produces a protein having one or more epitopes that can be targeted by a humoral and/or cellular immune response against a PLA2 protein of the present invention and/or that can be targeted by a compound that otherwise inhibits PLA2 activity, thereby resulting in the reduced ability of the parasite to cause disease in an animal. Suitable and preferred parasites to target include those parasitic helminths disclosed above as being useful in the production of parasitic helminth proteins of the present invention.

One embodiment of the present invention is a fusion protein that includes a parasitic helminth PLA2 protein-containing domain attached to a fusion segment. Inclusion of a fusion segment as part of a PLA2 protein of the present invention can enhance the protein's stability during production, storage and/or use. Depending on the segment's characteristics, a fusion segment can also act as an immunopotentiator to enhance the immune response mounted by an animal immunized with a parasitic helminth PLA2 protein containing such a fusion segment. Furthermore, a fusion segment can function as a tool to simplify purification of a parasitic helminth PLA2 protein, such as to enable purification of the resultant fusion protein using affinity chromatography. A suitable fusion segment can be a domain of any size that has the desired function (e.g., imparts increased stability, imparts increased immunogenicity to a protein, and/or simplifies purification of a protein). It is within the scope of the present invention to use one or more fusion segments. Fusion segments can be joined to amino and/or carboxyl termini of the PLA2-containing domain of the protein. Linkages between fusion segments and PLA2-containing domains of fusion proteins can be susceptible to cleavage in order to enable straight-forward recovery of the PLA2-containing domains of such proteins. Fusion proteins are preferably produced by culturing a recombinant cell transformed with a fusion nucleic acid molecule that encodes a protein including the fusion segment attached to either the carboxyl and/or amino terminal end of a PLA2-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include PHIS-PDiPLA2$_{132}$ (also denoted PHIS-PLA2$_{417}$, PHIS-P22L$_{417}$, PHIS-PDiPLA2$_{417}$), PβGAL-POvPLA2$_{140}$, PHIS-POvPLA2$_{136}$ and PHIS-POvPLA2$_{120}$, the production of which are disclosed herein.

Another embodiment of the present invention is a parasitic helminth PLA2 protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a PLA2 protein of the present invention attached to one or more compounds protective against one or more other infectious agents, particularly an agent that infects humans, cats, dogs, cattle or horses, such as, but not limited to: viruses (e.g., caliciviruses, distemper viruses, hepatitis viruses, herpesviruses, immunodeficiency viruses, infectious peritonitis viruses, leukemia viruses, pan-leukopenia viruses, parvoviruses, rabies viruses, other cancer-causing or cancer-related viruses); bacteria (e.g., Leptospira, Rochalimaea); fungi and fungal-related microorganisms (e.g., Candida, Cryptococcus, Histoplasma); and other parasites (e.g., Babesia, Cryptosporidium, Eimeria, Encephalitozoon, Hepatozoon, Isospora, Microsporidia, Neospora, Nosema, Plasmodium, Pneumocystis, Toxoplasma, as well as helminth parasites, such as those disclosed herein). In one embodiment, a *D. immitis* PLA2 protein of the present invention is attached to one or more additional compounds protective against heartworm. In another embodiment, an *O. volvulus* PLA2 protein of the present invention is attached to one or more additional compounds protective against onchocerciasis. In yet another embodiment, a *B. malayi* PLA2 protein of the present invention is attached to one or more additional compounds protective against filariasis.

A preferred parasitic helminth PLA2 protein of the present invention is a protein encoded by a nucleic acid molecule that hybridizes under stringent hybridization conditions with nucleic acid molecule nDiPLA2$_{586}$, nOvPLA2$_{557}$, nBmPLA2(19)$_{242}$ and nBmPLA2(25)$_{255}$. Such a PLA2 protein is encoded by a nucleic acid molecule that hybridizes under stringent hybridization conditions with a nucleic acid molecule having nucleic acid sequence SEQ ID NO:1, a nucleic acid molecule having nucleic acid sequence SEQ ID NO:8, a nucleic acid molecule having nucleic acid sequence SEQ ID NO:15, and/or SEQ ID NO:18.

Translation of SEQ ID NO:1 suggests that nucleic acid molecule nDiPLA2$_{586}$ encodes a full-length *D. immitis* PLA2 protein of about 150 amino acids, referred to herein as PDiPLA2$_{150}$, assuming an open reading frame having an initiation (start) codon spanning from about nucleotide 7 through about nucleotide 9 of SEQ ID NO:1 and a termination (stop) codon spanning from about nucleotide 457 through about nucleotide 459 of SEQ ID NO:1. This open reading frame, excluding the stop codon, is referred to herein as nucleic acid molecule nDiPLA2$_{450}$ of the present invention, the nucleic acid sequence of which is represented herein by SEQ ID NO:3. It is to be noted that the open frame of nDiPLA2$_{586}$ extends an additional 6 nucleotides upstream from the first ATG codon to the beginning of the molecule.

The deduced amino acid sequence of PDiPLA2$_{150}$ is represented herein as SEQ ID NO:2. Analysis of SEQ ID NO:2 suggests that PDiPLA2$_{150}$ includes an amino terminal signal peptide through about amino acid 21 of SEQ ID NO:2. Amino-terminal sequencing of the processed protein supports this deduction; details are provided in the Examples section. As such, the present invention also includes a processed protein denoted PDiPLA2$_{129}$, represented by amino acid sequence SEQ ID NO:5, which is encoded by nucleic acid molecule nDiPLA2$_{387}$, the nucleic acid sequence of which is represented herein as SEQ ID NO:4, as well as a signal segment of about 21 amino acids having amino acid sequence SEQ ID NO:7, encoded by nucleic acid molecule nDiPLA2$_{63}$, the nucleic acid sequence of which is represented herein as SEQ ID NO:6.

The calculated molecular weights of PDiPLA2$_{150}$ and of PDiPLA2$_{129}$ are, respectively, 17.5 kD and 15.3 kD. The molecular weights of these proteins as determined by subjecting the proteins to SDS PAGE appear to be higher. For example, PDiPLA2$_{150}$ has an apparent molecular weight of about 22 kD when subjected to (or, in other words, as measured by) Tris-glycine SDS PAGE and a molecular weight of about 19 kD when subjected to Tris-tricine SDS-PAGE. PDiPLA2$_{129}$ has a molecular weight of about 20.5 kD when subjected to Tris-glycine SDS-PAGE and of about 16 kD when subjected to Tris-tricine SDS-PAGE. PDiPLA2$_{150}$ and PDiPLA2$_{129}$ have calculated estimated pI's of about 4.58 and about 4.52, respectively.

As disclosed above, the approximate C-terminal half of PDiPLA2$_{150}$ (and, as such that of PDiPLA2$_{129}$) is similar in amino acid sequence to a variety of snake and mammalian PLA$_2$ amino acid sequences, the similarities being particularly well conserved with respect to cysteines and the amino acids comprising the active site. A BLAST search of the NCBI non-redundant data library (SWISS-PROT ver. 23.0, PIR ver. 34.0, GenPept CDS translations from GenBank release 73.1) using amino acids 80–104 (i.e., DGKMK HCKTH EACYD QREPQ SWCIL) of amino acid sequence SEQ ID NO:2 yielded 40 records, 39 of which were snake or mammalian PLA$_2$ sequences. Twenty-five of the 29 SWISS-PROT match sequences represent PLA$_2$ venoms from a variety of snakes while the other four sequences were mammalian pancreatic PLA$_2$ sequences. No non-mammal, non-arthropod eukaryotic entries were found. The highest percent identity between the region of PDiPLA2$_{150}$ spanning from about amino acid 80 through about amino acid 104 and known sequences was about 40%. The highest percent identity between the region of PDiPLA2$_{150}$ spanning from about amino acid 85 through about amino acid 102 and known sequences was about 55%. Overall identity between PDiPLA2$_{150}$ and known sequences was significantly less than 30%.

Translation of SEQ ID NO:8 suggests that nucleic acid molecule nOvPLA2$_{557}$ encodes a full-length O. volvulus PLA2 protein of about 140 amino acids, referred to herein as POvPLA2$_{140}$, assuming an open reading frame having a start codon spanning from about nucleotide 4 through about nucleotide 6 of SEQ ID NO:8 and a stop codon spanning from about nucleotide 424 through about nucleotide 426 of SEQ ID NO:8. This open reading frame, excluding the stop codon, is referred to herein as nucleic acid molecule nOv-PLA2$_{420}$ of the present invention, the nucleic acid sequence of which is represented herein by SEQ ID NO:10. The nucleic acid sequences of O. volvulus nucleic acid molecule nOvPLA2$_{557}$ and D. immitis nucleic acid molecule nDiPLA2$_{586}$ are about 61% identical overall, including about 58% identity in the coding region and about 70% identity in the 3' untranslated region.

The deduced amino acid sequence of POvPLA2$_{140}$ is represented herein as SEQ ID NO:9. Analysis of SEQ ID NO:9 suggests that POvPLA2$_{140}$ includes an amino terminal signal peptide through about amino acid 22 of SEQ ID NO:9. Amino-terminal sequencing of the processed protein supports this deduction; details are provided in the Examples section. As such, the present invention also includes a processed protein denoted POvPLA2$_{118}$, represented by amino acid sequence SEQ ID NO:12, which is encoded by nucleic acid molecule nOvPLA2$_{354}$, the nucleic acid sequence of which is represented herein as SEQ ID NO:11, as well as a signal segment of about 22 amino acids, denoted POvPLA2$_{22}$ having amino acid sequence SEQ ID NO:14, encoded by nucleic acid molecule nOvPLA2$_{66}$, the nucleic acid sequence of which is represented herein as SEQ ID NO:13.

The deduced amino acid sequence of SEQ ID NO:9 suggests a protein having a molecular weight of about 15.8 kD and an estimated pI of about 3.96. The amino acid sequence of SEQ ID NO:9 is about 44 percent identical to the amino acid sequence of PDiPLA2$_{150}$ (i.e., SEQ ID NO:2). The C-terminal 80-amino acid regions of the O. volvulus and D. immitis PLA2 proteins are about 60 percent identical and exhibit strict conservation of 8 cysteine residues and of a histidine residue at position 80 (amino acid numbering as in SEQ ID NO:9). Both SEQ ID NO:2 and SEQ ID NO:9 are highly hydrophilic except for having hydrophobic amino termini with the characteristics of signal segments. SEQ ID NO:9 has a potential glycosylation site from amino acids about 134 to about 136 not found in amino acid sequence SEQ ID NO:2.

The C-terminal half of O. volvulus PLA2 protein POvPLA2$_{140}$ also shows amino acid sequence similarity to a variety of snake and mammalian PLA$_2$ amino acid sequences (details are presented in the Examples), the similarities being particularly well conserved with respect to the cysteines and the amino acids comprising the active site, one of which is the aforementioned histidine at position about 80 of SEQ ID NO:9. Overall identity between SEQ ID NO:9 and known proteins is significantly less than 30%.

It is of note that despite the relatively low degree of similarity between the O. volvulus and D. immitis PLA2 proteins, nucleic acid molecules having SEQ ID NO:8 can be amplified by the polymerase chain reaction from O. volvulus cDNA libraries using primers corresponding to the nucleic acid sequence encoding D. immitis PLA2; details are provided in the Examples. This finding supports the ability to obtain any parasitic helminth PLA2 protein and nucleic acid molecule given the protein and nucleic acid sequences disclosed herein.

For example, B. malayi PLA2 nucleic acid molecules nBmPLA2(19)$_{242}$ and nBmPLA2(25)$_{255}$ have each been isolated from B. malayi genomic DNA using D. immitis and O. volvulus PLA2 nucleic acid molecules as disclosed in detail in the Examples. Nucleic acid molecule nBmPLA2 (19)$_{242}$, the nucleic acid sequence of which is represented in SEQ ID NO:15 includes two coding regions separated by an intron, the coding regions spanning from about nucleotide 2 through about nucleotide 60 and from about nucleotide 140 through about nucleotide 242. A nucleic acid molecule containing a contiguous open reading frame of about 162 nucleotides derived from nBmPLA2(19)$_{242}$ is denoted herein as nBmPLA2(19)$_{163}$, and has nucleic acid sequence SEQ ID NO:16. The nucleic acid sequence of nucleic acid molecule nBmPLA2(19)$_{163}$ is about 78% identical with the corresponding region of nDiPLA2$_{586}$ (spanning from about nucleotide 300 through about nucleotide 415 of SEQ ID NO:1) and about 60% identical with the corresponding region of nOvPLA2$_{557}$ (spanning from about nucleotide 270 through about 382 nucleotide of SEQ ID NO:8).

Translation of SEQ ID NO:16, beginning at about nucleotide 2, indicates that nBmPLA2(19)$_{163}$ encodes a protein of about 54 amino acids, denoted herein as PBmPLA2(19)$_{54}$, the amino acid sequence of which is represented herein as SEQ ID NO:17. The amino acid sequence of PBmPLA2 (19)$_{54}$ is about 66% identical with the corresponding region of PDiPLA2$_{150}$ (spanning from about amino acid 99 to about amino acid 136 of SEQ ID NO:2) and about 47% identical with the corresponding region of POvPLA2$_{140}$ (spanning from about amino acid 94 to about amino acid 130 of SEQ ID NO:9). Overall identity between SEQ ID NO:17 and known proteins is less than about 20%.

Nucleic acid molecule nBmPLA2(25)$_{255}$, the nucleic acid sequence of which is represented in SEQ ID NO:18 includes two coding regions separated by an intron, the coding regions spanning from about nucleotide 2 through about nucleotide 60 and from about nucleotide 153 through about nucleotide 255. A nucleic acid molecule containing a contiguous open reading frame of about 162 nucleotides derived from nBmPLA2(25)$_{255}$ is denoted herein as nBmPLA2(25)$_{163}$, and has nucleic acid sequence SEQ ID NO:19. The nucleic acid sequence of nucleic acid molecule nBmPLA2 (25)$_{163}$ is about 70% identical with the corresponding region of nDiPLA2$_{586}$ (spanning from about nucleotide 300 through about nucleotide 415 of SEQ ID NO:1) and about 55% identical with the corresponding region of nOvPLA2$_{557}$ (spanning from about nucleotide 270 through about 382 nucleotide of SEQ ID NO:8). The nucleic acid sequences of nBmPLA2(19)$_{242}$ and nBmPLA2(25)$_{255}$ are about 62% identical, whereas the nucleic acid sequences of nBmPLA2(19)$_{163}$ and nBmPLA2(25)$_{163}$ are about 72% identical.

Translation of SEQ ID NO:19, beginning at about nucleotide 2, indicates that nBmPLA2(25)$_{163}$ encodes a protein of about 54 amino acids, denoted herein as PBmPLA2(25)$_{54}$, the amino acid sequence of which is represented herein as SEQ ID NO:20. The amino acid sequence of PBmPLA2 (25)$_{54}$ is about 58% identical with the corresponding region of PDiPLA2$_{150}$ (spanning from about amino acid 99 to about amino acid 136 of SEQ ID NO:2) and about 40% identical with the corresponding region of POvPLA2$_{140}$ (spanning from about amino acid 94 to about amino acid 130 of SEQ ID NO:9). The amino acid sequences of PBmPLA2(19) $_{54}$ and of PBmPLA2(25) $_{54}$ are about 68% identical. Overall identity between SEQ ID NO:20 and known proteins is less than about 20%.

Preferred parasitic helminth PLA2 proteins of the present invention include proteins comprising amino acid sequences that are at least about 30%, preferably at least about 50%, more preferably at least about 75% and even more preferably at least about 90% identical to amino acid sequence SEQ ID NO:2, SEQ ID NO:9, SEQ ID NO:17 and/or SEQ ID NO:20. More preferred parasitic helminth PLA2 proteins of the present invention include: proteins encoded by at least a portion of SEQ ID NO:1 and, as such, have amino acid sequences that include at least a portion of SEQ ID NO:2; proteins encoded by at least a portion of SEQ ID NO:8 and, as such, have amino acid sequences that include at least a portion of SEQ ID NO:9; proteins encoded by at least a portion of SEQ ID NO:16 and, as such, have amino acid sequences that include at least a portion of SEQ ID NO:17; and proteins encoded by at least a portion of SEQ ID NO:19 and, as such, have amino acid sequences that include at least a portion of SEQ ID NO:20.

Particularly preferred parasitic helminth proteins of the present invention are proteins that include SEQ ID NO:2, SEQ ID NO:5, SEQ ID NO:7, SEQ ID NO:9, SEQ ID NO:12, SEQ ID NO:14, SEQ ID NO:17, and/or SEQ ID NO:20 (including, but not limited to the encoded proteins, full-length proteins, processed proteins, fusion proteins and multivalent proteins thereof) as well as proteins that are truncated homologues of proteins that include as least portions of SEQ ID NO:2, SEQ ID NO:5, SEQ ID NO:7, SEQ ID NO:9, SEQ ID NO:12, SEQ ID NO:14, SEQ ID NO:17, and/or SEQ ID NO:20. Even more preferred proteins include PDiPLA2$_{150}$, PDiPLA2$_{129}$, PDiPLA2$_{21}$, PHIS-PDiPLA2$_{132}$, POvPLA2$_{140}$, POvPLA2$_{118}$, POvPLA2$_{22}$, PβGAL-POvPLA2$_{140}$, PHIS-POvPLA2$_{136}$, PHIS-POvPLA2$_{120}$, PBmPLA2(19)54 and PBmPLA2(25)54. Examples of methods to produce such proteins are disclosed herein, including in the Examples section.

One embodiment of the present invention is an isolated parasitic helminth nucleic acid molecule that hybridizes under stringent hybridization conditions with at least one of the following genes: D. immitis PLA2 gene, an O. volvulus PLA2 gene, and a B. malayi PLA2 gene. Identifying characteristics of such genes are heretofore described. A nucleic acid molecule of the present invention can include an isolated natural parasitic helminth PLA2 gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with one of the aforementioned genes under stringent hybridization conditions. Suitable and preferred parasitic helminths are disclosed above.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated parasitic helminth PLA2 nucleic acid molecule of the present invention can be obtained from its natural source either as an entire (i.e., complete) gene or a portion thereof capable of forming a stable hybrid with that gene. An isolated parasitic helminth PLA2 nucleic acid molecule can also be produced using recombinant DNA technology (e.g., polymerase chain reaction (PCR) amplification, cloning) or chemical synthesis. Isolated parasitic helminth PLA2 nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a parasitic helminth PLA2 protein of the present invention or to form stable hybrids under stringent conditions with natural gene isolates.

A parasitic helminth PLA2 nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., ability to elicit an immune response against at least one epitope of a parasitic helminth PLA2 protein, ability to bind to immune serum) and/or by hybridization with a *D. immitis* PLA2 gene, with an *O. volvulus* PLA2 gene, and/or with a *B. malayi* PLA2 gene.

An isolated nucleic acid molecule of the present invention can include a nucleic acid sequence that encodes at least one parasitic helminth PLA2 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth PLA2 protein. As heretofore disclosed, parasitic helminth PLA2 proteins of the present invention include, but are not limited to, proteins having full-length parasitic helminth PLA2 coding regions, proteins having partial parasitic helminth PLA2 coding regions, fusion proteins, multivalent protective proteins and combinations thereof.

At least certain nucleic acid molecules of the present invention encode proteins that selectively bind to immune serum (i.e., to immune serum) derived from an animal that is immune to infection by the parasitic helminth from which the nucleic acid molecule was isolated. The immune serum is preferably derived from an animal immunized with a composition comprising parasitic helminth third stage and/or fourth stage larvae. Examples of such nucleic acid molecules include, but are not limited to, nucleic acid molecules nDiPLA2$_{586}$, nDiPLA2$_{450}$, nDiPLA2$_{387}$, nDiPLA2$_{475}$, nDiPLA2$_{417}$, nOvPLA2$_{557}$, nOvPLA2$_{420}$, nOvPLA2$_{354}$, nOvPLA2$_{542}$ and nOvPLA2$_{496}$.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, the nucleic acid molecule being delivered to the animal by direct injection (i.e, as a naked nucleic acid) or in a vehicle such as a recombinant virus vaccine or a recombinant cell vaccine.

One embodiment of the present invention is a parasitic helminth PLA2 nucleic acid molecule that hybridizes under stringent hybridization conditions with at least one of the following nucleic acid molecules: nDiPLA2$_{586}$, nOvPLA2$_{557}$, nBmPLA2(19)$_{242}$, and nBmPLA2(25)$_{255}$. Such parasitic helminth nucleic acid molecules can hybridize under stringent hybridization conditions with a nucleic acid molecule having nucleic acid sequence SEQ ID NO:1, with a nucleic acid molecule having nucleic acid sequence SEQ ID NO:8, with a nucleic acid molecule having nucleic acid sequence SEQ ID NO:15, and with a nucleic acid molecule having nucleic acid sequence SEQ ID NO:18.

Comparison of SEQ ID NO:1, SEQ ID NO:8, SEQ ID NO:15 and SEQ ID NO:18 with known nucleic acid sequences demonstrates that the percent identity between parasitic helminth PLA2 nucleic acid sequences and known sequences (such as those of snake and mammalian PLA2 genes) is relatively small and, as such, parasitic helminth PLA2 nucleic acid molecules represent a novel class of nucleic acid molecules. Preferred parasitic helminth nucleic acid molecules include nucleic acid molecules having a nucleic acid sequence that is at least about 50%, preferably at least about 70%, more preferably at least about 80%, and even more preferably at least about 90% identical to nucleic acid sequences SEQ ID NO:1, SEQ ID NO:8, SEQ ID NO:15 and SEQ ID NO:18.

A preferred nucleic acid molecule of the present invention includes at least a portion of nucleic acid sequence SEQ ID NO:1, SEQ ID NO:8, SEQ ID NO:15 and/or SEQ ID NO:18 that capable of hybridizing (i.e., the hybridizes under stringent hybridization conditions) to a *D. immitis* PLA2 gene, to an *O. volvulus* PLA2 gene, and/or to a *B. malayi* PLA2 gene of the present invention. More preferred is a nucleic acid molecule that includes nucleic acid sequence SEQ ID NO:1, nucleic acid sequence SEQ ID NO:3, nucleic acid sequence SEQ ID NO:4, nucleic acid sequence SEQ ID NO:6, nucleic acid sequence SEQ ID NO:8, nucleic acid sequence SEQ ID NO:10, nucleic acid sequence SEQ ID NO:11, nucleic acid sequence SEQ ID NO:13, nucleic acid sequence SEQ ID NO:15, nucleic acid sequence SEQ ID NO:16, nucleic acid sequence SEQ ID NO:18, and/or nucleic acid sequence SEQ ID NO:19, as well as a nucleic acid molecule that is an allelic variant of any of those nucleic acid molecules. Such preferred nucleic acid molecules can include nucleotides in addition to those included in the SEQ ID NOs, such as, but not limited to, a full-length gene, a full-length coding region, a nucleic acid molecule encoding a fusion protein, and/or a nucleic acid molecule encoding a multivalent protective compound. Particularly preferred nucleic acid molecules include nDiPLA2$_{586}$, nDiPLA2$_{450}$, nDiPLA2$_{387}$, nDiPLA2$_{63}$, nDiPLA2$_{475}$, nDiPLA2$_{463}$, nDiPLA2$_{417}$, nOvPLA2$_{557}$, nOvPLA2$_{420}$, nOvPLA2$_{354}$, nOvPLA2$_{66}$, nOvPLA2$_{542}$, nOvPLA2$_{496}$, nOvPLA2$_{430}$, nOvPLA2$_{425}$, nOvPLA2$_{158}$, nBmPLA2(19)$_{242}$, nBmPLA2(19)$_{163}$, nBmPLA2(25)$_{255}$, and nBmPLA2(25)$_{163}$.

The present invention also includes nucleic acid molecules encoding a protein including at least a portion of SEQ ID NO:2, nucleic acid molecules encoding a protein having at least a portion of SEQ ID NO:5, nucleic acid molecules encoding a protein having at least a portion of SEQ ID NO:7, nucleic acid molecules encoding a protein having at least a portion of SEQ ID NO:9, nucleic acid molecules encoding a protein having at least a portion of SEQ ID NO:12, nucleic acid molecules encoding a protein having at least a portion of SEQ ID NO:14, nucleic acid molecules encoding a protein having at least a portion of SEQ ID NO:17, and/or nucleic acid molecules encoding a protein having at least a portion of SEQ ID NO:20, including nucleic acid molecules that have been modified to accommodate codon usage properties of the cells in which such nucleic acid molecules are to be expressed.

Knowing the nucleic acid sequences of certain parasitic helminth PLA2 nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain PLA2 nucleic acid molecules for other parasitic helminths, particularly since, as described in detail in the Examples section, knowledge of D. immitis PLA2 nucleic acid molecules of the present invention enabled the isolation of 0. volvulus PLA2 nucleic acid molecules of the present invention, and knowledge of those nucleic acid molecules enabled the isolation of B. malayi PLA2 nucleic acid molecules of the present invention. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include parasitic helminth L3 and/or L4 larval libraries as well as genomic DNA libraries. Similarly, preferred DNA sources to screen or from which to amplify nucleic acid molecules include parasitic helminth L3 and/or L4 larval DNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising parasitic helminth PLA2 genes or other parasitic helminth PLA2 nucleic acid molecules. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit PLA2 protein production or activity. Such therapeutic applications include the use of such oligonucleotides in, for example, antisense-, triplex formation-, ribozyme- and/or RNA drug-based technologies. The present invention, therefore, includes such oligonucleotides and methods to protect animals from diseases caused by parasitic helminths by use of one or more of such technologies. Appropriate oligonucleotide-containing therapeutic compositions can be administered to an animal, using techniques known to those skilled in the art, either prior to or after infection by a parasitic helminth, such as D. immitis, O. volvulus, or B. malayi, in order to protect the animal from disease.

The present invention also includes a recombinant vector, which includes at least one parasitic helminth PLA2 nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule (s) are derived. The vector can be either RNA or DNA, either prokaryotic or eukaryotic, and typically is a virus or a plasmid. Recombinant vectors can be used in the cloning, sequencing, and/or otherwise manipulating of parasitic helminth PLA2 nucleic acid molecules of the present invention. One type of recombinant vector, referred to herein as a recombinant molecule and described in more detail below, can be used in the expression of nucleic acid molecules of the present invention. Preferred recombinant vectors are capable of replicating in the transformed cell.

Suitable and preferred nucleic acid molecules to include in recombinant vectors of the present invention are as disclosed herein for suitable and preferred parasitic helminth PLA2 nucleic acid molecules per se. Particularly preferred nucleic acid molecules to include in recombinant vectors, and particularly in recombinant molecules, of the present invention include $nDiPLA2_{586}$, $nDiPLA2_{450}$, $nDiPLA2_{387}$, $nDiPLA2_{63}$, $nDiPLA2_{475}$, $nDiPLA2_{463}$, $nDiPLA2_{417}$, $nOvPLA2_{557}$, $nOvPLA2_{420}$, $nOvPLA2_{354}$, $nOvPLA2_{66}$, $nOvPLA2_{542}$, $nOvPLA2_{496}$, $nOvPLA2_{430}$, $nOvPLA2_{425}$, $nOvPLA2_{158}$, $nBmPLA2(19)_{242}$, $nBmPLA2(19)_{163}$, $nBmPLA2(25)_{255}$, and $nBmPLA2(25)_{163}$.

Isolated parasitic helminth PLA2 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred parasitic helminth PLA2 nucleic acid molecules per se. Particularly preferred nucleic acid molecules to include in recombinant cells of the present invention include $nDiPLA2_{586}$, $nDiPLA2_{450}$, $nDiPLA2_{387}$, $nDiPLA2_{63}$, $nDiPLA2_{475}$, $nDiPLA2_{463}$, $nDiPLA2_{417}$, $nOvPLA2_{557}$, $nOvPLA2_{420}$, $nOvPLA2_{354}$, $nOvPLA2_{66}$, $nOvPLA2_{542}$, $nOvPLA2_{496}$, $nOvPLA2_{430}$, $nOvPLA2_{425}$, $nOvPLA2_{158}$, $nBmPLA2(19)_{242}$, $nBmPLA2(19)_{163}$, $nBmPLA2(25)_{255}$, and $nBmPLA2(25)_{163}$. Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing parasitic helminth PLA2 proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_\chi$3987 and SR-11 $_\chi$4072; *Spodoptera frugiperda; Trichoplusia ni;* BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types heretofore disclosed.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments and fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Suitable signal segments include natural signal segments (e.g., a parasitic helminth PLA2 signal segment) or any heterologous signal segment capable of directing the secretion of a protein of the present invention. Preferred signal segments include, but are not limited to, parasitic helminth PLA2, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (λ) (such as λp$_L$ and λp$_R$ and fusions that include such promoters), bacteriophage T7, T7lac, bacteriophage T3, bacteriophage SP6, bacteriophage SP01, metallothionein, α-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, poxvirus, adenovirus, cytomegalovirus (such as intermediate early promoters, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a parasitic helminth, such as a *D. immitis, O. volvulus* or *B. malayi* molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include pHis-nDiPLA2$_{417}$ (i.e., pET19b-PLA2$_{417}$), pBv-nDiPLA2$_{475}$ (i.e., p76-79-A6), pSP-nDiPLA2$_{475}$ (i.e., p76-79.C2), pSv-nDiPLA2$_{475}$ (i.e., p88-36.1B), pβgal-nOvPLA2$_{557}$, pHis-nOvPLA2$_{542}$, pHis-nOvPLA2$_{496}$, pTECH-nOvPLA2$_{557}$, pVL1393-nOvPLA2$_{425}$, pPVXC-nDiPLA2$_{463}$ pPVXRC-nDiPLA2$_{463}$, pPVXC-nOvPLA2$_{430}$ and pPVXRC-nOvPLA2$_{430}$. Details regarding the production of such recombinant molecules are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include *E. coli:*pHis-nDiPLA$_{417}$, *S. frugiperda:*pBv-nDiPLA2$_{475}$, BHK:pSv-nDiPLA2$_{475}$, *E. coli:*pβgal-nOvPLA2$_{557}$, *E. coli:*pHis-nOvPLA2$_{542}$, *E. coli:*pHis-nOvPLA2$_{496}$, Salmonella:pTECH-nOvPLA2$_{557}$, and *S. frugiperda:*pVL1393-nOvPLA2$_{425}$. Details regarding the production of these recombinant cells are disclosed herein.

Recombinant cells of the present invention can also be co-transformed with one or more recombinant molecules including parasitic helminth PLA2 nucleic acid molecules encoding one or more proteins of the present invention and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a parasitic helminth PLA2 protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli;* or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a parasitic helminth PLA2 protein of the present invention or to a mimetope thereof. Such antibodies are also referred to herein as anti-parasitic helminth PLA2 antibodies. Particularly preferred antibodies of this embodiment include anti-*D. immitis* PLA2 antibodies, anti-*O. volvulus* PLA2 antibodies, and anti-*B. malayi* PLA2 antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid. An anti-parasitic helminth PLA2 antibody preferably binds to a parasitic helminth PLA2 protein in such a way as to reduce the activity of that protein.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce parasitic helminth PLA2 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art. Suitable cytotoxic agents include, but are not limited to: double-chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but lack the toxin's intrinsic cell binding domain.

One embodiment of the present invention is a therapeutic composition that, when administered to an animal in an effective manner, is capable of protecting that animal from disease caused by a parasitic helminth. Therapeutic compositions of the present invention include at least one of the following protective compounds: (a) an isolated PLA2 protein or a mimetope thereof; (b) an isolated parasitic helminth nucleic acid molecule that hybridizes under stringent hybridization conditions with a gene selected from the group consisting of a *Dirofilaria immitis* PLA2 gene, an *Onchocerca volvulus* PLA2 gene, and a Brugia malayi PLA2 gene; (c) an isolated antibody that selectively binds to a parasitic helminth PLA2 protein; (d) an inhibitor of phospholipase $A_2$ activity identified by its ability to inhibit parasitic helminth phospholipase $A_2$ activity; and (e) a mixture (i.e., combination) of at least two of the compounds. As used herein, a protective compound refers to a compound that, when administered to an animal in an effective manner, is able to treat, ameliorate, and/or prevent disease caused by a parasitic helminth of the present invention. Preferred helminths to target are heretofore disclosed. Examples of proteins, nucleic acid molecules, antibodies and methods to identify inhibitors of the present invention are disclosed herein.

The present invention also includes a therapeutic composition comprising at least one parasitic helminth PLA2-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm include dogs, cats, humans and ferrets, with dogs and cats being particularly preferred. Preferred animals to protect against onchocerciasis include humans, cattle and horses, with humans being particularly preferred. Preferred animals to protect against filariasis and other diseases caused by Brugia helminths include humans and cats (including house cats and other felines).

In one embodiment, a therapeutic composition of the present invention can be administered to the vector in which the parasitic helminth develops, such as to a mosquito in order to prevent the spread of heartworm and/or filariasis or to a black fly in order to prevent the spread of onchocerciasis. Such administration could be orally or by developing transgenic vectors capable of producing at least one therapeutic composition of the present invention. In another embodiment, a vector, such as a mosquito or a black fly, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax™ adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphere, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from disease caused by a parasitic helminth of the present invention, a therapeutic composition of the present invention is administered to the animal in an effective manner such that the composition is capable of protecting that animal from a disease caused by a parasitic helminth. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of parasitic helminth PLA2 proteins in order to interfere with development of parasitic helminths targeted in accordance with the present invention.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. Such a vaccine can comprise any nucleic acid molecule or recombinant molecule of the present invention. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences, such as that of bovine growth hormone, are also preferred. Particularly preferred naked nucleic acid vaccines include pPVXC-nDiPLA$2_{463}$, pPVXRC-nDiPLA$2_{463}$, pPVXC-nOvPLA$2_{430}$ and pPVXRC-nOvPLA$2_{430}$.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccine ranges from about 1 nanogram (ng) to about 100 $\mu$g, depending on the route of administration and/or method of delivery, as can be determined by those skilled in the art. Suitable delivery methods include, for example, by injection, as drops, aerosolized and/or topically. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

A recombinant virus vaccine of the present invention includes a recombinant molecule of the present invention that is packaged in a viral coat and that can be expressed in an animal after administration. Preferably, the recombinant molecule is packaging-deficient. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), species-specific herpesviruses and species-specific poxviruses. Methods to produce and use recombinant virus vaccines are disclosed in PCT Publication No. WO 94/17813, by Xiong et al., published Aug. 18, 1994, which is incorporated by reference herein in its entirety. Examples of recombinant virus vaccines of the present invention are disclosed in the Examples section.

When administered to an animal, a recombinant virus vaccine of the present invention infects cells within the immunized animal and directs the production of a protective protein or RNA nucleic acid molecule that is capable of protecting the animal from disease caused by a parasitic helminths as disclosed herein. For example, a recombinant virus vaccine comprising a *D. immitis* PLA2 nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells that express at least one protein of the present invention. Preferred recombinant cells for use in this embodiment include Salmonella, *E. coli*, Listeria, Mycobacterium, *S. frugiperda*, BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells or cell lysates.

In common with most other enteric pathogens, Salmonella strains normally enter the host orally. Once in the intestine, they interact with the mucosal surface, normally to establish an invasive infection. Most Salmonella infections are controlled at the epithelial surface, causing the typical Salmonella-induced gastroenteritis. Some strains of Salmonella, including *S. typhi* and some *S. typhimurium* isolates, have evolved the ability to penetrate deeper into the host, causing a disseminated systemic infection. It appears such strains have the capacity to resist the killing actions of macrophages and other immune cells. *S. typhi* can exist for long periods as a facultative intracellular parasite. Some of the live vaccine strains can also persist for long periods in the mononuclear phagocyte system. Hosts infected in such a manner develop, in addition to a mucosal immune response, systemic cellular and serum antibody responses to the Salmonella. Thus, invading Salmonella, whether virulent or attenuated, can stimulate strong immune responses, unlike many other enteric pathogens which only set up local, noninvasive gut infections. The potent immunogenicity of live Salmonella makes them attractive candidates for carrying parasitic helminth PLA2 nucleic acid molecules and proteins of the present invention to the immune system.

A preferred recombinant cell-based vaccine is one in which the cell is attenuated. *Salmonella typhimurium* strains, for example, can be attenuated by introducing mutations into genes critical for in vivo growth and survival. For example, genes encoding cyclic adenosine monophosphate (cAMP) receptor protein or adenylate cyclase are deleted to produce avirulent, vaccine strains. Such strains can deliver antigens to lymphoid tissue in the gut but demonstrate reduced capacity to invade the spleen and mesenteric lymph nodes. These strains are still capable of stimulating both humoral and cellular immunity in mammalian hosts.

Recombinant cell vaccines can be used to introduce parasitic helminth PLA2 proteins of the present invention into the immune systems of animals. For example, recombinant molecules comprising parasitic helminth nucleic acid molecules of the present invention operatively linked to expression vectors that function in Salmonella can be transformed into Salmonella host cells. The resultant recombinant cells are then introduced into the animal to be protected. Preferred Salmonella host cells are those for which survival depends on their ability to maintain the recombinant molecule (i.e., a balanced-lethal host-vector system). An example of such a preferred host/recombinant molecule combination is a Salmonella strain (e.g., UK-1 $_\chi$3987 or SR-11 $_\chi$4072) which is unable to produce aspartate β-semialdehyde dehydrogenase in combination with a recombinant molecule also capable of encoding the enzyme. Aspartate β-semialdehyde dehydrogenase, encoded by the asd gene, is an important enzyme in the pathway to produce diaminopimelic acid (DAP). DAP is an essential component of the peptidoglycan of the cell wall of Gram-negative bacteria, such as Salmonella, and, as such, is necessary for survival of the cell. Thus, Salmonella lacking a functional asd gene can only survive if they maintain a recombinant molecule that is also capable of expressing a functional asd gene.

In one embodiment, an Onchocerca PLA2 nucleic acid molecule of the present invention, such as nOvPLA2$_{557}$, is operatively linked to expression vector pTECH-1 (available from Medeva, London, U.K.), and the resulting recombinant molecule, denoted herein as pTECH-nOvPLA2$_{557}$ is transfected into a Salmonella strain, such as BRD 509 (available from Medeva), to form recombinant cell Salmonella:pTECH-nOvPLA2$_{557}$. Such recombinant cells can be used to produce the corresponding encoded PLA2 protein or can be used as recombinant cell vaccines. In a similar manner, other parasitic helminth Salmonella recombinant cell vaccines, such as, but not limited to, those containing Dirofilaria and/or Brugia nucleic acid molecules can be produced and used.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Such techniques are known to those skilled in the art.

One preferred embodiment of the present invention is the use of parasitic helminth PLA2 proteins, nucleic acid molecules and antibodies of the present invention, and particularly *D. immitis* PLA2 proteins, nucleic acid molecules and antibodies of the present invention, to protect an animal from heartworm. It is particularly preferred to prevent L3 larvae that are delivered to the animal by the mosquito intermediate host from maturing into adult worms. As such, preferred therapeutic compositions are those that are able to inhibit at least one step in the portion of the parasite's development cycle that includes L3 larvae, third molt, L4 larvae, fourth molt, immature adult prior to entering the circulatory system. In dogs, this portion of the development cycle is about 70 days. Particularly preferred therapeutic compositions include *D. immitis* PLA2-based therapeutic compositions of the present invention, particularly since PLA2 expression is apparently linked to L3 and L4 development. Such compositions include *D. immitis* PLA2 nucleic acid molecules, *D. immitis* PLA2 proteins and mimetopes thereof, anti-*D. immitis* PLA2 antibodies, and inhibitors of *D. immitis* phospholipase A₂ activity. Such compositions are administered to animals in a manner effective to protect the animals from heartworm. Additional protection may be obtained by administering additional protective compounds, including other *D. immitis* proteins, nucleic acid molecules and antibodies.

Another preferred embodiment of the present invention is the use of parasitic helminth PLA2 proteins, nucleic acid molecules and antibodies of the present invention, and particularly *O. volvulus* PLA2 proteins, nucleic acid molecules and antibodies of the present invention, to protect a human from onchocerciasis. It is particularly preferred to prevent L3 larvae that are delivered to the animal by the black fly intermediate host from maturing into adult worms. Preferred therapeutic compositions are those that are able to inhibit at least one step in the portion of the parasite's development cycle that includes L3 larvae, third molt, L4 larvae, fourth molt and immature adult prior to entering the subcutaneous tissues. In humans infected with *O. volvulus*, this portion of the development cycle is about 150 days. As such, preferred therapeutic compositions include *O. volvulus* PLA2-based therapeutic compositions of the present invention, particularly since PLA2 expression is apparently linked to L3 and L4 development. Such compositions include *O. volvulus* PLA2 nucleic acid molecules, *O. volvulus* PLA2 proteins and mimetopes thereof, anti-*O. volvulus* PLA2 antibodies, and inhibitors of *O. volvulus* phospholipase A₂ activity. Such compositions are administered to humans in a manner effective to protect humans from onchocerciasis. Additional protection may be obtained by administering additional protective compounds, including other Onchocerca, preferably *O. volvulus*, proteins, nucleic acid molecules and antibodies.

One therapeutic composition of the present invention includes an inhibitor of parasitic helminth phospholipase A₂ activity, i.e., a compound capable of substantially interfering with the function of a parasitic helminth phospholipase A₂ susceptible to inhibition by an inhibitor of parasitic helminth phospholipase A₂ activity.

As heretofore disclosed, phospholipase A₂ enzymes catalyze the hydrolysis of the 2-acyl ester group of sn-3-glycerophospholipids. Without being bound by theory, it is believed that parasite phospholipase A₂ enzymes may be important in molting and tissue migration as such enzymes are likely to effect lipid metabolism, and particularly host and parasite membrane metabolism. As such, inhibitors of parasitic helminth phospholipase A₂ could be particularly beneficial in disrupting molting by helminths in general and tissue migration by those helminths capable of such migration.

An inhibitor of phospholipase A₂ activity can be identified using parasitic helminth, and preferably *D. immitis, O. volvulus*, and/or *B. malayi* PLA2 proteins of the present invention. One embodiment of the present invention is a method to identify a compound capable of inhibiting phospholipase A₂ activity of a parasitic helminth. Such a method includes the steps of (a) contacting (e.g., combining, mixing) an isolated parasitic helminth PLA2 protein with a putative inhibitory compound under conditions in which, in the absence of the compound, the protein has phospholipase A₂ activity, and (b) determining if the putative inhibitory compound inhibits the phospholipase A₂ activity. Putative inhibitory compounds to screen include organic molecules, antibodies (including mimetopes thereof) and substrate analogs. Methods to determine phospholipase A₂ activity are known to those skilled in the art; see, for example, Franson et al., 1974, *J. Lipid Res.* 15, 380–388; Clark et al., 1991, *Cell* 65, 1043–1051; Harris et al., 1991, *Anal. Biochem.* 193, 191–196; Elsbach et al., 1979, *J. Biol. Chem.* 254, 11000–11009. Briefly, in one example, *E. coli* microorganisms, labeled with $^3$H-fatty acids, are incubated with a phospholipase A₂ enzyme. The reaction is terminated with tetrahydrofuran and the released labeled free fatty acids are separated over an aminopropyl column by elution with tetrahydrofuran:acetic acid (49:1). The sample is counted by liquid scintillation spectroscopy and the percent of free fatty acids determined to measure enzyme activity.

The present invention also includes a test kit to identify a compound capable of inhibiting phospholipase A₂ activity of a parasitic helminth. Such a test kit includes an isolated parasitic helminth PLA2 protein having phospholipase A₂ activity and a means for determining the extent of inhibition of phospholipase A₂ activity in the presence of (i.e., effected by) a putative inhibitory compound. Such compounds are also screened to identify those that are substantially not toxic in host animals.

Phospholipase A₂ inhibitors isolated by such a method, and/or test kit, can be used to inhibit any phospholipase A₂ that is susceptible to such an inhibitor. Preferred phospholipase A₂ enzymes to inhibit are those produced by parasitic helminths. A particularly preferred phospholipase A₂ inhibitor of the present invention is capable of protecting an animal from heartworm, onchocerciasis or filariasis. It is also within the scope of the present invention to use inhibitors of the present invention to target phospholipase A₂-related disorders in animals. Therapeutic compositions comprising phospholipase A₂ inhibitory compounds of the present invention can be administered to animals in an effective manner to protect animals from disease caused by the targeted phospholipase A₂ enzymes, and preferably to protect humans from onchocerciasis. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle.

The following examples are provided for the purposes of illustration and are not intended to limit the scope of the present invention.

EXAMPLES

The following examples include a number of recombinant DNA and protein chemistry techniques known to those skilled in the art; see, for example, Sambrook et al., ibid.

Example 1

This Example describes a procedure for producing and evaluating immune sera of the present invention.

Four dogs were immunized with chemically-abbreviated *D. immitis* larval infections (using the method described in Grieve et al., 1988, *Am. J. Trop. Med. Hyg.* 39, 373–379), and two dogs served as chemically-treated controls. The dogs were housed in indoor mosquito-free individual cages at a temperature of about 22° C. and about 40% to about 65% humidity. On day 532, post initial immunization, each dog was challenged with about 100 L3 *D. immitis* larvae by implanting 5 diffusion chambers per dog, each diffusion chamber containing about 20 L3 *D. immitis* larvae, using the method described in Grieve et al., 1988, ibid. Concomitant with chamber implantation, each dog was injected subcutaneously with about 50 L3 *D. immitis* larvae, and the infection was allowed to proceed beyond the anticipated pre-patent period. Challenge infections were repeated on day 588, post initial immunization, both by implanting 5 diffusion chambers per dog, each chamber having about 20 L3 *D. immitis* larvae and by subcutaneously inoculating about 30 L3 *D. immitis* larvae per dog. Serum samples were collected from the immunized dogs at numerous time points throughout the study period. Serum samples were analyzed for antibodies that selectively bound to L3 and/or L4 surface antigens using an indirect fluorescent antibody assay, and for antibodies that selectively bound to L3 soluble antigens, L4 soluble antigens and/or to an excretory/secretory antigen fraction using an indirect ELISA, as described by Grieve et al., 1988, ibid. The results indicated that serum from dogs that had been immunized and challenged with *D. immitis* larvae had produced antibodies to both surface and soluble *D. immitis* larval antigens. The sera were pooled, and those obtained from larval-immunized dogs (i.e., anti-larval immune sera) were shown to inhibit larval development; see, for example, Example 2. Immune sera were also shown to selectively bind to L3 and/or L4 larval proteins having molecular weights of about 15 kD, 23/24 kD doublet, 31 kD, 33 kD, 39 kD, 42 kD, 55 kD, 59 kD, 66 kD, 70 kD, 97 kD and 207 kD by Tris-glycine SDS PAGE.

Example 2

This Example demonstrates that serum collected from larval-immunized dogs, produced as described in Example 1, is capable of inhibiting parasite development whereas serum collected from non-immunized dogs is not.

One subcutaneous pocket was formed in each of about 3 to about 6 Balb/C BYJ mice that were about 10 weeks old. One diffusion chamber, containing 20 L3 *D. immitis* larvae, was implanted into each pocket alone with 0.5 ml of sera collected from immunized dogs or from non-immunized dogs, produced as described in Example 1. The diffusion chambers were recovered two or three weeks later. Living larvae in the chambers were counted and placed into glacial acetic acid, followed by 70% ethanol containing 5% glycerin. The ethanol was allowed to evaporate leaving the larvae in glycerin. The larvae were measured us ing projected images in the Macmeasure image analysis system on a Macintosh computer.

Three experiments, in which different serum samples were exposed to larvae in diffusion chambers, were conducted: Experiment 1 compared equal portions of sera collected from individual dogs at days 56, 77 and 117 after challenge. Experiments 2 and 3 compared serum collected from immunized dogs 117 days after initial challenge to control sera. In experiment 2, the control serum was a pool of sera collected from 12 naive dogs; in experiment 3, control serum was collected from a single naive dog. Each of the experiments also included controls in which the larvae were not exposed to any serum.

In experiment 1, chambers were recovered two weeks post-inoculation. The number of larvae retrieved from chambers implanted in mice receiving serum from immunized (i.e., immune) dogs was lower than that of larvae in chambers implanted in mice receiving naive dog serum, but the difference was not statistically significant. Also, no differences were seen between the length of larvae regardless of which serum was used.

In experiments 2 and 3, the chambers were recovered three weeks after infection. There were significant differences in the larval recoveries between those receiving serum from naive dogs and those from immune dogs; there were about 34% more larvae recovered from mice treated with naive dog serum than were recovered from mice treated with immune serum. The lengths of the larvae were also significantly shorter in those chambers exposed to sera from immune dogs compared to larvae in chambers exposed to naive dog sera. Thus, this Example shows that serum collected from dogs immune to *D. immitis* infection inhibits larval development, compared to serum collected from naive dogs.

Example 3

This Example describes the identification of antigens that selectively bind to serum from a dog that is immune to heartworm infection.

Crude extracts of L4 larvae were prepared as follows: All procedures were performed at 4° C. or on ice. L4 worms were collected and washed twice with wash buffer (PBS/ 0.1% Triton X-100) and then with extraction buffer (0.05 M Tris/HCl, pH 6.8; 2% CHAPSO; 1 mM PMSF; 1 mM EDTA; 1 mg/l leupeptin; 1 mg/l pepstatin). (Other detergents may be used in place of CHAPSO, including 0.5% Triton X-100, 0.5% CTAB, 2% DOC, or 2% SDS/5% 2-ME/8 M urea.) The worms were then homogenized 5 times for 1 minute each, with 1 minute rest periods, using 250 $\mu$l to 500 $\mu$l of extraction buffer for 10,000–20,000 worms (~500 $\mu$g). This volume was transferred to an additional tube, and the homogenizer washed with a clean 100 $\mu$l to 250 $\mu$l of extraction buffer and the wash pooled with the homogenate. The tube was rocked from 4 hours to overnight and centrifuged at 12,000 g for 10 minutes. The supernatant was harvested and the pellet washed once with extraction buffer and saved for additional extractions if desired. The combined total volume of extract was less than 1 ml and about 20 ng of protein was solubilized per L4 larva used.

Crude extracts of L3 were prepared in the same manner, except that the wash buffer was PBS without detergent.

The extracts were subjected to polyacrylamide gel electrophoresis and tested with portions of the serum shown to be protective in the murine model. When pooled canine sera which had been shown to stunt larval growth as described in Example 2 were used as the immunoreactant in the Western blots, the results were as shown in FIG. 1. The 39 kD band shown in FIG. 1 is separated from a 45 kD band when a second dimension is added to the electrophoresis. This 45 kD protein is not immunoreactive. As seen, the serum is specifically immunoreactive with a 39 kD protein present in the L4 larval stage. This protein has a pI of about 5. Control serum shows no immunoreactivity with this protein. Reactivity to the 39 kD molecule is present in immune dogs, but not in control dogs. Sera from dogs with microfilaremic infection or amicrofilaremic infection do not recognize this molecule.

In addition, bands were present at 66 kD, 24/23 kD, and 14 kD, as shown in FIG. 2.

The proteins associated with the larval stages were also metabolically labeled using S-35 methionine; or the surfaces were labeled, prior to extraction, with I-125 or with biotin. For labeling with S-35 methionine, the radiolabeled amino acid was added to the parasites after 48 hrs in culture according to the method of Abraham et al., 1987, *J. Parasitol.* 73, 377–383. For labeling with I-125, the method of Mok et al., 1988, *Molec. Biochem. Parasitol.* 31, 173–182 was used. For biotinylation, a modification of the method of Alvarez et al., 1989, *Molec. Biochem. Parasitol.* 33, 183–190, was employed. In the modified procedure, NHS-long chain biotin was substituted for biotin per se.

Figure 4B:
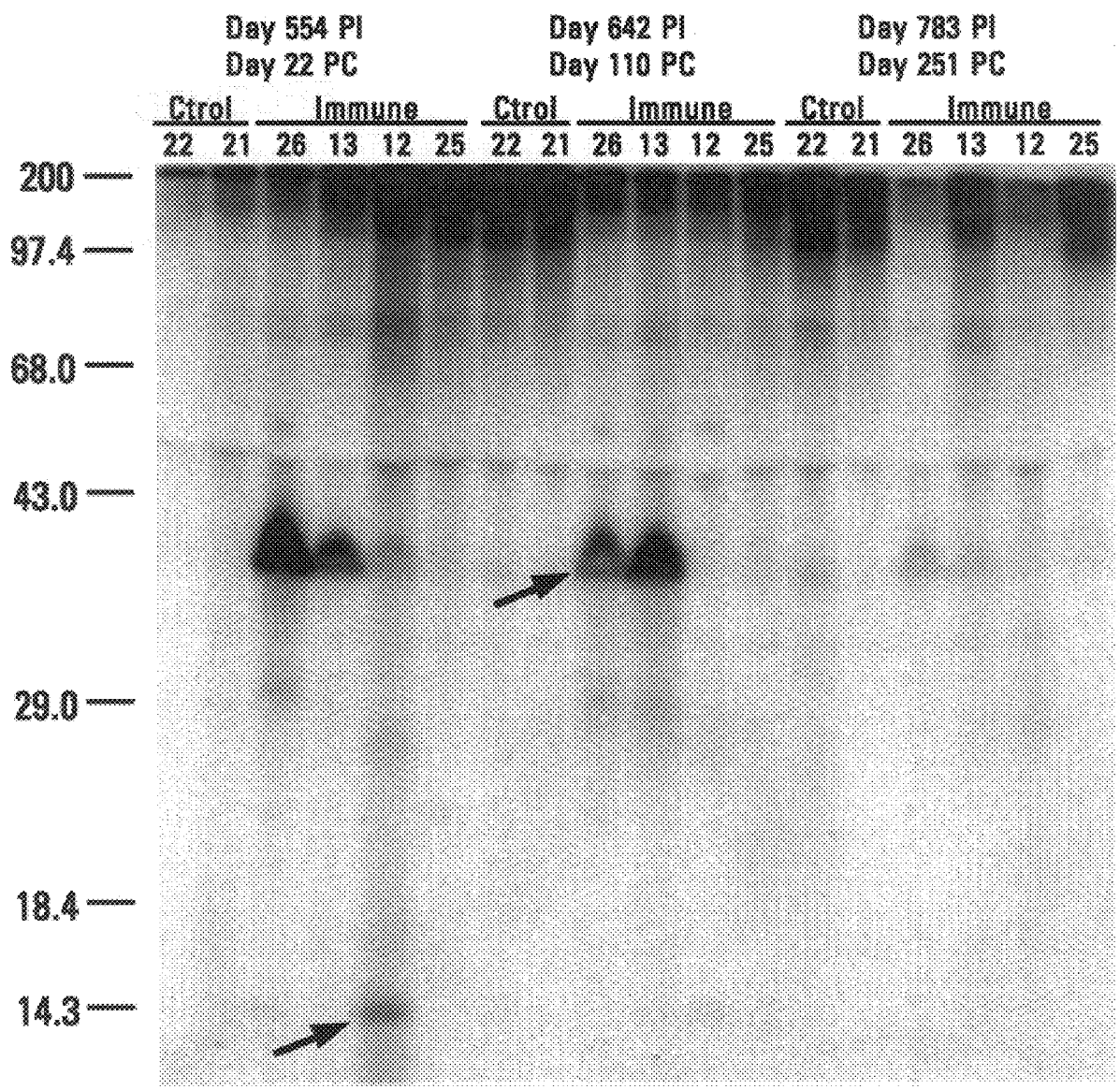
Figure 5A:
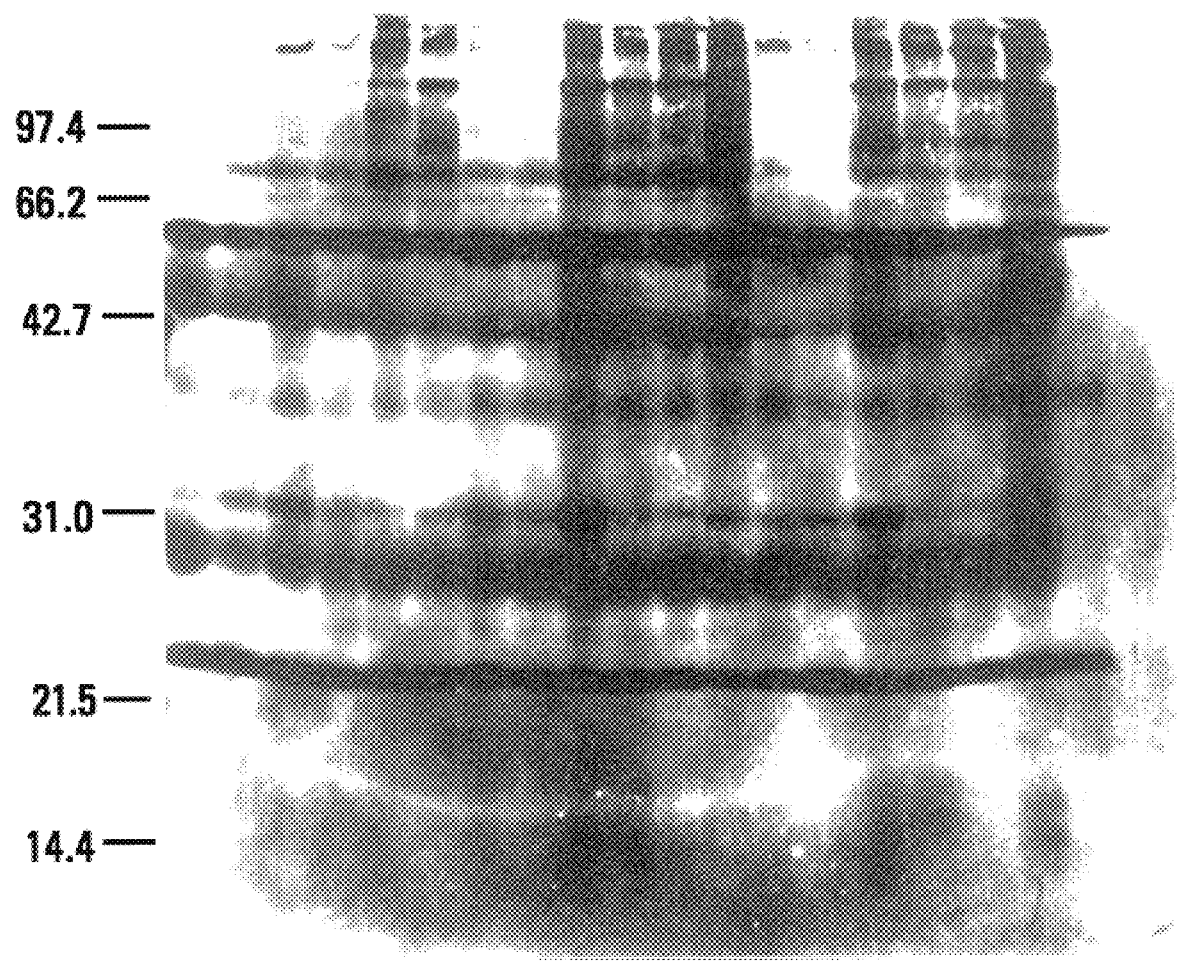
FIGS. 5A–B shows the results of proteins analyzed as in FIG. 3, but wherein the larval surface proteins are labeled using biotin.
Figure 5B:
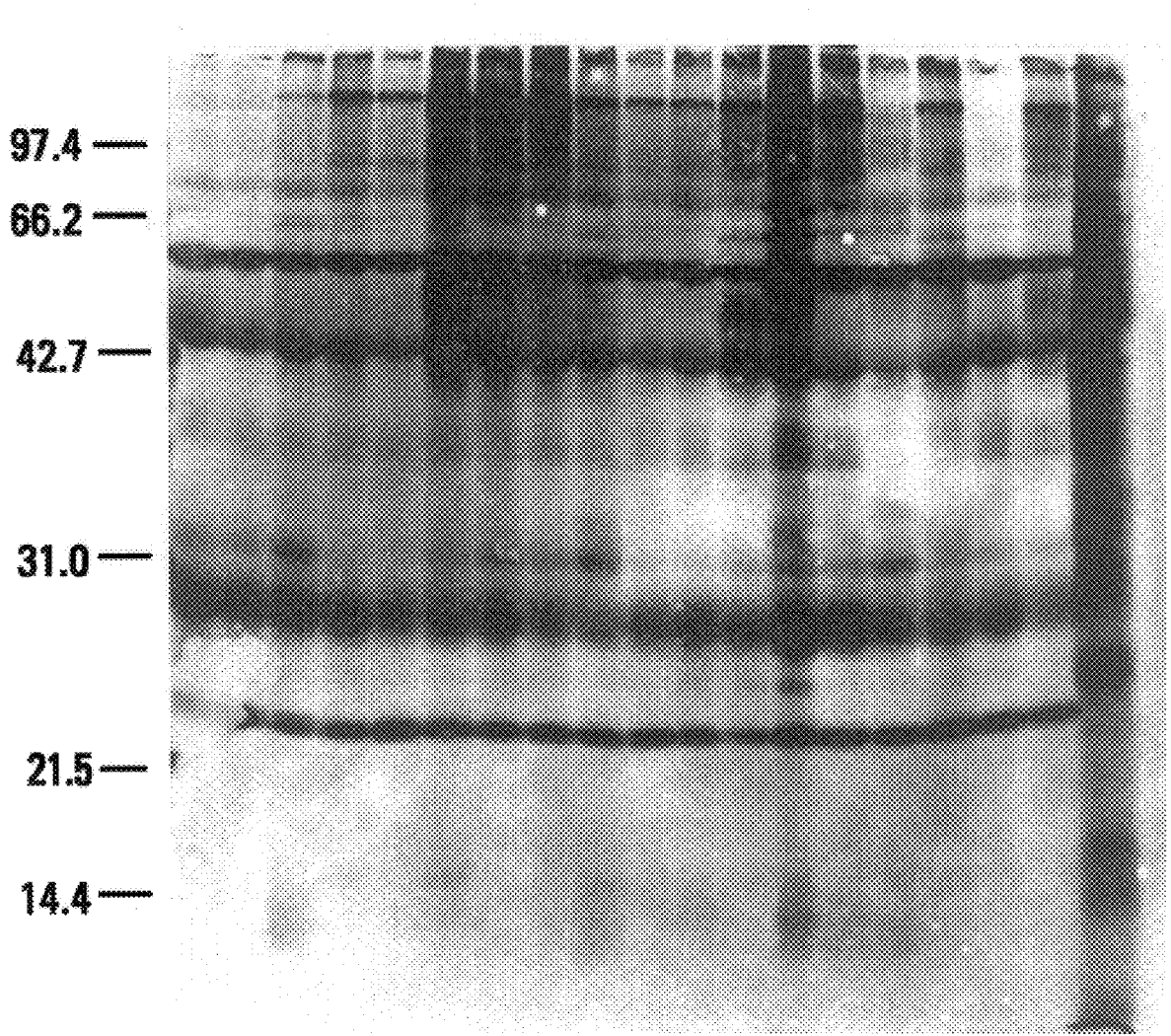

Thus, additional identification could be had using these prelabeled proteins which immunoprecipitated with the successfully validated immune serum. These results are shown in FIGS. 3, 4 and 5. As shown in FIG. 3, additional candidates are found at 59 kD and 16 kD, as indicated by the arrows. The radioactive iodine-labeled material shows a candidate at about 33 kD with a higher molecular weight smear at 35.8–34.5 kD. This was present beginning at day 345 and persisting until day 642 in some, but not all, immune dogs. An additional band was present at 14.5 kD. This is indicated in FIG. 4.

FIG. 5 shows the results when the proteins were labeled by biotinylation in an enhanced chemiluminescence assay. A transient band represented by 65.3 kD was recognized by 3 of 4 immune dogs.

In addition, passive transfer of the earliest immune dog serum which showed uniform responses to the 39 kD protein (i.e., the day-142 immune serum shown in FIG. 3) was able to effect killing of the entrapped larvae; recoveries of intact larvae were only 58.3% in the case of immune serum compared to 65.8% for controls.

To summarize, the following antigen candidates were obtained:

A 39 kD protein which reacted with sera from all immune dogs but not with sera from naive cohorts. The protein is shown to be present in Western blots obtained from L4 soluble antigen and solubilized L4 larval pellets and is shown to be present, although apparently to a lesser degree, in L3. This protein appears to be absent from adult *D. immitis* and the microfilariae. It is clearly a distinct protein from the p35 protein described by Scott et al., ibid., and P39 is relatively acidic, having a pI of approximately 5.

A 14 kD immunogen is detected with immune dog serum using Western blots and immunoprecipitation employing S-35 and iodine-labeled components. The protein is detected with immune dog serum, but not by serum from controls.

Additional proteins detected are of 66 kD and 23/24 kD.

Figure 6:
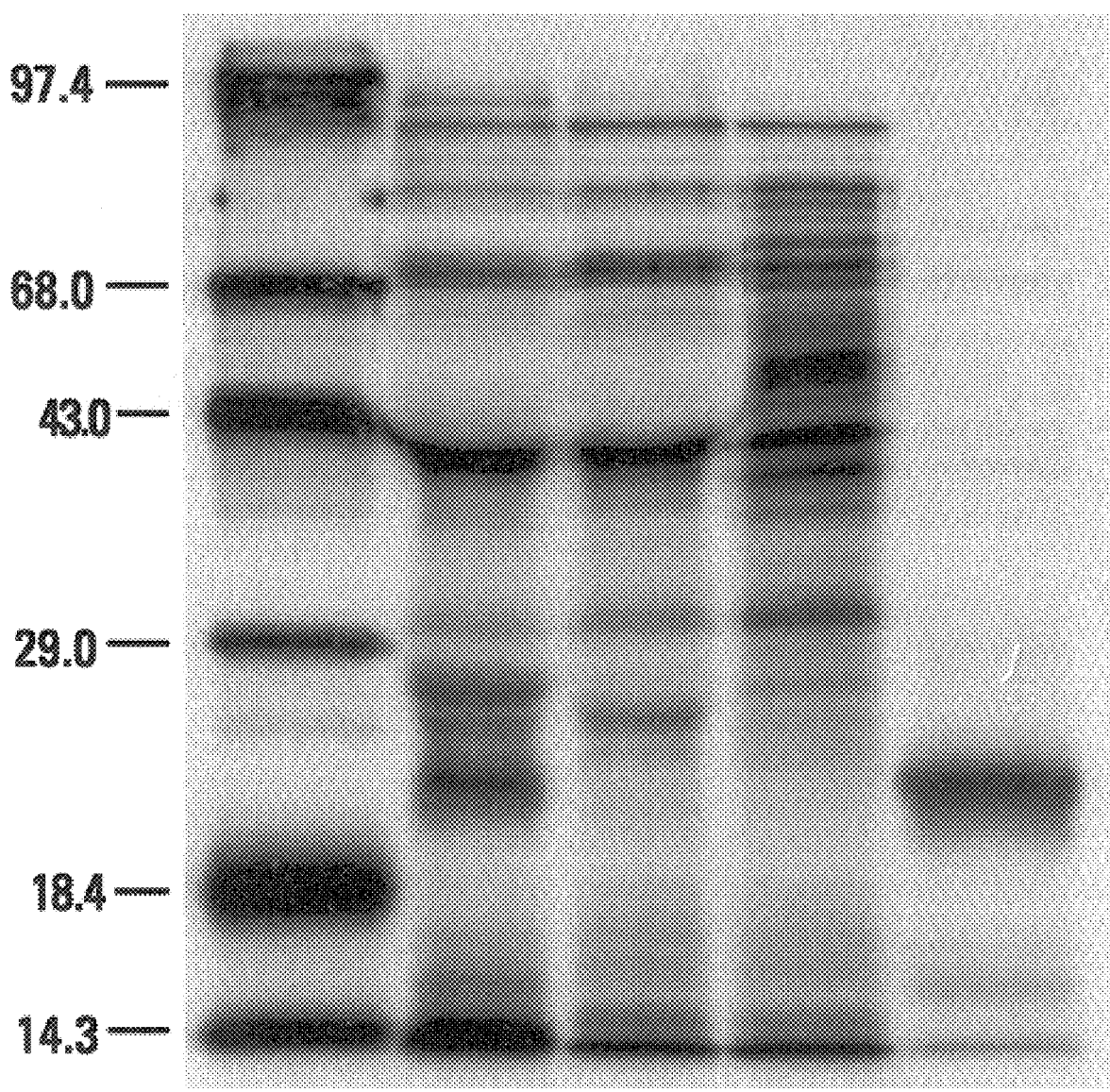
FIG. 6 shows the results of analysis of proteins present in the excretory/secretory material which characterizes the transition from L3 to L4 and maintenance of L4s for 3–4 days thereafter.

Another potential source of protective antigens in parasitic diseases are excretory/secretory products which are associated with various stages of the parasite. The transition between L3 and L4 involves excretion/secretion of a number of proteins which were harvested as follows: Larvae were cultured at 250–400/ml, washed at 48 hr and cultured an additional 4 days. The worms were then settled out and the supernatant collected. The supernatant was filtered through a 0.45 μm filter and protease inhibitors added as in L4 solubilization. The ES was then concentrated and buffer exchanged by ultrafiltration over a 10 kD membrane (Amicon Centriprep-10 and/or Centricon-10). The final buffer was 0.05 M Tris/HCl pH 6.8 with protease inhibitors. Yields may be about 5 ng of protein per larva, frequently in a final volume of 150 μl to 250 μl. This extract, referred to as DILEX, was prepared using larvae which were metabolically labeled with S-35 methionine and tested with respect to immune and control sera from dogs. The immune serum was that obtained on day 554 post immunization as set forth in Example 1. Immunoprecipitation with respect to the immune serum was obtained at 22/20.5 kD and 14.3 kD, as shown in FIG. 6. In FIG. 6, lane 1 shows molecular weight standards; lane 2, the immunoprecipitates from immune dog; lane 3, from control dog; lane 4, bead control; and lane 5, DILEX itself.

Example 4

This Example describes the purification of *D. immitis* P22U, P22L and P20.5 as well as tryptic digestion of the proteins, and partial amino acid sequencing of several tryptic fragments.

Larvae and ES proteins were pulse chase labeled as described by Frank et al., 1992, *J. Parasitol.* 77, 950–956. Proteins of 22 and 20.5 kD were shown to be developmentally regulated proteins that were particularly present in L3 and L4.

Third stage larvae were collected and cultured in vitro as described in Frank et al., ibid. The larvae were washed free of serum proteins at about 48 hr, placed back into culture and the serum-free media containing larval ES products was collected from 48 to 144 hr in culture. Each week's yield of ES was collected, filtered through a 0.45 μm filter (Acrodisc™, Gelman Sciences, Ann Arbor, Mich.) and frozen at about −70° C. until further processing. Processing was conducted at about 4° C. or on ice and consisted of thawing the ES and adding 0.5 M EDTA·$Na_2$, pH 8.0, to a final concentration of 5 mM. EDTA was the only protease inhibitor used since only metalloprotease activity has been found in larval ES (Richer et al., 1992, *Exp. Parasit.* 75, 213–222). The ES was concentrated and the buffer was exchanged using Centriprep-10 and Centricon-10 (Amicon, Beverly, Mass.); the final buffer was 20 mM Tris, 1 mM EDTA·$Na_2$, pH 7.2.

All chromatography was performed on a Beckman 338 binary system using System Gold version 3.10 chromatography software (Beckman Instruments, Inc., San Ramon, Calif.). The separations and fraction collections were conducted at room temperature and the fractions placed at about 4° C. immediately after each run. When portions of the samples were metabolically labeled, aliquots of the collected fractions were assayed in scintillation fluid by a Beckman Model LS 1801 liquid scintillation counter (Beckman Instruments, Inc.).

Figure 7:
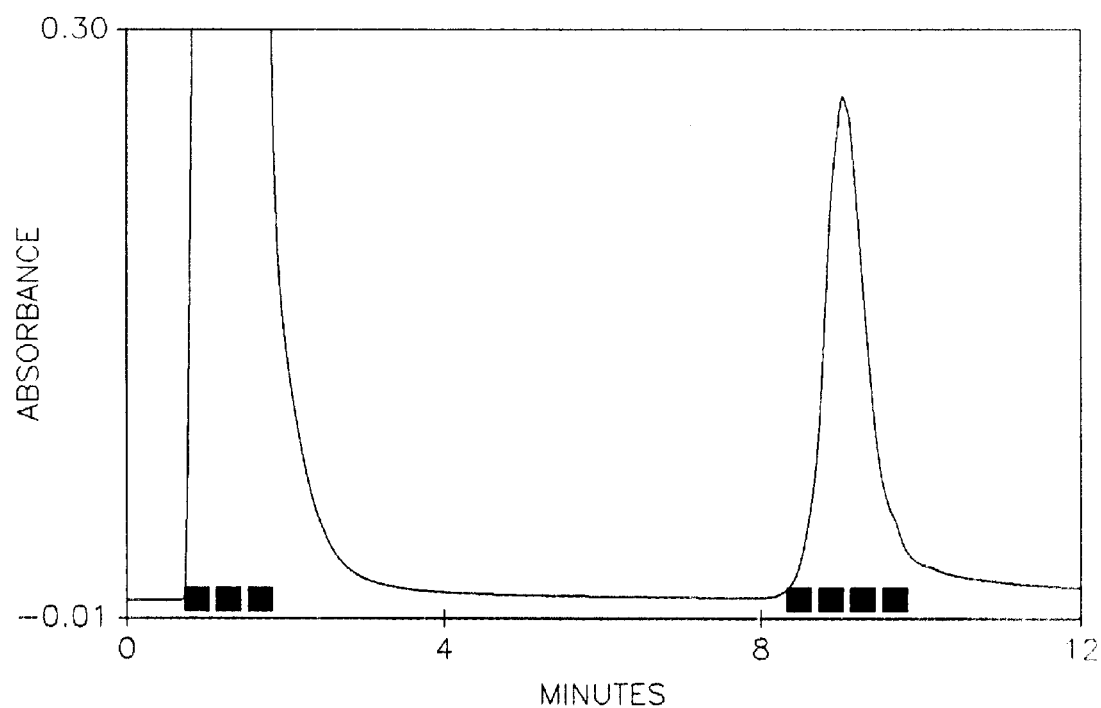
FIG. 7 depicts a chromatogram of the separation of larval ES by cation exchange chromatography.

The first purification was from approximately 38,650 larvae, 3,550 of which had been metabolically labeled with Translabel™ from about 48 to 144 hr. The ES products were concentrated to 175 μl in 20 mM Tris, 1 mM EDTA·$Na_2$, pH 7.2 (Buffer A) and contained 1.3 μg/μl protein with an 35S-incorporation of 7,450 cpm/μl. Cation exchange chromatography was used as the first step in purification. A SynChropak CM300-GRD 4.6×50 mm column (Synchrom, Inc., Lafayette, Ind.) was used. The sample was diluted with 300 μl buffer A, centrifuged at 12,000 g and the supernate injected onto the column at 0.5 ml/min Buffer A. After a 5 min wash, the adsorbed proteins were eluted with a steep gradient to 100% Buffer B (1 M KCl in Buffer A) over 0.1 min while 200 μl fractions were collected throughout. Detection of proteins was at 280 nm. FIG. 7 shows the resultant chromatogram. Boxed fractions, designated 4, 5, 6, 23, 24, 25 and 26, were evaluated by SDS PAGE.

The vast majority of contaminating proteins eluted in the initial peak. In contrast, P22U, as well as P22L and P20.5, eluted in the second peak, i.e., in fractions 23, 24, 25 and 26.

Reverse phase chromatography using a Vydac $C_4$ 0.21×25 cm, 5 μm particle size column (Vydac 214TP52, The Separations Group, Hesperia, Calif.) was used to separate P22U from P22L and P20.5. Buffer C consisted of 0.1% trifluoroacetic acid (TFA), 0.085% triethylamine (TEA) in Milli-Q water produced by processing 18 megaohm water through a Milli-Q Plus water system (Millipore Corp., Bedford, MA), while Buffer D consisted of 0.085% TFA, 0.085% TEA, 80% $CH_3CN$ in Milli-Q water. Detection of proteins was at 220 nm. Fractions 23 and 24 from the cation exchange run were injected onto the column followed by fractions 25 and 26 two min later. The initial flow rate was 0.25 ml/min at 12.5% D, 87.5% C. The flow rate was reduced to 0.17 ml/min at 4 min and a gradient to 62.5% D over 200 min was started at 6 min. Fractions of 0.75 min were collected.

Aliquots of peak fractions were subjected to SDS-PAGE and analyzed by silver staining and autoradiography. P20.5 appeared first and predominated in fractions 99–102 (elution times of from about 74.25 minutes through about 76.5 minutes). P22L predominated in fractions 103–107 (elution times of from about 77.25 minutes through about 80.25 minutes), although there was significant contamination with P20.5. P22U eluted much later, in fractions 229–235 (elution times of from about 171.75 minutes through about 176.25 minutes). P22U, P22L and P20.5 recovered from C4 reverse phase chromatography were each shown by immunoblot analysis (see, for example Grieve et al., 1992, *J. Immunol.* 148, 2511–2515 for method), using dog immune serum prepared as in Example 1, to be uniquely recognized by the immune serum.

The molecular weights of P22U, P22L and P20.5 were determined using Tris-tricine SDS-PAGE according to the method of Schagger et al., 1987, *Analyt. Biochem.* 166, 368–379. This Tris-tricine system has been reported to give more accurate estimates of molecular weights for other proteins; see, for example, Patton et al., 1991, *Analyt. Biochem.* 197, 25–33. Molecular weight standards used were SDS-PAGE Standards, Low Range (Bio-Rad Laboratories) and MW-SDS-17S (Sigma Chemical Co., St. Louis, Mo.). The 20 and 22L kD proteins resolved as 16.1 and 18.8 kD by reducing Tris-tricine SDS-PAGE. This same sample electrophoresed on 1) a second Tris-tricine gel resulted in molecular weights of 15.3 and 17.7 kD, and 2) a Tris-glycine gel resulted in molecular weights of 21.9 and 23.2 kD.

Fractions containing P22L and P20.5 obtained from $C_4$ reverse phase chromatography were subjected to $C_{18}$ reverse phase chromatography using a 0.21×25 cm, 5 μm particle size column (Vydac 218TP52) to try to separate the two proteins further. The flow rate was 0.2 ml/min at 11.1% Buffer F (0.085% TFA, 90% $CH_3CN$ in Milli-Q water), 88.9% Buffer E (0.1% TFA in Milli-Q water) with a gradient to 83.3% Buffer F over 65 min. One minute fractions were collected from 3 through 83 min. P20.5 eluted first, followed by P22L.

A sample of purified P22U obtained from $C_4$ reverse phase chromatography as well as samples of purified P22L and P20.5 obtained from $C_{18}$ reverse phase chromatography were denatured, reduced and pyridylethylated by standard procedures; see, for example, Matsudaira (ed.), 1989, *A Practical Guide to Protein and Peptide Purification for Microsequencing*. The pyridylethylated P22U, P22L and P20.5 samples were each subjected to trypsin digestion, and the tryptic peptides separated by $C_{18}$ reverse phase chromatography using a 0.21-cm×25-cm, 5μm particle size column (Vydac 218TP52) by a procedure based on Stone et al., 1989, in Matsudaira (ed.), *A Practical Guide to Protein and Peptide Purification for Microsequencing*, p. 31–47.

Figure 8A:
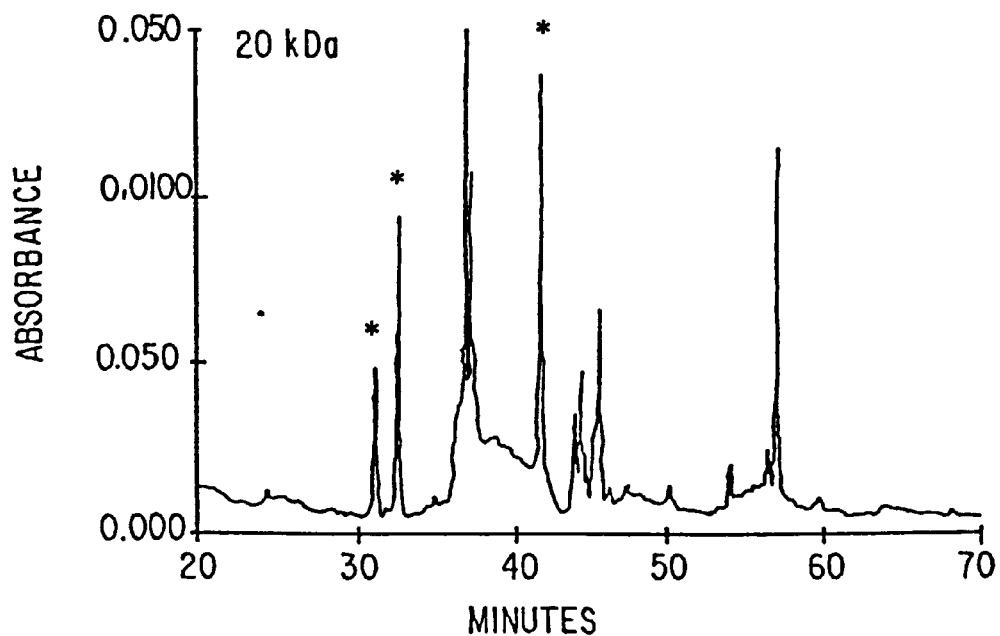
FIG. 8 depicts a chromatogram of the separation of tryptic fragments of P22U by $C_{18}$ reverse phase chromatography; P22U was purified by cation exchange and $C_4$ reverse phase chromatography.
Figure 8B:
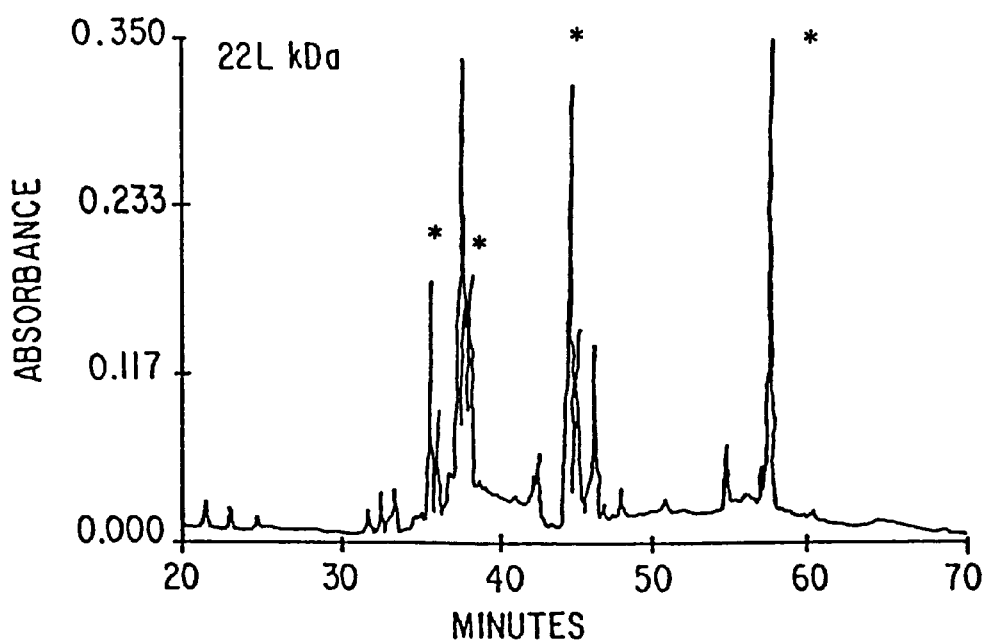
Figure 8C:
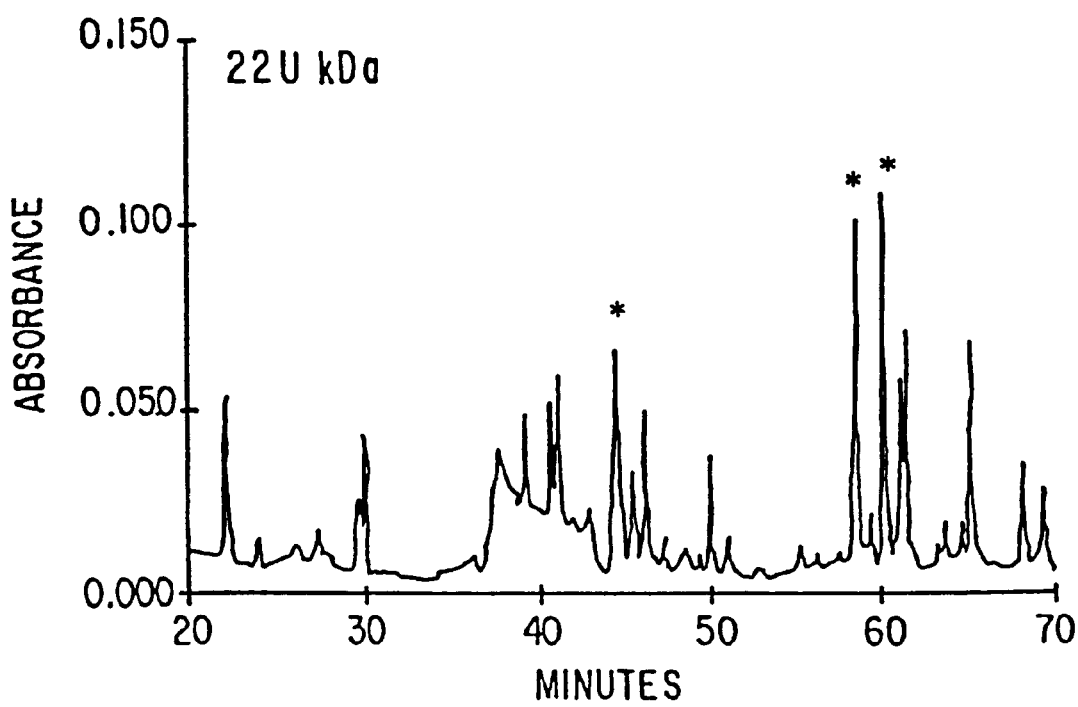

Chromatograms depicting the tryptic fragments of P20.5, P22L and P22U are shown in FIG. 8, labelled, respectively as "20 kDa", "22L kDa" and "22U kDa". As seen from FIG. 8, the tryptic map of P22U is completely different from those of P22L and P20.5, which share at least some fragments in common.

Fragments indicated by asterisks were subjected for sequencing. All sequencing was conducted at Macromolecular Resources, Department of Biochemistry, Colorado State University, Fort Collins, Colo. The peptides were concentrated to 50 μl or less using a Speedvac® and frozen at about −20° C. until sequencing. N-terminal sequencing was conducted in an ABI Model 473A Protein/Peptide Sequencer System (Applied Biosystems, Inc., Foster City, Calif.) using pulsed liquid chemistry and on line microgradient PTH amino acid analysis (see, for example, Hewick et. al., 1981, *J. Biol. Chem.* 256, 7990–7997; Geisow et al., 1989, in Findlay et al. (ed.), *Protein Sequencing: A Practical Approach*, p. 85–98).

N-terminal amino acid sequencing of electroblotted P22L and P20.5 was conducted as originally described by Matsudaira, 1987, *J. Biol. Chem.* 262, 10035–10038, and outlined by LeGendre et al., 1989, in Matsudaira (ed.), *A Practical Guide to Protein and Peptide Purification for Microsequencing*, p. 49–69. P20.5 yielded sequence while P22L and P22U were determined to be N-terminally blocked.

The most likely (i.e., consensus) sequence of the P22U tryptic fragment eluting at 44 minutes (referred to as the 44 min P22U tryptic fragment), using one-letter amino acid code, was M A Q D A F P N A C A Q G E P K (SEQ ID NO:21). Derived sequences for this fragment were M A Q D/P A/G F/E P/R N/K A C/G A Q G E P K (SEQ ID NO:22). Although the observed heterogeneity (for this and other tryptic fragments) may be, at least in part, due to amino acid sequencing technology, such heterogeneity may also represent the existence of allelic variants, since the sample that was sequenced comprised P22U purified from a population of *D. immitis* worms. The most likely sequence of the P22U tryptic fragment eluting at 58 minutes (referred to as the 58 min P22U tryptic fragment) was A I A P C Q L T A V Q S V L P C A D Q C Q K (SEQ ID NO:23). The most likely sequence of the P22U tryptic fragment eluting at 60 minutes (referred to as the 60 min P22U tryptic fragment) was L G S C S P D C G L D L P S D N V M V Q D V (SEQ ID NO:24). Derived sequences for this fragment were L G/M S C/V S/D P/R D C G L D/W L/W P/R S D/W N V M/W V/S Q D/W V/S (SEQ ID NO:25).

The most likely sequence of the P22L tryptic fragment eluting at 35 minutes (referred to as the 35 min P22L tryptic fragment) was H V E T H E A C Y D Q R (SEQ ID NO:26). Derived sequences for this fragment were H/M V E/G T/S H/I E/G A C/M Y D Q R (SEQ ID NO:27). The derived sequence of the P22L tryptic fragment eluting at 38 minutes (referred to as the 38 min P22L tryptic fragment) was G E F V E S D G K (SEQ ID NO:28). The derived sequence of the P22L tryptic fragment eluting at 44 minutes (referred to as the 44 min P22L tryptic fragment) was N-W Q C S Y D, where "-" is any amino acid. The most likely sequence of the P22L tryptic fragment eluting at 58 minutes (referred to as the 58 min P22L tryptic fragment) was E P Q S W C I L K P H Q S-T Q R (SEQ ID NO:30). Derived sequences for this fragment were E P Q S W/A C I L K P H Q S-T/W Q/D R (SEQ ID NO:31).

The most likely sequence of the N-terminus of P20.5 was E T Q E E T V-F E E-D-D (SEQ ID NO:32). Derived sequences for this fragment were E/P T Q E E T V-F E E-D-D (SEQ ID NO:33). The derived sequence of the P20.5 tryptic fragment eluting at 31 minutes (referred to as the 31 min P20.5 tryptic fragment) was F V E S D G K (SEQ ID NO:34). The derived sequence of the P20.5 tryptic fragment eluting at 32 minutes (referred to as the 32 min P20.5 tryptic fragment) was T-E A C Y D Q R (SEQ ID NO:35). The most likely sequence of the P20.5 tryptic fragment eluting at 42 minutes (referred to as the 42 min P20.5 tryptic fragment) was F N W Q C S Y D (SEQ ID NO:36). Derived sequences for this fragment were F N/M W/L Q C S Y D (SEQ ID NO:37).

Example 5

This Example describes the cloning and sequencing of *D. immitis* nucleic acid molecules of the present invention, including nDiPLA2$_{586}$, nDiPLA2$_{450}$ (also referred to as np22L) and nDiPLA2$_{387}$ (also referred to as p20.5).

Oligomeric DNA primers and probes were made by DNA Express, Department of Biochemistry, Colorado State University. Synthesis was done using an ABI model 392 DNA/RNA synthesizer using cyano-ethyl-phosphoramidite chemistry. Products were purified using low pressure reverse phase chromatography. Nucleic acid oligonucleotide probes were 3'-end labeled by tailing with ($^{32}$P)-deoxycytidine as described by Collins et al., 1985, Analyt. Biochem. 151, 211–224. Terminal deoxynucleotidyl transferase (available from Promega Corp.) was used according to manufacturers instructions.

D. immitis L3 larvae were harvested from mosquitos using standard techniques and cultivated in vitro in 50:50 NCTC-135/IMDM (NI) media (Sigma) supplemented with 20% serum supplement at 37° C., 5% carbon dioxide for 48 hours. Total RNA was extracted from the larvae using an acid-guanidinium-phenol-chloroform method similar to that described by Chomczynski et al., 1987, Anal. Biochem. 162, 156–159. Approximately 15,000 to 30,000 larvae were used in an RNA preparation. Poly A+ selected RNA was separated from total RNA by oligo-dT cellulose chromatography using oligo dT cellulose from Collaborative Research, Inc., Waltham, Mass., according to the method recommended by the manufacturer.

A D. immitis L3 larval cDNA expression library was constructed in lambda (λ) Uni-ZAP™ XR vector (available from Stratagene Cloning Systems, La Jolla, Calif.) using Stratagene's ZAP-cDNA Synthesis Kit® protocol and about 5 µg to about 6 µg of L3 poly A+. The resultant library was amplified to a titer of about 4.88×10$^9$ pfu/ml with about 97% recombinants. Library plating and plaque lifts were essentially done according to manufacturer's instructions (Stratagene) using XL1-Blue Escherichia coli; see also Sambrook et al., ibid.

Plaques lifted onto Nytran 0.45 µm 137 mm membranes (available from Schleicher and Schuell, Keene, N.H.) were hybridized under stringent conditions (see Sambrook et al., ibid.) with about 5 pmoles of labeled GRF6 probe (approximately 1.5×10$^6$ cpm/ml). This probe was synthesized based on the amino acid sequence EACYDQ (SEQ ID NO:38) obtained from the 32 and 35 min tryptic peptides of the P20.5 and P22L proteins, respectively, described and shown in Example 4. The DNA sequence of GRF6 was 5' GAAGCITGCTATGATCAA 3' (SEQ ID NO:39), where I is inosine which is capable of base pairing with all four bases. The wobble base selection for glutamic acid (E), cysteine (C), tyrosine (Y), aspartic acid (D) and glutamine (Q) was based on codon usage for two D. immitis proteins previously reported (GenBank accession numbers M29733 and M82811). Of about 102,000 plaques screened, approximately 252 (0.25%) hybridized to the probe. Sixteen plugs containing positive plaques were removed and 5 of these were plaque purified using standard techniques.

Plaque-purified clones including D. immitis PLA2 nucleic acid molecules were converted into double stranded recombinant molecules using R408 helper phage and XL1-Blue E. coli according to the in vivo excision protocol described in the Stratagene ZAP-cDNA Synthesis Kit. Double stranded plasmid DNAs were prepared using an alkaline lysis protocol, such as that described in Sambrook et al., ibid., and subjected to restriction enzyme cleavage by EcoRI and XhoI restriction endonucleases. Insert sizes were estimated to be 334 bp (clone 1), 442 bp (clone 2), 603 bp (clone 3), 589 bp (clone 4) and 442 bp (clone 5), 32 bp of which were vector sequence.

DNA sequencing of the clones was accomplished using the Sanger dideoxy chain termination method, as described in Sambrook et al., ibid. The Promega Erase a Base method (available from Promega Corp., Madison, Wis.) was used to generate deletion clones for sequence analysis. MacVector™ version 3.5 sequence analysis software (International Biotechnologies, Inc., New Haven, Conn.) was used for amino acid translations, protein molecular weight and isoelectric point calculations, and hydrophilicity calculations. Partial DNA sequence was determined for clones 1, 2, 3 and 5 as well as for the untranslated regions of clone 4; and the full double strand sequence of the protein coding region was determined for clone 4.

Clone 4, denoted herein as nDiPLA2$_{586}$, was determined to have the nucleic acid sequence represented herein as SEQ ID NO:1. Translation of SEQ ID NO:1 suggests that nucleic acid molecule nDiPLA2$_{586}$ encodes a full-length D. immitis PLA2 protein of about 150 amino acids, referred to herein as PDiPLA2$_{150}$, assuming an open reading frame having a start codon spanning from about nucleotide 7 through about nucleotide 9 of SEQ ID NO:1 and a stop codon spanning from about nucleotide 457 through about nucleotide 459 of SEQ ID NO:1. This open reading frame, excluding the stop codon, comprises nucleic acid molecule nDiPLA2$_{450}$ of the present invention, the nucleic acid sequence of which is represented herein by SEQ ID NO:3. It is to be noted that the open frame of nDiPLA2$_{586}$ extends an additional 6 nucleotides upstream from the first ATG codon to the beginning of the molecule.

The deduced amino acid sequence of PDiPLA2$_{150}$ is represented herein as SEQ ID NO:2. Analysis of SEQ ID NO:2 suggests that PDiPLA2$_{150}$ includes an amino terminal signal peptide through about amino acid 21 of SEQ ID NO:2. Amino-terminal sequencing of the processed protein reported in Example 4 supports this deduction; see, in particular, SEQ ID NO:32 and SEQ ID NO:33. As such, the present invention also includes a processed protein denoted PDiPLA2$_{129}$, represented by amino acid sequence SEQ ID NO:5, which is encoded by nucleic acid molecule nDiPLA2$_{387}$, the nucleic acid sequence of which is represented herein as SEQ ID NO:4, as well as a signal segment of about 21 amino acids having amino acid sequence SEQ ID NO:7, encoded by nucleic acid molecule nDiPLA2$_{63}$, the nucleic acid sequence of which is represented herein as SEQ ID NO:6.

Figure 9:
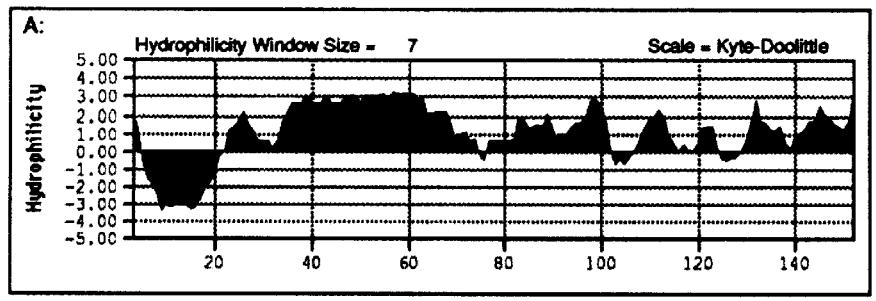
FIG. 9 shows the hydrophilicity plot and protein characteristics calculated for the sequences of the P20.5 (also referred to as 20 kD) and P22L (also referred to as 22L kD) proteins.

FIG. 9A shows a hydrophilicity plot of the amino acid sequences deduced for PDiPLA2$_{150}$ and PDiPLA2$_{129}$. Hydrophilicity was calculated based on the method of Kyte et al., 1982, J. Mol. Biol. 157, 105–132, with a window size of 7 amino acids. Molecular weights, isoelectric points (pI) and amino acid compositions of the entire PDiPLA2$_{150}$ amino acid sequence (FIG. 9B, 22L kD) and the proposed PDiPLA2$_{129}$ cleavage product beginning at the glutamic acid at position 22 (FIG. 9C, 20 kD) are shown.

The protein encoded by nDiPLA2$_{450}$ is very hydrophilic with the exception of the N-terminal 21-amino acid hydrophobic leader that is apparently cleaved from PDiPLA2$_{129}$. The calculated molecular weight of this 21 amino acid segment is 2.2 kD. This relationship between PDiPLA2$_{150}$ and PDiPLA2$_{129}$ explains both the similar chromatographic behavior and the similar immunological reactivity of the two molecules.

PDiPLA2$_{150}$ has a calculated molecular weight of 17,527.7 daltons and a calculated pI of 4.58. PDiPLA2$_{129}$ has a calculated molecular weight of 15,328.1 daltons and a calculated pI of 4.52. These molecular weight calculations differ from those obtained from routine Tris-glycine SDS-PAGE under reducing conditions. The calculated molecular weights are in the range calculated from Tris-tricine SDS-PAGE. The calculated pI's also differ from those originally reported by Frank et al., ibid., which stated that the 22 kD protein was basic and suggested that the 20.5 kD protein might be either basic or acidic. Such confusion is explained by the existence of two proteins migrating at 22 kD in the SDS PAGE systems of Frank et al., ibid., namely P22U and P22L and that P22U, not P22L, is the basic protein, a finding of the invention not appreciated by Frank et al., ibid.

As disclosed above, the approximate C-terminal half of $PDiPLA2_{150}$ (and, as such that of $PDiPLA2_{129}$) is similar in amino acid sequence to a variety of snake and mammalian $PLA_2$ amino acid sequences, the similarities being particularly well conserved with respect to cysteines and the amino acids comprising the active site. A BLAST search of the NCBI non-redundant data library (SWISS-PROT ver. 23.0, PIR ver. 34.0, GenPept CDS translations from GenBank release 73.1) using amino acids 80–104 (i.e., DGKMK HCKTH EACYD QREPQ SWCIL) of amino acid sequence SEQ ID NO:2 yielded 40 records, 39 of which were snake or mammalian $PLA_2$ sequences. Twenty-five of the 29 SWISS-PROT match sequences represent $PLA_2$ venoms from a variety of snakes while the other four sequences were mammalian pancreatic $PLA_2$ sequences. No non-mammal, non-arthropod eukaryotic entries were found. The highest percent identity between the region of $PDiPLA2_{150}$ spanning from about amino acid 80 through about amino acid 104 and known sequences was about 40%. The highest percent identity between the region of $PDiPLA2_{50}$ spanning from about amino acid 85 through about amino acid 102 and known sequences was about 55%. Overall identity between $PDiPLA2_{150}$ and known sequences was significantly less than 30%.

Example 6

This Example discloses Northern blot analysis of D. immitis L3 and L4 RNA using probes corresponding to a portion of D. immitis nucleic acid molecule $nDiPLA2_{586}$.

D. immitis 0-hour L3, 48-hour L3 and 6-day L4 larvae were harvested and total RNA purified therefrom as described in Example 5. Adult female poly A+ RNA was prepared similarly after the worms were ground to a fine powder in liquid nitrogen. RNA was electrophoresed through agarose-formaldehyde gels and transferred to Nytran membranes (available from Schleicher and Schuell) essentially as described by Sambrook et al., ibid. with minor modifications as described in Fourney et al., 1988, Focus 10, 5–6. Samples of about 10 μg of larval total RNAs and about 1.8 μg adult female poly A+ RNA were analyzed. An initial hybridization procedure resulted in excessive non-specific binding of probe which had to be stripped by standard techniques. RNA species immobilized on the membrane were then hybridized for about 52 hours using standard Northern blot conditions to about $5 \times 10^5$ cpm/ml labeled GRF10. GRF10 was an anti-sense oligomeric DNA corresponding to nucleotides 5' CATAGTTCTTGGCT-TAGCGCTTC 3' (SEQ ID NO:40) of $nDiPLA2_{450}$ (spanning about nucleotides 15 through 37 of SEQ ID NO:3). After washing and exposure, a strong signal was seen in the 48-hr L3 lane and a weaker signal was seen in the 6-day L4 lane each corresponding to RNA species of about 720 to about 730 bases. GRF10 essentially did not hybridize to 0-hr L3 or adult female RNA.

Although only 1.8 μg of RNA was loaded in the adult female lane, presumably this contained considerably more message than the 10 μg of larval total RNA per lane due to the poly A+ selection. The finding of a relative abundance of message in 48 hr L3, less in 6 day L4 and none in 0 hr L3, adults and, presumably, microfilariae, substantiates the pulse-chase metabolic labeling patterns described by Frank et al., ibid.

Example 7

This Example demonstrates the ability of a D. immitis nucleic acid molecule of the present invention to encode a protein that, when expressed in bacteria, selectively binds to immune serum. Furthermore, the recombinant protein can induce the production of antibodies in rabbits and dogs capable of recognizing the corresponding native and recombinant heartworm antigens.

Recombinant molecule $pHis-nDiPLA2_{417}$ (also referred to as $pET19b-PLA2_{417}$) containing D. immitis nucleic acid molecule $nDiPLA2_{586}$ nucleotides from about nucleotide 58 through about nucleotide 474 of SEQ ID NO:1 operatively linked to bacteriophage T7lac transcription control sequences and to a fusion sequence encoding a polyhistidine segment comprising 10 histidines was produced in the following manner. An about 417-nucleotide DNA fragment containing nucleotides spanning from about 58 through about 474 of SEQ ID NO:1, called $nDiPLA2_{417}$ (also referred to as $PLA2_{417}$), was PCR amplified from $nDiPLA2_{586}$ using the primers 5' CGCGGATCCTTCCG-CATCAGAATCACAAGAAG 3' (SEQ ID NO:41, denoted 20 NH2; BamHI site in bold) and 5' CGAAGGAATG-GATCCTTATAAGTTATTAATCG 3' (SEQ ID NO:42, denoted 20 COOH'; BamHI site in bold). The PCR product was digested with BamHI restriction endonuclease, gel purified and subcloned into expression vector pET19b (available from Novagen Inc.) that had been cleaved with BamHI. The resulting recombinant molecule $pHis-nDiPLA2_{417}$ was transformed into E. coli BL21(DE3)pLysS to form recombinant cell E. coli:$pHis-nDiPLA2_{417}$. E. coli BL21(DE3)pLysS includes a bacteriophage T7 RNA polymerase gene under the control of lac transcription control sequences.

Recombinant cell E. coli:$pHis-nDiPLA2_{417}$ was cultured in shake flasks containing an enriched bacterial growth medium containing 0.1 mg/ml ampicillin and 0.034 mg/ml chloramphenicol at about 37° C. When the cells reached an optical density at about 600 nanometers ($OD_{600}$) of about 1.0, expression of D. immitis $nDiPLA2_{417}$ was induced by addition of about 1 mM isopropyl-β-D-thiogalactoside (IPTG). Protein production was monitored by SDS PAGE of recombinant cell lysates, followed by Coomassie blue staining, using standard techniques. Recombinant cell E. coli:$pHis-nDiPLA2_{417}$ produced a protein, denoted PHIS-$PDiPLA2_{132}$ (also referred to as PHIS-$PLA2_{417}$), that migrated with an apparent molecular weight of about 26 kD. Such a protein was not produced by cells transformed with the pET-19b plasmid lacking a D. immitis DNA insert.

Immunoblot analysis of recombinant cell E. coli:$pHis-nDiPLA2_{417}$ lysates indicated that the 26 kD protein was able to selectively bind to immune dog serum and, as such, was capable of binding to at least one component of a serum that is capable of inhibiting D. immitis larval development.

The E. coli-produced PHIS-$PDiPLA2_{132}$ histidine fusion peptide was separated from soluble E. coli proteins by nickel chelation chromatography and an imidazole gradient. Immunoblot analysis of the total E. coli:$pHis-nDiPLA2_{417}$ lysate, column eluate and column void volume indicated that the PHIS-$PDiPLA2_{132}$ 26 kD protein can be isolated on the nickel column and was able to selectively bind to immune dog serum, and as such, was capable of binding to at least one component of a serum that is capable of inhibiting *D. immitis* larval development. The column eluate was not detected by preimmune sera from the same immune dog.

A rabbit was immunized twice with PHIS-PDiPLA2$_{132}$ that was purified by chelation chromatography followed by C4 reverse phase chromatography. Antisera collected from this rabbit, denoted anti-PHIS-PDiPLA2$_{132}$ antisera, was used to characterize the protein in the larvae.

Immunoblot analysis was performed on 1500 microfilaria, 150 each of 7-day mosquito derived L2 from malpighian tubules, 10-day mosquito derived L3 from heads, 15-day mosquito derived L3 from heads, 0-hr in vitro cultured L3 harvested at 25° C., 0-hr in vitro cultured L3 harvested at 37° C., 48-hr in vitro cultured L3, 6-day in vitro cultured L4, 10-day in vitro cultured L4, 13-day in vitro cultured L4, 3 $\mu$g adult male antigen and 3 $\mu$g adult female antigen. Immunoreactivity to *D. immitis* PLA2 protein (as detected using anti-PHIS-PDiPLA2$_{132}$ antisera) was found in all L3 and L4 samples examined, but was not detected in microfilaria, L2 or adult males or females. Processing from the 22 kD form (i.e., PDiPLA2$_{150}$) to the 20.5 kD form (i.e., PDiPLA2$_{129}$) was also observed. The 22 kD form appeared in the L3 as early as 10 days in the mosquito, and remained as such until harvested for in vitro culture at day 15 in the mosquito. The 20 kD form was found as early as 48 hours after removal from the mosquito. Upon subsequent in vitro incubation, the 22 kD form gradually diminished until it was barely evident by 13 days in culture, while the 20.5 kD form was still clearly evident.

Immunoblot analysis, using anti-PHIS-PDiPLA2$_{132}$ antisera, was performed on both PDiPLA2$_{150}$ and PDiPLA2$_{129}$ purified from *D. immitis* larval excretory-secretory products demonstrating both were immunologically recognized.

Two dogs were immunized three times with PHIS-PDiPLA2$_{132}$ that was purified by chelation chromatography. Antisera collected from the dogs recognized both PDiPLA2$_{150}$ and PDiPLA2$_{129}$ in 48-hr L3 *D. immitis*.

Example 8

This example demonstrates the production of a *D. immitis* PLA2 protein of the present invention (i.e., PDiPLA2$_{150}$ as well as PDiPLA2$_{129}$) in eukaryotic cells as well as the production of a recombinant virus vaccine capable of expressing a *D. immitis* PLA2 protein capable of selectively binding to immune serum.

A PCR product of about 475 nucleotides containing from about nucleotide 1 to about nucleotide 475 of SEQ ID NO:1 was generated from a recombinant molecule including nDiPLA2$_{586}$ similar to that described in Example 5 using primers 76–40.B having the nucleic acid sequence 5' GCGGGATCCAACATGAACAAACTTTTCATAGTTC 3' (SEQ ID NO:43) and 20COOH (i.e., SEQ ID NO:42; see Example 7), each of which have BamHI sites (in bold) incorporated into the primers. The BamHI-digested nDiPLA2$_{475}$ (also referred to as p22L$_{475}$) PCR product was subcloned into a BamHI-digested, CIP treated pSP64 vector (available from Promega) to form the vector p76-52.H3. Proper insert orientation was verified.

For subcloning into the baculovirus shuttle plasmid Blue-BacIII (available from InVitrogen, Corp., San Diego, Calif.), the p76-52.H3 plasmid DNA was digested with BamHI and the nDiPLA2$_{475}$ insert DNA was subcloned into the unique BamHI site of BlueBacIII. The resulting recombinant molecule is denoted pBv-nDiPLA2$_{475}$ (also referred to as p76-79-A6). Insert orientation was verified and pBv-nDiPLA2$_{475}$ plasmid DNA was cotransfected into Sf9 host cells (donated by the Colorado Bioprocessing Center, Fort Collins, Colo.) with linear Baculogold baculovirus DNA (available from Pharmingen, San Diego, Calif.) and insectin cationic liposomes (available from InVitrogen) to form *S. frugiperda*:pBv-nDiPLA2$_{475}$. The resulting recombinant baculovirus is denoted vBV-nDiPLA2$_{475}$ (also denoted 89-11). Western blots using rabbit anti-PHIS-PDiPLA2$_{132}$ antisera produced as described in Example 7 demonstrated that insect cells transfected with recombinant baculovirus vBV-nDiPLA2$_{475}$ expressed and processed the protein encoded by nDiPLA2$_{475}$ and, as such produced both PDiPLA2$_{150}$ (also referred to as P22L$_{475}$ and PLA2$_{475}$) and PDiPLA2$_{129}$. Both PDiPLA2$_{150}$ and PDiPLA2$_{129}$ were identified in whole cell lysates, but only PDiPLA2$_{129}$ was detectable as being secreted into the cell culture medium. This result indicated that the secretory signal of *D. immitis* PDiPLA2$_{150}$ is recognized by insect cells and that the molecule is processed naturally in this system.

For subcloning into the Sindbis virus shuttle plasmid Toto2J1, p76-52.H3 DNA was digested with BamHI to release the nDiPLA2$_{475}$ insert DNA which was subcloned into the unique BamHI site of pSP64-XhoI vector to form recombinant molecule pSP-nDiPLA2$_{475}$ (also referred to as p75-79.C2); proper 5' to 3' orientation of the insert within the recombinant molecule was verified. The pSP64-XhoI vector was produced by adding an XhoI restriction site to a pSP64 vector (available from Promega) by linearizing pSP64 with SmaI, ligating an XhoI linker to one end, and recircularizing the vector with T4 ligase.

Recombinant molecule pSP-nDiPLA2$_{475}$ was digested with XbaI and XhoI to release the nDIPLA2$_{475}$ insert which was directionally subcloned into the XbaI-XhoI sites of the Sindbis virus shuttle plasmid Toto2J1 to form recombinant molecule pSv-nDiPLA2$_{475}$ (also referred to as p88-36.1B). Toto2J1 is a Sindbis virus expression vector that contains the SP6 RNA polymerase promoter and the entire Sindbis virus genome through to the NsiI restriction site at nucleotide 11452 (i.e., each of the nonstructural polypeptide genes, the subgenomic promoter, and each of the structural polypeptide genes) ligated to an SspI (nucleotide position 7499)/SstI restriction fragment from TRCAT62 which contains the subgenomic promoter, 14 nucleotides of the 5' untranslated sequence of the subgenomic mRNA, the CAT gene, 62 nucleotides of Sindbis virus 3' untranslated sequence, and the Sindbis virus poly-A sequence (see Xiong et al., 1989, *Science* 243, 1188–1191).

Recombinant molecule pSv-nDiPLA2$_{475}$ was linearized at a unique MluI site. Infectious recombinant Sindbis transcripts generated with SP6 RNA Polymerase and used to infect BHK (baby hamster kidney) host cells as described in Example 11 to produce recombinant cell BHK:pSv-nDiPLA2$_{475}$ (also referred to as BHK:p88-36.1B). The recombinant cell was cultured to produce recombinant virus particle vSV-nDiPLA2$_{475}$ (also referred to as 48-87). Western blot analysis of infected recombinant cell lysates using rabbit anti-PHIS-DiPLA2$_{132}$ antisera produced as described in Example 8 showed that mammalian cells transfected with recombinant Sindbis virus particle vSV-nDiPLA2$_{475}$ expressed the protein encoded by nDiPLA2$_{475}$, namely PDiPLA2$_{150}$ (also referred to as P22L$_{475}$ and PLA2$_{475}$).

Example 9

This Example shows that P22U, but apparently not P22L or P20.5, is expressed in adult heartworms.

Twenty-eight adult female *D. immitis* that had been stored at −70° C. were washed 3 times with PBS, comminuted and homogenized with a glass/teflon homogenizer in 40 mM NaCl, 7.5 mM potassium phosphate pH 6.0, 1 mM EDTA, 1 mM PMSF, 2 mM DTT, 80 μg/ml leupeptin, 80 μg/mi pepstatin and 1 mg/ml TAME. The homogenate was sonicated for a total of 1 min using a 418 probe attached to a W-380 sonicator (available from Heat System-Ultrasonics, Inc., Farmington, N.Y.), centrifuged at 5,000 g for 10 min and the supernatant was collected.

Twenty four adult male *D. immitis* that had been stored at −70° C. were washed 3 times with TBS (50 mM Tris, 150 mM NaCl pH 8.0), frozen in liquid nitrogen and ground to a fine powder with a mortar and pestle. This powder was homogenized in 40 mm NaCl, 20 mm Tris pH 7.2, 1 mM EDTA, 1 mM PMSF, 5 μg/ml leupeptin, 5 μg/ml pepstatin and 1 mg/ml TAME. The homogenate was centrifuged at 10,000 g for 20 min and the supernatant was collected.

The resultant supernatant materials of both male and female worms were further concentrated and the buffer was exchanged to 20 mM Tris, 1 mM EDTA ph 7.2 using Centriprep-10 and Centricon-10 (available from Amicon). All steps described were conducted at 4° C. or on ice.

Similar purification procedures as described for larval ES to prepare proteins for trypsin digestion (e.g., cation exchange followed by reverse phase chromatography as described in Example 3) were conducted on both adult male and female somatic soluble extracts to determine if P22U, P22L or P20.5 could be found in adult heartworms.

A protein consistent with the P22U protein was found following $C_4$ reverse phase chromatography, but neither P22L or P20.5 was seen in the eluates. The eluted protein was subjected to trypsin digestion and the fragments separated as described in Example 3. Tryptic fragment maps of P22U from larval ES, adult female and adult male sources were virtually identical as were the N-terminal sequences of selected tryptic fragments eluting at the same position. It appears, therefore, that P22U is also found in adult *D. immitis*, while there is no clear evidence to suggest the presence of either P22L or P20.5 in adult somatic soluble preparations.

Example 10

This Example discloses the isolation and sequencing of an *Onchocerca volvulus* PLA2 nucleic acid molecule of the present invention.

An *O. volvulus* L3 cDNA expression library (ATCC 37711) constructed in the lambda ZAP® II vector (available from Stratagene) using total L3 RNA was obtained from the American Type Culture Collection (Rockville, Md.). The library had a titer of about $3.0 \times 10^7$ pfu/ml with about 95% recombinants.

An *O. volvulus* PLA2 molecule of about 158 nucleotides, representing a partial *O. volvulus* PLA2 gene and denoted nOvPLA2$_{158}$, was PCR amplified from the *O. volvulus* L3 cDNA expression library using two primers designed from the nucleic acid sequence of the gene encoding *D. immitis* PLA2. The two primers used to obtain *O. volvulus* PLA2 nucleic acid molecule nOvPLA2$_{158}$ from the *O. volvulus* L3 cDNA library included an oligonucleotide having SEQ ID NO:39 (described in Example 5) and an oligonucleotide having SEQ ID NO:42 (described in Example 8).

After amplification, *O. volvulus* nucleic acid molecule nOvPLA2$_{158}$ was gel-purified, electroeluted and cloned into the cloning vector pCRII (available from InVitrogen) following manufacturer's instructions, thereby forming recombinant vector pCRII-nOvPLA2$_{158}$. The nucleotide sequence of nOvPLA2$_{158}$ was determined and found to include nucleotides from about 262 to about 419 of SEQ ID NO:8, the production of which is described in more detail below.

An *O. volvulus* PLA2 nucleic acid molecule of about 557 nucleotides, denoted nOvPLA2$_{557}$, was obtained by screening the *O. volvulus* L3 cDNA expression library with PCR-radiolabeled pCRII-nOvPLA2$_{158}$ DNA as a probe, under stringent (i.e., standard) hybridization conditions as described in Sambrook et al., ibid. The primers used in the amplification of PCR radiolabeled product pCRII-nOvPLA2$_{158}$ were derived from pCRII vector sequences flanking the insert site, including an oligonucleotide having SEQ ID NO:44, namely 5' CGAGCTCGGATCCACTAG 3' (denoted TA+) and an oligonucleotide having SEQ ID NO:45, namely 5' GCATGCTCGAGCGGCCGC 3' (denoted TA−).

Screening of the *O. volvulus* L3 cDNA expression library with PCR-radiolabeled pCRII-nOvPLA2$_{158}$ identified seven positive plaques which were isolated as phage pools. The phage pool having the longest PLA2 cDNA sequence was identified in the following manner. PCR products were amplified from the pools using the following primers: (a) an oligonucleotide derived from the lambda ZAP® II vector sequence that is complementary to a nucleic acid sequence, the 3' end of which is about 14 base pairs (bp) upstream of the EcoRI insert site, the primer having SEQ ID NO:46, namely 5' CGCTCTAGAACTAGTGGATC 3' (denoted SK); and (b) an oligonucleotide having a complementary sequence to nucleotides about 324 through about 347 derived from the sequence of nOvPLA2$_{158}$ (numbers based on SEQ ID NO:8), the primer having SEQ ID NO:47, namely 5' GTGCATTCTCCCTTGGATGAACAG 3' (denoted OvPLA2-1). Four distinct products of approximately 150 bp, 240 bp, 370 bp, and 390 bp were amplified from the seven plaque pools. Individual plaques from the phage pool producing the 390 bp PCR product were rescreened by PCR using SK (SEQ ID NO:46) and OvPLA2-1 (SEQ ID NO:47), and three plaque purified clones were isolated.

The three plaque-purified clones, each of which included *O. volvulus* nucleic acid sequence nOvPLA2$_{557}$ were converted into double-stranded recombinant molecules, using R408 helper phage and XL1-Blue *E. coli* according to the in vivo excision protocol described in the Stratagene ZAP-cDNA® synthesis kit. The recombinant molecules, herein denoted as pβgal-nOvPLA2$_{557}$ are capable of encoding the fusion protein PβGAL-POvPLA2$_{140}$. Double-stranded plasmid DNA was prepared using an alkaline lysis protocol, such as that described in Sambrook et al., ibid.

The *O. volvulus* nucleic acid molecule contained within each of the pβgal-nOvPLA2$_{557}$ recombinant molecules was subjected to nucleic acid sequencing using the Sanger dideoxy chain termination method, as described in Sambrook et al., ibid. Partial sequences of two clones and a full double-stranded sequence including the apparent protein coding region and 5' and 3' untranslated regions of the remaining clone were determined in order to obtain the 557-nucleotide consensus sequence of *O. volvulus* nucleic acid sequence nOvPLA2$_{557}$ presented as SEQ ID NO:8. SEQ ID NO:8 includes a putative translation initiation methionine codon spanning nucleotides from about 4 through about 6, an open reading frame of about 420 nucleotides, and a putative stop codon spanning nucleotides from about 424 through about 426. SEQ ID NO:8 apparently encodes a protein of about 140 amino acids, the amino acid sequence of which is presented in SEQ ID NO:9. The protein comprising SEQ ID NO:9, denoted POvPLA2$_{140}$, has a calculated molecular weight of about 15,842 daltons and an estimated isoelectric point (pI) of about 3.96. A hydrophilicity plot of the amino acid sequence deduced for POvPLA2$_{140}$ (calculated based on the method of Kyte et al., 1982, *J. Mol. Biol.* 157, 105–132) indicates that the protein encoded by POvPLA2$_{140}$ is very hydrophilic with the exception of the N-terminal approximately 20-amino acid hydrophobic leader.

Analysis of SEQ ID NO:9 suggests that POvPLA2$_{140}$ includes an amino terminal signal peptide through about amino acid 22 of SEQ ID NO:9. As such, the present invention also includes a processed protein denoted POvPLA2$_{118}$, represented by amino acid sequence SEQ ID NO:12, which is encoded by nucleic acid molecule nOvPLA2$_{354}$, the nucleic acid sequence of which is represented herein as SEQ ID NO:11, as well as a signal segment of about 22 amino acids, denoted POvPLA2$_{22}$ having amino acid sequence SEQ ID NO:14, encoded by nucleic acid molecule nOvPLA2$_{66}$, the nucleic acid sequence of which is represented herein as SEQ ID NO:13.

A homology search comparing the amino acid sequence of POvPLA2$_{140}$ to the non-redundant protein sequence database was performed through the National Center for Biotechnology Information using the BLAST network. This database includes SwissProt+PIR+SPUpdate+GenPept+GpUpdate. The amino acid sequence containing amino acids about 77 to about 115 of SEQ ID NO:9 was about 33% identical (i.e., homologous) to bovine phospholipase A2 precursor (phosphatidylcholine 2-acylhydrolase) (SwissProt data base accession number P00593); about 30% identical to sheep phospholipase A2 (phosphatidylcholine 2-acylhydrolase) (SwissProt data base accession number P14419); and about 30% identical to pig phospholipase A2, minor isoenzyme (phosphatidylcholine 2-acylhydrolase) (SwissProt data base accession number P04416). SEQ ID NO:9 spanning amino acids about 75 to about 115 was about 31% identical to human phospholipase A2 precursor (phosphatidylcholine 2-acylhydrolase) (SwissProt data base accession number P04054); and about 27% identical to canine phospholipase A2 precursor (phosphatidylcholine 2-acylhydrolase) (SwissProt data base accession number P06596).

SEQ ID NO:9 spanning amino acids about 62 to about 140 exhibited certain regions of homology with the following proteins: an average of about 37% identity with three regions (the three regions including a total of about 57 amino acids) of the phospholipase A2 homolog of the textilotoxin chain A of the Eastern brown snake (SwissProt data bank accession number P23026); an average of about 59% identity with two regions (the two regions including a total of about 22 amino acids) of the phospholipase A2 precursor of the blue-ringed sea krait, *Laticauda laticaudata,* (SwissProt data base accession number P19000); and an average of about 39% identity with three regions (the three regions including a total of about 44 amino acids) of the phospholipase A2 homolog of taipoxin beta chain of the Australian snake taipan, *Oxyuranus scutellatus scutellatus,* (SwissProt data base accession number P00615).

The coding region of the about 140-amino acid *O. volvulus* PLA2 protein POvPLA2$_{140}$ also exhibited significant homology to the coding region of the about 150-amino acid *D. immitis* PLA2 protein PDiPLA2$_{150}$ as do the nucleic acid molecules encoding those proteins. The nucleic acid molecules encoding POvPLA2$_{140}$ and PDiPLA2$_{150}$ were about 61% identical, including about 58% identity in the coding region and about 70% identity in the 3' untranslated region.

OvPLA2$_{140}$ and PDiPLA2$_{150}$ are about 44% identical throughout the entire translated region, with most of the homology (i.e., about 60% identity) occurring in the C-terminal half of the molecule. The C-terminal 80 amino acids of the two proteins also exhibited strict conservation of 8 cysteine residues and conservation of the histidine residue at position 80 (as numbered in SEQ ID NO:9), reported to be the active site in other phospholipase A2 molecules. Both *O. volvulus* and *D. immitis* PLA2 proteins are highly hydrophilic, with the exception of the N-terminal approximately 20- to 22-amino acid highly hydrophobic leader sequences. The *O. volvulus* PLA2 amino acid sequence has a potential glycosylation site from about amino acid 134 to 136 (NWT in SEQ ID NO:9) not found in the *D. immitis* PLA2 sequence (corresponding amino acids being NWQ).

Example 11

This Example discloses the production of a recombinant cell of the present invention capable of producing an Onchocerca PLA2 protein of the present invention.

Recombinant molecule pHis-nOvPLA2$_{542}$, containing an *O. volvulus* PLA2 nucleic acid molecule spanning nucleotides from about 16 through about 557 of SEQ ID NO:8 operatively linked to a trc transcription control sequence and to a fusion sequence encoding a poly-histidine segment comprising 6 histidines, was produced in the following manner. A DNA fragment containing nucleotides spanning from about 16 through about 557 of SEQ ID NO:8, called nOvPLA2$_{542}$, in addition to 11 nucleotides of the recombinant vector, was produced by digesting pβgal-nOvPLA2$_{557}$ with ApoI restriction endonuclease and gel purifying the resultant about 553-bp fragment. The purified fragment was subcloned into expression vector pTrcHisB (available from InVitrogen) that had been cleaved with EcoRI. The resulting recombinant molecule, denoted pHis-nOvPLA2$_{542}$, was transformed into *E. coli* HB101 to form recombinant cell *E. coli*:pHis-nOvPLA2$_{542}$.

Example 12

This Example discloses the production of an *O. volvulus* PLA2 protein of the present invention by a recombinant cell of the present invention.

Recombinant cell *E. coli*:pHis-nOvPLA2$_{542}$, produced as described in Example 11, was cultured in shake flasks containing an enriched bacterial growth medium containing about 0.1 mg/ml ampicillin at about 37° C. When the cells reached an OD$_{600}$ of about 0.3, expression of *O. volvulus* nOvPLA2$_{542}$ was induced by addition of about 1 mM isopropyl-β-D-thiogalactoside (IPTG), and the cells cultured for about 3 hours at about 37° C. Protein production was monitored by SDS-PAGE of recombinant cell lysates, followed by Coomassie blue staining, using standard techniques. Recombinant cell *E. coli*:pHis-nOvPLA2$_{542}$ produced a fusion protein, denoted herein as PHIS-POvPLA2$_{136}$, that migrated with an apparent molecular weight of about 31 kD. Such a protein was not produced by cells transformed with the pTrcHisB plasmid lacking an *O. volvulus* nucleic acid molecule insert.

Immunoblot analysis of recombinant cell *E. coli*:pHis-nOvPLA2$_{542}$ lysates indicated that the about 31 kD protein was able to bind to a T7 tag monoclonal antibody (available from Novagen, Inc., Madison, Wis.) directed against the fusion portion of the recombinant PHIS-POvPLA2$_{136}$ fusion protein.

Example 13

This Example discloses the production of another recombinant *O. volvulus* PLA2 protein of the present invention.

Recombinant molecule pHis-nOvPLA2$_{496}$, containing an O. volvulus PLA2 nucleic acid molecule spanning nucleotides from about 62 through about 557 of SEQ ID NO:8 operatively linked to a trc transcription control sequence and to a fusion sequence encoding a poly-histidine segment comprising 6 histidines, was produced in the following manner. The recombinant molecule pHis-nOvPLA2$_{542}$, produced as described in Example 9, was digested with DraIII and BamHI restriction endonucleases. The digestion product was gel purified, blunt-ended with T4 DNA Polymerase and blunt-end ligated with T4 DNA Ligase. The resulting recombinant molecule, denoted pHis-nOvPLA2$_{496}$, was transformed into E. coli HB101 to form recombinant cell E. coli:pHis-nOvPLA2$_{496}$.

Recombinant cell E. coli:pHis-nOvPLA2$_{496}$ was cultured in shake flasks and expression of O. volvulus nOvPLA2$_{496}$ was induced by addition of about 1 mM IPTG as described in Example 12. Protein production was monitored by SDS-PAGE of recombinant cell lysates, followed by Coomassie blue staining, using standard techniques. Recombinant cell E. coli:pHis-nOvPLA2$_{496}$ produced a fusion protein, denoted herein as PHIS-POvPLA2$_{120}$, that migrated with an apparent molecular weight of about 28 kD. Such a protein was not produced by cells transformed with the pTrcHisB plasmid lacking an O. volvulus nucleic acid molecule insert.

Immunoblot analysis of recombinant cell E. coli:pHis-nOvPLA2$_{496}$ lysates indicated that the about 28 kD protein was able to bind to a T7 tag monoclonal antibody (available from Novagen Inc.) directed against the fusion portion of the recombinant PHIS-POvPLA2$_{120}$ fusion protein. Rabbit antiserum raised against PHIS-POvPLA2$_{120}$, produced as described in Example 14, also selectively bound to the fusion protein.

Example 14

This Example demonstrates the life stage specificity of O. volvulus PLA2.

Recombinant PHIS-POvPLA2$_{120}$ fusion protein, produced as described in Example 13, was purified from E. coli lysates by nickel chelate and C4 reverse phase column chromatography. To confirm that PHIS-POvPLA2$_{120}$ did indeed include POvPLA2$_{120}$, an internal peptide from the C-terminal half of the protein was generated by Asp-N enzymatic cleavage. Following HPLC purification, the peptide was subjected to amino acid sequencing and shown to indeed be part of POvPLA2$_{120}$.

A rabbit was immunized with PHIS-POvPLA2$_{120}$ to generate monospecific anti-POvPLA2$_{120}$ antiserum. To determine the stage specificity of O. volvulus PLA2, an immunoblot using rabbit anti-POvPLA2$_{120}$ antiserum was performed on the following samples: (a) O. volvulus 0-hour L3 lysate; and (b) Chapso extract of O. volvulus adult worms. The anti-POvPLA2$_{120}$ antiserum reacted intensely with a protein having a molecular mass of about 21 kD (immunoblot of SDS PAGE separation in Tris-glycine), whereas there was no detectable reaction between the antiserum and the adult sample in a similar size range.

To determine cross-species and cross-genus reactivity, an immunoblot using rabbit anti-POvPLA2$_{120}$ antiserum was performed on the following samples: (a) 6-day D. immitis L4 lysate and (b) 0-hour O. lienalis L3 lysate. The anti-POvPLA2$_{120}$ antiserum reacted to some extent with a protein of about 24 kD in the O. lienalis L3 sample, but did not recognize PLA2 in the D. immitis L4 sample.

These results indicate that expression of O. volvulus PLA2 is developmentally regulated similar to that of D. immitis PLA2; i.e., in both nematodes, PLA2 is expressed in L3/L4 but not in adults. The results also indicate, that at least for the antiserum used, O. volvulus PLA2 is not detectably cross-reactive with D. immitis PLA2 and somewhat cross-reactive with O. lienalis PLA2.

Example 15

This Example demonstrates the production of POvPLA2$_{140}$ by a eukaryotic cell, as well as the ability of that cell to remove the signal segment, thereby producing POvPLA2$_{118}$ with the correct N-terminus.

Recombinant molecule pVL1393-nOvPLA2$_{425}$, containing O. volvulus nucleic acid molecule nOvPLA2$_{425}$ operatively linked to baculovirus polyhedron transcription control sequences, was produced in the following manner. An about 425 nucleotide DNA fragment containing nucleotides spanning from about nucleotide 4 through about nucleotide 428 of SEQ ID NO:8, called nOvPLA2$_{425}$, was PCR amplified from recombinant molecule pβgal-nOvPLA2$_{557}$, produced as described in Example 10, using the following primers: sense primer 197-02.A which has nucleic acid sequence 5' CGCGGATCCTATAAATATGACCAC-CAAATTTCTAATAGC (BamHI indicated in bold) that is represented herein as SEQ ID NO:48; and antisense primer 197-02.B, which has nucleic acid sequence 5' GCTCTA-GATATTAATCATATTTGCAGGTCCAG 3' (XbaI site indicated in bold) that is represented herein as SEQ ID NO:49. The PCR product was digested with BamHI and XbaI restriction endonucleases, gel purified and directionally subcloned into baculovirus shuttle plasmid pVL1393 (available from InVitrogen) that had been cleaved with BamHI and XbaI. The resulting recombinant molecule, denoted herein as pVL1393-nOvPLA2$_{425}$, was co-transfected into S. frugiperda Sf9 cells with linear wild type baculovirus DNA (AcMNPV) and insectin cationic liposomes (available from InVitrogen) to form S. frugiperda:pVL1393-nOvPLA2$_{425}$.

The resulting recombinant virus, denoted vBV-nOvPLA2$_{425}$ was cultivated for increased production of recombinant virus and to verify expression of POvPLA2$_{140}$ and POvPLA2$_{118}$. Supernatant was collected and subjected to SDS PAGE and immunoblot analysis. The results indicated that rabbit anti-POvPLA2$_{120}$, produced as described in Example 14, selectively recognized proteins of about 22 kD and about 21 kD in the supernatant sample, namely POvPLA2$_{140}$ and POvPLA2$_{118}$. The amino terminus of the 21 kD protein was determined to be EEDFEE, indicating that insect cells were able to properly process POvPLA2$_{140}$ into POvPLA2$_{118}$.

Example 16

This Example demonstrates the production and use of several naked nucleic acid vaccines of the present invention.

Naked nucleic acid vaccines comprising recombinant molecules pPVXC-nDiPLA2$_{463}$, pPVXRC-nDiPLA2$_{463}$, pPVXC-nOvPLA2$_{430}$ or pPVXRC-nOvPLA2$_{430}$ were produced as follows. Vector pRc/RSV (available from InVitrogen) was cleaved by restriction enzyme PvuII, and the 2963-base pair PvuII fragment gel purified. That fragment was self-ligated to form vector pRc/RSV(Pvu), which contains a Rous Sarcoma Virus (RSV) long terminal repeat, a multiple cloning site, a bovine growth hormone polyadenylation sequence, a bacterial origin of replication and an ampicillin resistance gene.

Expression vector PVXRC was produced by introducing a HindIII fragment containing the cytomegalovirus (CMV) intermediate early promoter and first intron (i.e., Intron A)

into pRc/RSV(Pvu) that had been cleaved by HindIII. Expression vector PVXC was produced by introducing a HindIII/SspI fragment containing the CMV intermediate early promoter and first intron (i.e., Intron A) into pRc/RSV (Pvu) that had been cleaved by HindIII and NruI.

Nucleic acid molecule nDiPLA2$_{463}$, which encodes PDiPLA2$_{150}$, and spans from about nucleotide 7 through about nucleotide 469 of SEQ ID NO:1, was produced by PCR amplification of that molecule from nDiPLA2$_{586}$ using the following primers: oligonucleotide PLApRC5 (sense), having nucleic acid sequence 5' GAATTCGGATCCAGGC-CACCATGAACAAACTTTTCATAG 3', represented herein as SEQ ID NO:50; and oligonucleotide 20COOH (antisense) having SEQ ID NO:42 (described in Example 8). Recombinant molecule pPVXC-nDiPLA2$_{463}$ was produced by ligating nucleic acid molecule nDiPLA2$_{463}$ cleaved by BamHI into PVXC that had been cleaved by BamHI. Similarly, recombinant molecule pPVXRC-nDiPLA2$_{463}$ was produced by ligating nucleic acid molecule nDiPLA2$_{463}$ cleaved by BamHI into PVXRC that had been cleaved by BamHI.

Nucleic acid molecule nOvPLA2$_{430}$, which encodes POvPLA2$_{140}$, and spans from about nucleotide 4 through about nucleotide 433 of SEQ ID NO:8, was produced by PCR amplification of that molecule from nOvPLA2$_{557}$ using the following primers: oligonucleotide OvPLA5 (sense), having nucleic acid sequence 5' GAATTGGATCCGCCAC-CATGACCACCAAATTTCTAATAGC 3', represented herein as SEQ ID NO:51; and oligonucleotide OvPLA3 (antisense), having nucleic acid sequence 5' TTTTGGATC-CAAATTATTAATCATATTTGC 3', represented herein as SEQ ID NO:52. Recombinant molecule pPVXC-nOvPLA2$_{430}$ was produced by ligating nucleic acid molecule nOvPLA2$_{430}$ cleaved by BamHI into PVXC that had been cleaved by BamHI. Similarly, recombinant molecule pPVXRC-nOvPLA2$_{430}$ was produced by ligating nucleic acid molecule nOvPLA2$_{430}$ cleaved by BamHI into PVXRC that had been cleaved by BamHI.

Transfection of naked nucleic acid vaccines comprising recombinant molecules pPVXC-nDiPLA2$_{463}$, pPVXRC-nDiPLA2$_{463}$, pPVXC-nOvPLA2$_{430}$ or pPVXRC-nOvPLA2$_{430}$ was performed by standard procedures. Briefly, six-well polystyrene tissue culture plates were seeded with about 3×10$^5$ cells/well in 2 mls of MEM NEAA Earle's salts (available from Irvine Scientific, Santa Ana Calif.) with 100 mM L-glutamine, 5% FBS (complete growth media). Cells were grown to 80% confluence (about 48 hr). The recombinant molecules to be transfected were purified using Qiagen tips (available from Qiagen Inc., Chatsworth, Calif.) per manufacturer's instructions. Using polystyrene plates, about 2 µg of each recombinant molecule was mixed with about 100 µl OptiMEM (available from Gibco BRL). About 15 µl Lipofectamine (available from Gibco BRL) was mixed with about 100 µl OptiMEM. The Lipofectamine mixture was then added to the recombinant molecule mixture and incubated at room temperature for about 30 min. After incubation, about 800 µl OptiMEM was added and the entire mixture overlaid onto the BHK cells that had been rinsed with OptiMEM. Cells were incubated at 37° C., 5% CO$_2$, 90% relative humidity. The transfection mixture was then removed and replaced with about 2 mls complete growth media.

Transfected cells were incubated at 37° C., 5% CO$_2$, 90% relative humidity for about 24 hr and harvested. The media was removed, the cells washed twice with about 2 mls PBS and scraped off the plate in about 1.5 ml PBS. The cells were pelleted by centrifugation, the PBS removed and the cells frozen.

Immunoblot analysis of cell pellets that were subjected to SDS PAGE was performed by standard procedures. The antisera that were used to monitor expression were rabbit anti-PHIS-PDiPLA2$_{132}$ antisera produced as described in Example 7 and rabbit anti-PHIS-POvPLA2$_{120}$ antiserum produced as described in Example 14. Expression was confirmed for both nDiPLA2$_{463}$ and nOvPLA2$_{430}$ in both PVXC and PVXRC vectors. Processing of the signal peptides appeared to occur, and the proteins of the correct size (i.e., PDiPLA2$_{150}$ and PDiPLA2$_{129}$, or POvPLA2$_{140}$ and POvPLA2$_{118}$) were found both in the cells and secreted into the culture media.

Example 17

This Example demonstrates the use of D. immitis and O. volvulus PLA2 nucleic acid sequences to obtain B. malayi PLA2 nucleic acid molecules of the present invention.

PLA2 nucleic acid molecules were PCR amplified from B. malayi genomic DNA using oligonucleotide primers, the design of which was based on homologous regions in D. immitis and O. volvulus PLA2 nucleic acid sequences. The primers used were: oligonucleotide PLA2-DiOV-1 (sense), having nucleic acid sequence 5' TTGCTATGATCAACGT-GAACC 3', represented herein as SEQ ID NO:53; and oligonucleotide PLA2-DiOv-3 (antisense), having nucleic acid sequence 5' CCAGTTTTYKYSRGGTGAGCART-ACG 3' (Y indicating C or T; K indicating G or T; S indicating C or G; R indicating A or G), represented herein as SEQ ID NO:54. The amplified products, about 255 nucleotides in length, were verified for proper amplification by hybridization under stringent hybridization conditions with oligonucleotide PLA2-DiOv-2 (sense), having nucleic acid sequence 5' ATGGACAMAWAGAGGTTGTTTCTG 3' (W indicating A or T, M indicating A or C), represented herein as SEQ ID NO:55. The about 255-nucleotide amplified products were gel purified, ligated into the vector pCR II and transformed into the E. coli strain DH5a. Plasmid DNA was isolated from the transformants and restricted with EcoRI to obtain DNA fragment inserts of about 242 nucleotides, denoted herein as nBmPLA2(19)$_{242}$, and of about 255 nucleotides, denoted herein as nBmPLA2(25)$_{255}$.

Nucleic acid molecules nBmPLA2(19)$_{242}$ and nBmPLA2 (25)$_{255}$ were sequenced using methods similar to those described in Examples 5 and 10 and were found to include closely related, but distinct, partial B. malayi PLA2 genes. The nucleic acid sequence of nBmPLA2(19)$_{242}$ is represented herein as SEQ ID NO:15 and that of nBmPLA2(25)$_{255}$ is represented herein as SEQ ID NO:18.

Translation of SEQ ID NO:15 indicates that nucleic acid molecule nBmPLA2(19)$_{242}$ includes two coding regions separated by an about 79-nucleotide intron, the coding regions spanning from about nucleotide 2 through about nucleotide 60 and from about nucleotide 140 through about nucleotide 242. A nucleic acid molecule containing a contiguous open reading frame of about 162 nucleotides derived from nBmPLA2(19)$_{242}$ is denoted herein as nBmPLA2(19)$_{163}$, and has nucleic acid sequence SEQ ID NO:16. The nucleic acid sequence of nucleic acid molecule nBmPLA2 (19)$_{163}$ is about 78% identical with the corresponding region of nDiPLA2$_{586}$ (spanning from about nucleotide 300 through about nucleotide 415 of SEQ ID NO:1) and about 60% identical with the corresponding region of nOv-PLA2$_{557}$ (spanning from about nucleotide 270 through about 382 nucleotide of SEQ ID NO:8).

Translation of SEQ ID NO:16, beginning at about nucleotide 2, indicates that nBmPLA2(19)$_{163}$ encodes a protein of about 54 amino acids, denoted herein as PBmPLA2(19)$_{54}$, the amino acid sequence of which is represented herein as SEQ ID NO:17. The amino acid sequence of PBmPLA2 (19)$_{54}$ is about 66% identical with the corresponding region of PDiPLA2$_{150}$ (spanning from about amino acid 99 to about amino acid 136 of SEQ ID NO:2) and about 47% identical with the corresponding region of POvPLA2$_{140}$ (spanning from about amino acid 94 to about amino acid 130 of SEQ ID NO:9). Overall identity between SEQ ID NO:17 and known proteins is less than about 20%.

Translation of nucleic acid sequence SEQ ID NO:18 indicates that nucleic acid molecule nBmPLA2(25)$_{255}$ includes two coding regions separated by an about 92-nucleotide intron, the coding regions spanning from about nucleotide 2 through about nucleotide 60 and from about nucleotide 153 through about nucleotide 255. A nucleic acid molecule containing a contiguous open reading frame of about 162 nucleotides derived from nBmPLA2(25)$_{255}$ is denoted herein as nBmPLA2(25)$_{163}$, and has nucleic acid sequence SEQ ID NO:19. The nucleic acid sequence of nucleic acid molecule nBmPLA2(25)$_{163}$ is about 70% identical with the corresponding region of nDiPLA2$_{586}$ (spanning from about nucleotide 300 through about nucleotide 415 of SEQ ID NO:1) and about 55% identical with the corresponding region of nOvPLA2$_{557}$ (spanning from about nucleotide 270 through about 382 nucleotide of SEQ ID NO:8). The nucleic acid sequences of nBmPLA2(19)$_{242}$ and nBmPLA2(25)$_{255}$ are about 62% identical, whereas the nucleic acid sequences of nBmPLA2(19)$_{163}$ and nBmPLA2(25)$_{163}$ are about 72% identical.

Translation of SEQ ID NO:19, beginning at about nucleotide 2, indicates that nBmPLA2(25)$_{163}$ encodes a protein of about 54 amino acids, denoted herein as PBmPLA2(25)$_{54}$, the amino acid sequence of which is represented herein as SEQ ID NO:20. The amino acid sequence of PBmPLA2(25)$_{54}$ is about 58% identical with the corresponding region of PDiPLA2$_{150}$ (spanning from about amino acid 99 to about amino acid 136 of SEQ ID NO:2) and about 40% identical with the corresponding region of POvPLA2$_{140}$ (spanning from about amino acid 94 to about amino acid 130 of SEQ ID NO:9). The amino acid sequences of PBmPLA2(19)$_{54}$ and of PBmPLA2(25)$_{54}$ are about 68% identical. Overall identity between SEQ ID NO:20 and known proteins is less than about 20%.

Example 18

This Example indicates that a live recombinant virus vaccine expressing a D. immitis PLA2 protein of the present invention can protect cats from heartworm.

A live recombinant feline herpes virus vaccine genetically engineered to produce PDiPLA2$_{150}$ was constructed by inserting a nucleic acid molecule encoding PDiPLA2$_{150}$ into a non-pathogenic gene knock out mutant of feline herpes virus (FHV) such that expression of the protein was under the control of the cytomegalovirus immediate early promoter. The resultant recombinant virus is denoted herein as vFHV-nDIPLA2$_{450}$. A control virus was also constructed in which FHV was genetically-engineered in a similar manner to produce a recombinant live FHV vaccine that produced E. coli β-galactosidase (denoted herein as vFHV-βgal).

The ability of cats administered a recombinant virus vaccine of the present invention to be protected from heartworm was determined in the following manner. A test group of 16 cats were administered live recombinant virus vaccine vFHV-nDIPLA2$_{450}$. A first control group of 16 cats were administered live recombinant control virus vFHV-βgal. A second control group of sixteen cats was untreated. Cats in the first control group were administered vFHV-βgal on the same days as the test cats were administered vFHV-nDIPLA2$_{450}$. The immunization dose was about 1×10$^6$ plaque forming units per cat. After immunization, all cats, including both groups of control cats were challenged with 40 L3 D. immitis larvae and subsequently necropsied. The testing schedule is shown below:

| Event | Day |
|---|---|
| Immunization 1 | Day 0 |
| Immunization 2 | Day 28 |
| challenge (40 L3) | Day 83 |
| Necropsy | Day 252 |

An ELISA was performed to evaluate the humoral response to PDiPLA2 after immunization and after challenge. Baculovirus-expressed PDiPLA2$_{129}$ (produced as described in Example 8) was purified from SF-9 cell culture supernatants by anion exchange chromatography followed by reverse phase chromatography. The absorbances obtained at a 1:400 sera dilution for cats in both the untreated control group and the vFHV-nDiPLA2$_{450}$ group were determined and analyzed by group and sex of cat. All cats immunized with the vFHV-nDiPLA2$_{450}$ vaccine developed an antibody titer to PDiPLA2 after immunization. That antibody response appeared to be boosted after challenge by exposure to PDiPLA2 produced by the larvae. D. immitis appeared to release PDiPLA2 both at the molt from L3 to L4, which occurred about 3 days after challenge (i.e., day 86 in the study) and the molt from L4 to young adult, which occurred about 60 days after challenge (i.e., day 143 of the study). The untreated control group appeared to be primed from the L3 to L4 molt and then boosted at the L4 to young adult molt as evidenced by the rapid rise in titer to PDiPLA2 beginning with the day 161 sera.

A comparison of the extent of infection after challenge in test and control cats, presented in Table 1, indicates that cats administered vFHV-nDIPLA2$_{450}$ had an 81.8% reduction in infection compared to the untreated group. Cats in the first control group administered vFHV-βgal exhibited a 36.3% reduction in infection compared to the untreated control group.

TABLE 1

Infected Cats After Challenge

| Group | Total | Infected | % Infected | % Reduction |
|---|---|---|---|---|
| A (Untreated) | 16 | 11 | 68.8 | — |
| B (FHV/β-gal) | 16 | 7 | 43.8 | 36.3 |
| C (FHV/PLA2) | 16 | 2 | 12.5 | 81.8 |

The differences in infectivity after challenge seen between the vFHV-nDIPLA2$_{450}$-treated cats and the untreated control cats, based on the number of worms found in each group of cats, are statistically significant according to several statistical analyses. Performance of a Kruskal-Wallis non-parametric rank analysis yielded a p value of p=0.019 (H value corrected for ties).

An analysis of variance (ANOVA) using square root transformed worm numbers also indicate statistically significant differences (p=0.0267) in infectivity after challenge between vFHV-nDIPLA2$_{450}$-treated cats and untreated control cats.

The differences in infectivity after challenge seen between the vFHV-nDIPLA2$_{450}$-treated cats, the vFHV-βgal-treated control cats and the untreated control cats, based on the number of worms found in each group of cats, were analyzed with regard to statistical significance by Sheffe's Multiple Comparison using square root transformed worm numbers. The results of this analysis are shown in Table 2.

TABLE 2

| Sheffe's Multiple Comparison | | |
|---|---|---|
| Comparison | Sheffe F-test | Significant at p = 0.03 |
| Untreated control vs. vFHV-βgal | 1.154 | no |
| Untreated control vs. vFHV-nDIPLA2$_{450}$ | 3.920 | yes |
| vFHV-βgal vs. VFHV-nDIPLA2$_{450}$ | 0.821 | no |

These results indicate that a recombinant virus vaccine of the present invention, in this example vFHV-nDIPLA2$_{450}$, protects cats from challenge infection by heartworm larvae. The control vaccine vFHV-βgal also had some effect, perhaps to generally boost the immune response of the cats to make them less susceptible to heartworm infection.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:55 submitted herewith are the same.

The present Sequence Listing includes SEQ ID NOs disclosed during the prosecution of U.S. patent Ser. No. 08/003,257, (abandoned) ibid., as well as SEQ ID NOs disclosed in U.S. patent Ser. No. 08/225,479, (abandoned) ibid. Although at least some of those sequences have different SEQ ID NO's in the present application, they are otherwise identical to the original listings.

```
                         SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
        (A) LENGTH: 586 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 7..459

(xi) SEQUENCE DESCRIPTION: SEQ ID NO:1:

GAAAAA ATG AAC AAA CTT TTC ATA GTT CTT GGC TTA GCG CTT CTT TTT         48
       Met Asn Lys Leu Phe Ile Val Leu Gly Leu Ala Leu Leu Phe
         1               5                  10

GTT GCA TTA CCT TCC GCA TCA GAA TCA CAA GAA GAG ACT GTA TCT TTT        96
Val Ala Leu Pro Ser Ala Ser Glu Ser Gln Glu Glu Thr Val Ser Phe
 15              20                  25                  30

GAA GAA AGC GAC GAA GAT TAT GAA GAC GAT AGT GAA GAT CAA ACA AAA       144
Glu Glu Ser Asp Glu Asp Tyr Glu Asp Asp Ser Glu Asp Gln Thr Lys
                 35                  40                  45

GAA GAG GAA CAT TCA AAA GAG GAA GAT CGT TCA GAA GAA CAC GAC GAT       192
Glu Glu Glu His Ser Lys Glu Glu Asp Arg Ser Glu Glu His Asp Asp
             50                  55                  60

CAT TCA GCT GAA GAC GAT AAA TTT GTA ACT AAA GGA AAA TTT GTT GAA       240
His Ser Ala Glu Asp Asp Lys Phe Val Thr Lys Gly Lys Phe Val Glu
         65                  70                  75

AGT GAC GGC AAG ATG AAG CAT TGC AAA ACC CAT GAA GCT TGC TAT GAT       288
Ser Asp Gly Lys Met Lys His Cys Lys Thr His Glu Ala Cys Tyr Asp
     80                  85                  90

CAA CGT GAA CCA CAA TCG TGG TGC ATA TTA AAA CCG CAT CAG TCA TGG       336
Gln Arg Glu Pro Gln Ser Trp Cys Ile Leu Lys Pro His Gln Ser Trp
 95                 100                 105                 110

ACA CAA AGA GGT TGT TTC TGC GAA TCA AAA AAA CAT GCA TGC GTT ATC       384
Thr Gln Arg Gly Cys Phe Cys Glu Ser Lys Lys His Ala Cys Val Ile
                115                 120                 125
```

```
GAA CGA AAA AGC GGC GAC AAA TTG GAA TAT TCG TAT TGC TCA CCC CGA        432
Glu Arg Lys Ser Gly Asp Lys Leu Glu Tyr Ser Tyr Cys Ser Pro Arg
            130                 135                 140

AAA AAC TGG CAG TGT TCA TAC GAT TAATAACTTA TAATTATCTA TTCCTTCGTA       486
Lys Asn Trp Gln Cys Ser Tyr Asp
            145                 150

ATTTCTTCTT ATTTAGCTCC TTTTAATAAC CAACATTTTA CAATGTTTGT TATGTATTCT      546

GATTTTTCTT AAATACAATC TATTGCAATC TCAAAAAAAA                            586

(2) INFORMATION FOR SEQ ID NO:2:

(i) SEQUENCE CHARACTERISTICS:
         (A) LENGTH: 150 amino acids
         (B) TYPE: amino acid
         (D) TOPOLOGY: linear (ii) MOLECULE TYPE: protein (xi) SEQUENCE DESCRIPTION: SEQ ID NO:2:

Met Asn Lys Leu Phe Ile Val Leu Gly Leu Ala Leu Leu Phe Val Ala
  1               5                  10                  15

Leu Pro Ser Ala Ser Glu Ser Gln Glu Glu Thr Val Ser Phe Glu Glu
                 20                  25                  30

Ser Asp Glu Asp Tyr Glu Asp Ser Glu Asp Gln Thr Lys Glu Glu
             35                  40                  45

Glu His Ser Lys Glu Glu Asp Arg Ser Glu Glu His Asp Asp His Ser
         50                  55                  60

Ala Glu Asp Asp Lys Phe Val Thr Lys Gly Lys Phe Val Glu Ser Asp
 65                  70                  75                  80

Gly Lys Met Lys His Cys Lys Thr His Glu Ala Cys Tyr Asp Gln Arg
                 85                  90                  95

Glu Pro Gln Ser Trp Cys Ile Leu Lys Pro His Gln Ser Trp Thr Gln
             100                 105                 110

Arg Gly Cys Phe Cys Glu Ser Lys His Ala Cys Val Ile Glu Arg
         115                 120                 125

Lys Ser Gly Asp Lys Leu Glu Tyr Ser Tyr Cys Ser Pro Arg Lys Asn
130                 135                 140

Trp Gln Cys Ser Tyr Asp
145                 150

(2) INFORMATION FOR SEQ ID NO:3:

(i) SEQUENCE CHARACTERISTICS:
         (A) LENGTH: 450 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

ATGAACAAAC TTTTCATAGT TCTTGGCTTA GCGCTTCTTT TTGTTGCATT ACCTTCCGCA       60

TCAGAATCAC AAGAAGAGAC TGTATCTTTT GAAGAAAGCG ACGAAGATTA TGAAGACGAT      120

AGTGAAGATC AAACAAAAGA AGAGGAACAT TCAAAGAGG AAGATCGTTC AGAAGAACAC       180

GACGATCATT CAGCTGAAGA CGATAAATTT GTAACTAAAG GAAAATTTGT TGAAAGTGAC      240

GGCAAGATGA AGCATTGCAA AACCCATGAA GCTTGCTATG ATCAACGTGA ACCACAATCG      300

TGGTGCATAT TAAAACCGCA TCAGTCATGG ACACAAAGAG GTTGTTTCTG CGAATCAAAA      360
```

AAACATGCAT GCGTTATCGA ACGAAAAAGC GGCGACAAAT TGGAATATTC GTATTGCTCA        420

CCCCGAAAAA ACTGGCAGTG TTCATACGAT                                         450

(2) INFORMATION FOR SEQ ID NO:4:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..387

(xi) SEQUENCE DESCRIPTION: SEQ ID NO:4:

```
GAA TCA CAA GAA GAG ACT GTA TCT TTT GAA GAA AGC GAC GAA GAT TAT         48
Glu Ser Gln Glu Glu Thr Val Ser Phe Glu Glu Ser Asp Glu Asp Tyr
 1               5                  10                  15

GAA GAC GAT AGT GAA GAT CAA ACA AAA GAA GAG GAA CAT TCA AAA GAG         96
Glu Asp Asp Ser Glu Asp Gln Thr Lys Glu Glu Glu His Ser Lys Glu
             20                  25                  30

GAA GAT CGT TCA GAA GAA CAC GAC GAT CAT TCA GCT GAA GAC GAT AAA        144
Glu Asp Arg Ser Glu Glu His Asp Asp His Ser Ala Glu Asp Asp Lys
         35                  40                  45

TTT GTA ACT AAA GGA AAA TTT GTT GAA AGT GAC GGC AAG ATG AAG CAT        192
Phe Val Thr Lys Gly Lys Phe Val Glu Ser Asp Gly Lys Met Lys His
     50                  55                  60

TGC AAA ACC CAT GAA GCT TGC TAT GAT CAA CGT GAA CCA CAA TCG TGG        240
Cys Lys Thr His Glu Ala Cys Tyr Asp Gln Arg Glu Pro Gln Ser Trp
 65                  70                  75                  80

TGC ATA TTA AAA CCG CAT CAG TCA TGG ACA CAA AGA GGT TGT TTC TGC        288
Cys Ile Leu Lys Pro His Gln Ser Trp Thr Gln Arg Gly Cys Phe Cys
                 85                  90                  95

GAA TCA AAA AAA CAT GCA TGC GTT ATC GAA CGA AAA AGC GGC GAC AAA        336
Glu Ser Lys Lys His Ala Cys Val Ile Glu Arg Lys Ser Gly Asp Lys
            100                 105                 110

TTG GAA TAT TCG TAT TGC TCA CCC CGA AAA AAC TGG CAG TGT TCA TAC        384
Leu Glu Tyr Ser Tyr Cys Ser Pro Arg Lys Asn Trp Gln Cys Ser Tyr
        115                 120                 125

GAT                                                                    387
Asp
```

(2) INFORMATION FOR SEQ ID NO:5:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:5:

```
Glu Ser Gln Glu Glu Thr Val Ser Phe Glu Glu Ser Asp Glu Asp Tyr
 1               5                  10                  15

Glu Asp Asp Ser Glu Asp Gln Thr Lys Glu Glu Glu His Ser Lys Glu
             20                  25                  30

Glu Asp Arg Ser Glu Glu His Asp Asp His Ser Ala Glu Asp Asp Lys
         35                  40                  45

Phe Val Thr Lys Gly Lys Phe Val Glu Ser Asp Gly Lys Met Lys His
```

```
              50                  55                  60
Cys Lys Thr His Glu Ala Cys Tyr Asp Gln Arg Glu Pro Gln Ser Trp
 65                  70                  75                  80

Cys Ile Leu Lys Pro His Gln Ser Trp Thr Gln Arg Gly Cys Phe Cys
                 85                  90                  95

Glu Ser Lys Lys His Ala Cys Val Ile Glu Arg Lys Ser Gly Asp Lys
                100                 105                 110

Leu Glu Tyr Ser Tyr Cys Ser Pro Arg Lys Asn Trp Gln Cys Ser Tyr
            115                 120                 125

Asp (2) INFORMATION FOR SEQ ID NO:6:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..63

(xi) SEQUENCE DESCRIPTION: SEQ ID NO:6:

ATG AAC AAA CTT TTC ATA GTT CTT GGC TTA GCG CTT CTT TTT GTT GCA    48
Met Asn Lys Leu Phe Ile Val Leu Gly Leu Ala Leu Leu Phe Val Ala
 1               5                  10                  15

TTA CCT TCC GCA TCA                                                63
Leu Pro Ser Ala Ser
            20

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:7:

Met Asn Lys Leu Phe Ile Val Leu Gly Leu Ala Leu Leu Phe Val Ala
 1               5                  10                  15

Leu Pro Ser Ala Ser
            20

(2) INFORMATION FOR SEQ ID NO:8:

(i) SEQUENCE CHARACTERISTICS:
        (A) LENGTH: 557 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 4..424

(xi) SEQUENCE DESCRIPTION: SEQ ID NO:8:

AAA ATG ACC ACC AAA TTT CTA ATA GCT TTT GGA TTA GTG ATT CTT CTT    48
    Met Thr Thr Lys Phe Leu Ile Ala Phe Gly Leu Val Ile Leu Leu
     1               5                  10                  15
```

```
TCC ATA CCA CAT TGT GCA GCA GAA GAA GAT TTT GAA GAA GAA GGA GAA        96
Ser Ile Pro His Cys Ala Ala Glu Glu Asp Phe Glu Glu Glu Gly Glu
             20                  25                  30

GGA GAA GAA ATG CCG GAA GAT AAT GAC GAT GCT CAG CCG GAA GAT ATT      144
Gly Glu Glu Met Pro Glu Asp Asn Asp Asp Ala Gln Pro Glu Asp Ile
                 35                  40                  45

GAC GGT GGG GAT GAA GAA GGA GGA AAT GAT GAA AAT GAA GAT GTT CCT      192
Asp Gly Gly Asp Glu Glu Gly Gly Asn Asp Glu Asn Glu Asp Val Pro
         50                  55                  60

CGA GGA TCA TTC GTT AAT AGT ATG GGC ACA AAG AAA CAG TGC AAA GAG      240
Arg Gly Ser Phe Val Asn Ser Met Gly Thr Lys Lys Gln Cys Lys Glu
 65                  70                  75

CAC CCG GAT TGC TAT GAT CAA CGT GAA CCA GGT GAT TGG TGC ATA CTG      288
His Pro Asp Cys Tyr Asp Gln Arg Glu Pro Gly Asp Trp Cys Ile Leu
 80                  85                  90                  95

AAA CCG GAT GAG AAA TGG ACA AAT AGA GGT TGT TTC TGT TCA TCC AAG      336
Lys Pro Asp Glu Lys Trp Thr Asn Arg Gly Cys Phe Cys Ser Ser Lys
                100                 105                 110

GGA GAA TGC ACT ATC GAA CGC CAG AAG GGT GAC GGT TTC GAG CAT ACG      384
Gly Glu Cys Thr Ile Glu Arg Gln Lys Gly Asp Gly Phe Glu His Thr
             115                 120                 125

TAC TGC TCA CCT GAC GAA AAC TGG ACC TGC AAA TAT GAT T AATAATTTTA    434
Tyr Cys Ser Pro Asp Glu Asn Trp Thr Cys Lys Tyr Asp
         130                 135                 140

ATTCAAAAAT TATAATATCT ATTCTTAAGT TATACCTCCC CATTTTAATT CCTTCAATCA    494

GCCAACTTTT AACAATGTTT GTTGTGTGCT CTGATTTTTT TTAAATACAA TCTATCGCAT    554

CAA                                                                  557

(2) INFORMATION FOR SEQ ID NO:9:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:9:

Met Thr Thr Lys Phe Leu Ile Ala Phe Gly Leu Val Ile Leu Leu Ser
 1               5                  10                  15

Ile Pro His Cys Ala Ala Glu Glu Asp Phe Glu Glu Glu Gly Glu Gly
             20                  25                  30

Glu Glu Met Pro Glu Asp Asn Asp Asp Ala Gln Pro Glu Asp Ile Asp
             35                  40                  45

Gly Gly Asp Glu Glu Gly Gly Asn Asp Glu Asn Glu Asp Val Pro Arg
         50                  55                  60

Gly Ser Phe Val Asn Ser Met Gly Thr Lys Lys Gln Cys Lys Glu His
 65                  70                  75                  80

Pro Asp Cys Tyr Asp Gln Arg Glu Pro Gly Asp Trp Cys Ile Leu Lys
                 85                  90                  95

Pro Asp Glu Lys Trp Thr Asn Arg Gly Cys Phe Cys Ser Ser Lys Gly
             100                 105                 110

Glu Cys Thr Ile Glu Arg Gln Lys Gly Asp Gly Phe Glu His Thr Tyr
         115                 120                 125

Cys Ser Pro Asp Glu Asn Trp Thr Cys Lys Tyr Asp
         130                 135                 140
```

-continued (2) INFORMATION FOR SEQ ID NO:10:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
ATGACCACCA AATTTCTAAT AGCTTTTGGA TTAGTGATTC TTCTTTCCAT ACCACATTGT        60

GCAGCAGAAG AAGATTTTGA AGAAGAAGGA GAAGGAGAAG AAATGCCGGA AGATAATGAC       120

GATGCTCAGC CGGAAGATAT TGACGGTGGG GATGAAGAAG GAGGAAATGA TGAAAATGAA       180

GATGTTCCTC GAGGATCATT CGTTAATAGT ATGGGCACAA AGAAACAGTG CAAAGAGCAC       240

CCGGATTGCT ATGATCAACG TGAACCAGGT GATTGGTGCA TACTGAAACC GGATGAGAAA       300

TGGACAAATA GAGGTTGTTT CTGTTCATCC AAGGGAGAAT GCACTATCGA ACGCCAGAAG       360

GGTGACGGTT TCGAGCATAC GTACTGCTCA CCTGACGAAA ACTGGACCTG CAAATATGAT       420
```

(2) INFORMATION FOR SEQ ID NO:11:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..354

(xi) SEQUENCE DESCRIPTION: SEQ ID NO:11:

```
GAA GAA GAT TTT GAA GAA GAA GGA GAA GGA GAA GAA ATG CCG GAA GAT         48
Glu Glu Asp Phe Glu Glu Glu Gly Glu Gly Glu Glu Met Pro Glu Asp
  1               5                  10                  15

AAT GAC GAT GCT CAG CCG GAA GAT ATT GAC GGT GGG GAT GAA GAA GGA         96
Asn Asp Asp Ala Gln Pro Glu Asp Ile Asp Gly Gly Asp Glu Glu Gly
             20                  25                  30

GGA AAT GAT GAA AAT GAA GAT GTT CCT CGA GGA TCA TTC GTT AAT AGT        144
Gly Asn Asp Glu Asn Glu Asp Val Pro Arg Gly Ser Phe Val Asn Ser
         35                  40                  45

ATG GGC ACA AAG AAA CAG TGC AAA GAG CAC CCG GAT TGC TAT GAT CAA        192
Met Gly Thr Lys Lys Gln Cys Lys Glu His Pro Asp Cys Tyr Asp Gln
     50                  55                  60

CGT GAA CCA GGT GAT TGG TGC ATA CTG AAA CCG GAT GAG AAA TGG ACA        240
Arg Glu Pro Gly Asp Trp Cys Ile Leu Lys Pro Asp Glu Lys Trp Thr
 65                  70                  75                  80

AAT AGA GGT TGT TTC TGT TCA TCC AAG GGA GAA TGC ACT ATC GAA CGC        288
Asn Arg Gly Cys Phe Cys Ser Ser Lys Gly Glu Cys Thr Ile Glu Arg
                 85                  90                  95

CAG AAG GGT GAC GGT TTC GAG CAT ACG TAC TGC TCA CCT GAC GAA AAC        336
Gln Lys Gly Asp Gly Phe Glu His Thr Tyr Cys Ser Pro Asp Glu Asn
            100                 105                 110

TGG ACC TGC AAA TAT GAT                                                354
Trp Thr Cys Lys Tyr Asp
        115
```

(2) INFORMATION FOR SEQ ID NO:12:

(i) SEQUENCE CHARACTERISTICS:

-continued

```
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:12:

Glu Glu Asp Phe Glu Glu Gly Gly Glu Glu Met Pro Glu Asp
1               5                   10                  15

Asn Asp Asp Ala Gln Pro Glu Asp Ile Asp Gly Gly Asp Glu Glu Gly
                20                  25                  30

Gly Asn Asp Glu Asn Glu Asp Val Pro Arg Gly Ser Phe Val Asn Ser
            35                  40                  45

Met Gly Thr Lys Lys Gln Cys Lys Glu His Pro Asp Cys Tyr Asp Gln
    50                  55                  60

Arg Glu Pro Gly Asp Trp Cys Ile Leu Lys Pro Asp Glu Lys Trp Thr
65                  70                  75                  80

Asn Arg Gly Cys Phe Cys Ser Ser Lys Gly Glu Cys Thr Ile Glu Arg
                85                  90                  95

Gln Lys Gly Asp Gly Phe Glu His Thr Tyr Cys Ser Pro Asp Glu Asn
                100                 105                 110

Trp Thr Cys Lys Tyr Asp
            115

(2) INFORMATION FOR SEQ ID NO:13:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..66

(xi) SEQUENCE DESCRIPTION: SEQ ID NO:13:

ATG ACC ACC AAA TTT CTA ATA GCT TTT GGA TTA GTG ATT CTT CTT TCC    48
Met Thr Thr Lys Phe Leu Ile Ala Phe Gly Leu Val Ile Leu Leu Ser
1               5                   10                  15

ATA CCA CAT TGT GCA GCA                                             66
Ile Pro His Cys Ala Ala
            20

(2) INFORMATION FOR SEQ ID NO:14:

(i) SEQUENCE CHARACTERISTICS:
            (A) LENGTH: 22 amino acids
            (B) TYPE: amino acid
            (D) TOPOLOGY: linear (ii) MOLECULE TYPE: protein (xi) SEQUENCE DESCRIPTION: SEQ ID NO:14:

Met Thr Thr Lys Phe Leu Ile Ala Phe Gly Leu Val Ile Leu Leu Ser
1               5                   10                  15

Ile Pro His Cys Ala Ala
            20

(2) INFORMATION FOR SEQ ID NO:15:

(i) SEQUENCE CHARACTERISTICS:
```

(A) LENGTH: 242 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

TTGCTATGAT CAACGTGAAC CGCAAGCGTG GTGCATATTA AAGAGGAATC AGTCTTGGAC      60

GTAAGTCTAC GTCTCAGTTA GTTTTATTAT TAAAAAATTG GATAAAAATT ATCAGTGAAT     120

TGAGAACGCT CTGTTATAGA ACAAAGGTT GTTTCTGCGA TGAAAAGAGA CATTTATGCG      180

TTATGGAACG GATGAACGGC GGTAAATTGG AATATGCGTA CTGCTCACCT CACGAAAACT     240

GG                                                                    242

(2) INFORMATION FOR SEQ ID NO:16:

(i) SEQUENCE CHARACTERISTICS:
            (A) LENGTH: 163 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 2..163

(xi) SEQUENCE DESCRIPTION: SEQ ID NO:16:

T TGC TAT GAT CAA CGT GAA CCG CAA GCG TGG TGC ATA TTA AAG AGG           46
  Cys Tyr Asp Gln Arg Glu Pro Gln Ala Trp Cys Ile Leu Lys Arg
  1               5                  10                 15

AAT CAG TCT TGG ACA AAC AAA GGT TGT TTC TGC GAT GAA AAG AGA CAT         94
Asn Gln Ser Trp Thr Asn Lys Gly Cys Phe Cys Asp Glu Lys Arg His
            20                  25                  30

TTA TGC GTT ATG GAA CGG ATG AAC GGC GGT AAA TTG GAA TAT GCG TAC        142
Leu Cys Val Met Glu Arg Met Asn Gly Gly Lys Leu Glu Tyr Ala Tyr
        35                  40                  45

TGC TCA CCT CAC GAA AAC TGG                                            163
Cys Ser Pro His Glu Asn Trp
        50

(2) INFORMATION FOR SEQ ID NO:17:

(i) SEQUENCE CHARACTERISTICS:
            (A) LENGTH: 54 amino acids
            (B) TYPE: amino acid
            (D) TOPOLOGY: linear (ii) MOLECULE TYPE: protein (xi) SEQUENCE DESCRIPTION: SEQ ID NO:17:

Cys Tyr Asp Gln Arg Glu Pro Gln Ala Trp Cys Ile Leu Lys Arg Asn
1               5                  10                  15

Gln Ser Trp Thr Asn Lys Gly Cys Phe Cys Asp Glu Lys Arg His Leu
            20                  25                  30

Cys Val Met Glu Arg Met Asn Gly Gly Lys Leu Glu Tyr Ala Tyr Cys
        35                  40                  45

Ser Pro His Glu Asn Trp
        50

(2) INFORMATION FOR SEQ ID NO:18:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
TTGCTATGAT CAACGTGAAC CACAAGCATG GTGCATGTTG AATGTGAATC AATCATGGAC     60

GTATGGACAT TTTAATTATC TTTGTGAAAA TAGTTTTTCG ATATACATTA GAATCTTCAT    120

TCTTTGTGTT TGTTTTCTAT TTTCTTTTTC AGAGACAAGG GTTGCTTTTG CGATGCTAAT    180

TTGCATTCAT GCGTTATCGA AAGAAAGAAC AATGGTAGGC TGGAATACTC GTACTGCTCA    240

CCCGACGAAA ACTGG                                                    255
```

(2) INFORMATION FOR SEQ ID NO:19:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..163

(xi) SEQUENCE DESCRIPTION: SEQ ID NO:19:

```
T TGC TAT GAT CAA CGT GAA CCA CAA GCA TGG TGC ATG TTG AAT GTG      46
  Cys Tyr Asp Gln Arg Glu Pro Gln Ala Trp Cys Met Leu Asn Val
  1               5                  10                  15

AAT CAA TCA TGG ACA GAC AAG GGT TGC TTT TGC GAT GCT AAT TTG CAT    94
Asn Gln Ser Trp Thr Asp Lys Gly Cys Phe Cys Asp Ala Asn Leu His
            20                  25                  30

TCA TGC GTT ATC GAA AGA AAG AAC AAT GGT AGG CTG GAA TAC TCG TAC   142
Ser Cys Val Ile Glu Arg Lys Asn Asn Gly Arg Leu Glu Tyr Ser Tyr
                35                  40                  45

TGC TCA CCC GAC GAA AAC TGG                                        163
Cys Ser Pro Asp Glu Asn Trp
        50
```

(2) INFORMATION FOR SEQ ID NO:20:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO:20:

```
Cys Tyr Asp Gln Arg Glu Pro Gln Ala Trp Cys Met Leu Asn Val Asn
1               5                  10                  15

Gln Ser Trp Thr Asp Lys Gly Cys Phe Cys Asp Ala Asn Leu His Ser
            20                  25                  30

Cys Val Ile Glu Arg Lys Asn Asn Gly Arg Leu Glu Tyr Ser Tyr Cys
        35                  40                  45

Ser Pro Asp Glu Asn Trp
        50
```

(2) INFORMATION FOR SEQ ID NO:21:

```
        (i) SEQUENCE CHARACTERISTICS:
            (A) LENGTH: 16 amino acids
            (B) TYPE: amino acid
            (D) TOPOLOGY: linear (ii) MOLECULE TYPE: protein (xi) SEQUENCE DESCRIPTION: SEQ ID NO:21:

Met Ala Gln Asp Ala Phe Pro Asn Ala Cys Ala Gln Gly Glu Pro Lys
1               5                  10                  15

(2) INFORMATION FOR SEQ ID NO:22:

(i) SEQUENCE CHARACTERISTICS:
            (A) LENGTH: 16 amino acids
            (B) TYPE: amino acid
            (D) TOPOLOGY: linear (ii) MOLECULE TYPE: protein (ix) FEATURE:
            (A) NAME/KEY: Xaa = Asp or Pro
            (B) LOCATION: 4

(ix) FEATURE:
            (A) NAME/KEY: Xaa = Ala or Gly
            (B) LOCATION: 5

(ix) FEATURE:
            (A) NAME/KEY: Xaa = Phe or Glu
            (B) LOCATION: 6

(ix) FEATURE:
            (A) NAME/KEY: Xaa = Pro or Arg
            (B) LOCATION: 7

(ix) FEATURE:
            (A) NAME/KEY: Xaa = Asn or Lys
            (B) LOCATION: 8

(ix) FEATURE:
            (A) NAME/KEY: Xaa = Cys or Gly
            (B) LOCATION: 10

(xi) SEQUENCE DESCRIPTION: SEQ ID NO:22:

Met Ala Gln Xaa Xaa Xaa Xaa Xaa Ala Xaa Ala Gln Gly Glu Pro Lys
1               5                  10                  15

(2) INFORMATION FOR SEQ ID NO:23:

(i) SEQUENCE CHARACTERISTICS:
            (A) LENGTH: 22 amino acids
            (B) TYPE: amino acid
            (D) TOPOLOGY: linear (ii) MOLECULE TYPE: protein (xi) SEQUENCE DESCRIPTION: SEQ ID NO:23:

Ala Ile Ala Pro Cys Gln Leu Thr Ala Val Gln Ser Val Leu Pro Cys
1               5                  10                  15

Ala Asp Gln Cys Gln Lys
                20

(2) INFORMATION FOR SEQ ID NO:24:

(i) SEQUENCE CHARACTERISTICS:
            (A) LENGTH: 22 amino acids
            (B) TYPE: amino acid
            (D) TOPOLOGY: linear (ii) MOLECULE TYPE: protein
```

(xi) SEQUENCE DESCRIPTION: SEQ ID NO:24:

Leu Gly Ser Cys Ser Pro Asp Cys Gly Leu Asp Leu Pro Ser Asp Asn
1               5                   10                  15

Val Met Val Gln Asp Val
            20

(2) INFORMATION FOR SEQ ID NO:25:

(i) SEQUENCE CHARACTERISTICS:
        (A) LENGTH: 22 amino acids
        (B) TYPE: amino acid
        (D) TOPOLOGY: linear (ii) MOLECULE TYPE: protein (ix) FEATURE:
        (A) NAME/KEY: Xaa = Gly or Met
        (B) LOCATION: 2

(ix) FEATURE:
        (A) NAME/KEY: Xaa = Cys or Val
        (B) LOCATION: 4

(ix) FEATURE:
        (A) NAME/KEY: Xaa = Ser or Asp
        (B) LOCATION: 5

(ix) FEATURE:
        (A) NAME/KEY: Xaa = Pro or Arg
        (B) LOCATION: 6

(ix) FEATURE:
        (A) NAME/KEY: Xaa = Asp or Trp
        (B) LOCATION: 11

(ix) FEATURE:
        (A) NAME/KEY: Xaa = Lys or Trp
        (B) LOCATION: 12

(ix) FEATURE:
        (A) NAME/KEY: Xaa = Pro or Arg
        (B) LOCATION: 13

(ix) FEATURE:
        (A) NAME/KEY: Xaa = Asp or Trp
        (B) LOCATION: 15

(ix) FEATURE:
        (A) NAME/KEY: Xaa = Met or Trp
        (B) LOCATION: 18

(ix) FEATURE:
        (A) NAME/KEY: Xaa = Val or Ser
        (B) LOCATION: 19

(ix) FEATURE:
        (A) NAME/KEY: Xaa = Asp, Gln or Trp
        (B) LOCATION: 21

(ix) FEATURE:
        (A) NAME/KEY: Xaa = Val or Ser
        (B) LOCATION: 22

(xi) SEQUENCE DESCRIPTION: SEQ ID NO:25:

Leu Xaa Ser Xaa Xaa Xaa Asp Cys Gly Leu Xaa Xaa Xaa Ser Xaa Asn
1               5                   10                  15

Val Xaa Xaa Gln Xaa Xaa
            20

(2) INFORMATION FOR SEQ ID NO:26:

(i) SEQUENCE CHARACTERISTICS:

(A) LENGTH: 12 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:26:

His Val Glu Thr His Glu Ala Cys Tyr Asp Gln Arg
1               5                   10

(2) INFORMATION FOR SEQ ID NO:27:

(i) SEQUENCE CHARACTERISTICS:
            (A) LENGTH: 12 amino acids
            (B) TYPE: amino acid
            (D) TOPOLOGY: linear (ii) MOLECULE TYPE: protein (ix) FEATURE:
            (A) NAME/KEY: Xaa = His or Met
            (B) LOCATION: 1

(ix) FEATURE:
            (A) NAME/KEY: Xaa = Glu or Gly
            (B) LOCATION: 3

(ix) FEATURE:
            (A) NAME/KEY: Xaa = Trp or Ser
            (B) LOCATION: 4

(ix) FEATURE:
            (A) NAME/KEY: Xaa = His or Ile
            (B) LOCATION: 5

(ix) FEATURE:
            (A) NAME/KEY: Xaa = Glu or Gly
            (B) LOCATION: 6

(ix) FEATURE:
            (A) NAME/KEY: Xaa = Cys or Met
            (B) LOCATION: 8

(xi) SEQUENCE DESCRIPTION: SEQ ID NO:27:

Xaa Val Xaa Xaa Xaa Xaa Ala Xaa Tyr Asp Gln Arg
1               5                   10

(2) INFORMATION FOR SEQ ID NO:28:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:28:

Gly Glu Phe Val Glu Ser Asp Gly Lys
1               5

(2) INFORMATION FOR SEQ ID NO:29:

(i) SEQUENCE CHARACTERISTICS:
            (A) LENGTH: 8 amino acids
            (B) TYPE: amino acid
            (D) TOPOLOGY: linear (ii) MOLECULE TYPE: protein (ix) FEATURE:
            (A) NAME/KEY: Xaa = any amino acid
            (B) LOCATION: 2

(xi) SEQUENCE DESCRIPTION: SEQ ID NO:29:

Asn Xaa Trp Gln Cys Ser Tyr Asp
1               5

(2) INFORMATION FOR SEQ ID NO:30:

(i) SEQUENCE CHARACTERISTICS:
        (A) LENGTH: 17 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 14

(xi) SEQUENCE DESCRIPTION: SEQ ID NO:30:

Glu Pro Gln Ser Trp Cys Ile Leu Lys Pro His Gln Ser Xaa Thr Gln
1               5                   10                  15

Arg (2) INFORMATION FOR SEQ ID NO:31:

(i) SEQUENCE CHARACTERISTICS:
        (A) LENGTH: 17 amino acids
        (B) TYPE: amino acid
        (D) TOPOLOGY: linear (ii) MOLECULE TYPE: protein (ix) FEATURE:
        (A) NAME/KEY: Xaa = Trp or Ala
        (B) LOCATION: 5

(ix) FEATURE:
        (A) NAME/KEY: Xaa = any amino acid
        (B) LOCATION: 14

(ix) FEATURE:
        (A) NAME/KEY: Xaa = Thr or Trp
        (B) LOCATION: 15

(ix) FEATURE:
        (A) NAME/KEY: Xaa = Gln or Asp
        (B) LOCATION: 16

(xi) SEQUENCE DESCRIPTION: SEQ ID NO:31:

Glu Pro Gln Ser Xaa Cys Ile Leu Lys Pro His Gln Ser Xaa Xaa Xaa
1               5                   10                  15

Arg (2) INFORMATION FOR SEQ ID NO:32:

(i) SEQUENCE CHARACTERISTICS:
        (A) LENGTH: 15 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 8

(ix) FEATURE:
        (A) NAME/KEY: Xaa = any amino acid
        (B) LOCATION: 12

(ix) FEATURE:

(A) NAME/KEY: Xaa = any amino acid
            (B) LOCATION: 14

(xi) SEQUENCE DESCRIPTION: SEQ ID NO:32:

Glu Thr Gln Glu Glu Thr Val Xaa Phe Glu Glu Xaa Asp Xaa Asp
1               5                   10                  15

(2) INFORMATION FOR SEQ ID NO:33:

(i) SEQUENCE CHARACTERISTICS:
            (A) LENGTH: 15 amino acids
            (B) TYPE: amino acid
            (D) TOPOLOGY: linear (ii) MOLECULE TYPE: protein (ix) FEATURE:
            (A) NAME/KEY: Xaa = Glu or Pro
            (B) LOCATION: 1

(ix) FEATURE:
            (A) NAME/KEY: Xaa = any amino acid
            (B) LOCATION: 8

(ix) FEATURE:
            (A) NAME/KEY: Xaa = any amino acid
            (B) LOCATION: 12

(ix) FEATURE:
            (A) NAME/KEY: Xaa = any amino acid
            (B) LOCATION: 14

(xi) SEQUENCE DESCRIPTION: SEQ ID NO:33:

Xaa Thr Gln Glu Glu Thr Val Xaa Phe Glu Glu Xaa Asp Xaa Asp
1               5                   10                  15

(2) INFORMATION FOR SEQ ID NO:34:

(i) SEQUENCE CHARACTERISTICS:
            (A) LENGTH: 7 amino acids
            (B) TYPE: amino acid
            (D) TOPOLOGY: linear (ii) MOLECULE TYPE: protein (xi) SEQUENCE DESCRIPTION: SEQ ID NO:34:

Phe Val Glu Ser Asp Gly Lys
1               5

(2) INFORMATION FOR SEQ ID NO:35:

(i) SEQUENCE CHARACTERISTICS:
            (A) LENGTH: 9 amino acids
            (B) TYPE: amino acid
            (D) TOPOLOGY: linear (ii) MOLECULE TYPE: protein (ix) FEATURE:
            (A) NAME/KEY: Xaa = any amino acid
            (B) LOCATION: 2

(xi) SEQUENCE DESCRIPTION: SEQ ID NO:35:

Thr Xaa Glu Ala Cys Tyr Asp Gln Arg
1               5

(2) INFORMATION FOR SEQ ID NO:36:

(i) SEQUENCE CHARACTERISTICS:
            (A) LENGTH: 8 amino acids
            (B) TYPE: amino acid

```
         (D) TOPOLOGY: linear (ii) MOLECULE TYPE: protein (xi) SEQUENCE DESCRIPTION: SEQ ID NO:36:

Phe Asn Trp Gln Cys Ser Tyr Asp
1               5

(2) INFORMATION FOR SEQ ID NO:37:

(i) SEQUENCE CHARACTERISTICS:
        (A) LENGTH: 8 amino acids
        (B) TYPE: amino acid
        (D) TOPOLOGY: linear (ii) MOLECULE TYPE: protein (ix) FEATURE:
        (A) NAME/KEY: Xaa = Asn or Met
        (B) LOCATION: 2

(ix) FEATURE:
        (A) NAME/KEY: Xaa = Trp or Leu
        (B) LOCATION: 3

(xi) SEQUENCE DESCRIPTION: SEQ ID NO:37:

Phe Xaa Xaa Gln Cys Ser Tyr Asp
1               5

(2) INFORMATION FOR SEQ ID NO:38:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:38:

Glu Ala Cys Tyr Asp Gln
1               5

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: probe (ix) FEATURE:
        (A) NAME/KEY: N=INOSINE
        (B) LOCATION: 6

(xi) SEQUENCE DESCRIPTION: SEQ ID NO:39:

GAAGCNTGCT ATGATCAA                                          18

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: probe (xi) SEQUENCE DESCRIPTION: SEQ ID NO:40:
```

```
CATAGTTCTT GGCTTAGCGC TTC                                          23

(2) INFORMATION FOR SEQ ID NO:41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:41:

CGCGGATCCT TCCGCATCAG AATCACAAGA AG                                32

(2) INFORMATION FOR SEQ ID NO:42:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:42:

CGAAGGAATG GATCCTTATA AGTTATTAAT CG                                32

(2) INFORMATION FOR SEQ ID NO:43:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:43:

GCGGGATCCA ACATGAACAA ACTTTTCATA GTTC                              34

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:44:

CGAGCTCGGA TCCACTAG                                                18

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:45:

GCATGCTCGA GCGGCCGC                                                18

(2) INFORMATION FOR SEQ ID NO:46:
```

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:46:

CGCTCTAGAA CTAGTGGATC                                                   20

(2) INFORMATION FOR SEQ ID NO:47:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:47:

GTGCATTCTC CCTTGGATGA ACAG                                              24

(2) INFORMATION FOR SEQ ID NO:48:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:48:

CGCGGATCCT ATAAATATGA CCACCAAATT TCTAATAGC                              39

(2) INFORMATION FOR SEQ ID NO:49:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:49:

GCTCTAGATA TTAATCATAT TTGCAGGTCC AG                                     32

(2) INFORMATION FOR SEQ ID NO:50:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:50:

GAATTCGGAT CCAGGCCACC ATGAACAAAC TTTTCATAG                              39

(2) INFORMATION FOR SEQ ID NO:51:

(i) SEQUENCE CHARACTERISTICS:
            (A) LENGTH: 40 base pairs
            (B) TYPE: nucleic acid

```
            (C) STRANDEDNESS: single
            (D) TOPOLOGY: linear (ii) MOLECULE TYPE: primer (xi) SEQUENCE DESCRIPTION: SEQ ID NO:51:

GAATTGGATC CGCCACCATG ACCACCAAAT TTCTAATAGC                              40

(2) INFORMATION FOR SEQ ID NO:52:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:52:

TTTTGGATCC AAATTATTAA TCATATTTGC                                        30

(2) INFORMATION FOR SEQ ID NO:53:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:53:

TTGCTATGAT CAACGTGAAC C                                                 21

(2) INFORMATION FOR SEQ ID NO:54:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:54:

CCAGTTTTYK YSRGGTGAGC ARTACG                                            26

(2) INFORMATION FOR SEQ ID NO:55:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: probe (xi) SEQUENCE DESCRIPTION: SEQ ID NO:55:

ATGGACAMAW AGAGGTTGTT TCTG                                              24
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule selected from the group consisting of: (a) a nucleic acid molecule comprising a nucleic acid sequence selected from the group consisting of SEQ ID NO:1, SEQ ID NO:3, SEQ ID NO:4, SEQ ID NO:6, SEQ ID NO:8, SEQ ID NO:10, SEQ ID NO:11, SEQ ID NO:13, SEQ ID NO:15, SEQ ID NO:16, SEQ ID NO:18, and SEQ ID NO:19; (b) a nucleic acid molecule comprising a homologue of a nucleic acid molecule comprising a nucleic acid sequence selected from the group consisting of SEQ ID NO:1, SEQ ID NO:3, SEQ ID NO:4, SEQ ID NO:6, wherein said nucleic acid homologue encodes a protein containing one or more amino acid deletions, substitutions, or insertions, wherein said protein encoded by said homologue comprises at least one epitope comprising at least 5 contiguous amino acids that elicits an immune response against a protein comprising an amino acid sequence selected from the group consisting of SEQ ID NO:2, SEQ ID NO:5 and SEQ ID NO:7, wherein said homologue has at least a 15 contiguous nucleic acid portion identical in sequence to a contiguous 15 nucleic acid portion of sequence selected from the group consisting of SEQ ID NO:1, SEQ ID NO:3, SEQ ID NO:4, SEQ ID NO:6, wherein said homologue is of a *D. immitis* nucleic acid molecule; and (c) a nucleic acid molecule that is fully complementary to any of said nucleic acid molecules of (a) or (b).

2. The nucleic acid molecule of claim 1, wherein said nucleic acid molecule comprises a nucleic acid molecule selected from the group consisting of $nDiPLA2_{586}$ (characterized by a coding strand having the nucleic acid sequence of SEQ ID NO:1), $nDiPLA2_{450}$ (characterized by a coding strand having the nucleic acid sequence of SEQ ID NO:3), $nDiPLA2_{387}$ (characterized by a coding strand having the nucleic acid sequence of SEQ ID NO:4), $nDiPLA2_{63}$ (characterized by a coding strand having the nucleic acid sequence of SEQ ID NO:6), $nDiPLA2_{475}$ (characterized by a coding strand having the nucleic acid sequence of nucleotides 1–475 of SEQ ID NO:1), $nDiPLA2_{463}$ (characterized by a coding strand having the nucleic acid sequence of nucleotides 7–469 of SEQ ID NO:1), $nDiPLA2_{417}$ (characterized by a coding strand having the nucleic acid sequence of nucleotides 58–474 of SEQ ID NO:1), $nOvPLA2_{557}$ (characterized by a coding strand having the nucleic acid sequence of SEQ ID NO:8), $nOvPLA2_{420}$ (characterized by a coding strand having the nucleic acid sequence of SEQ ID NO:10), $nOvPLA2_{354}$ (characterized by a coding strand having the nucleic acid sequence of SEQ ID NO:11), $nOvPLA2_{66}$ (characterized by a coding strand having the nucleic acid sequence of SEQ ID NO:13), $nOvPLA2_{542}$ (characterized by a coding strand having the nucleic acid sequence of nucleotides 16–557 of SEQ ID NO:8), $nOvPLA2_{496}$ (characterized by a coding strand having the nucleic acid sequence of nucleotides 62–557 of SEQ ID NO:8), $nOvPLA2_{430}$ (characterized by a coding strand having the nucleic acid sequence of nucleotides 4–433 of SEQ ID NO:8), $nOvPLA2_{425}$ (characterized by a coding strand having the nucleic acid sequence of nucleotides 4–428 of SEQ ID NO:8), $nOvPLA2_{158}$ (characterized by a coding strand having the nucleic acid sequence of nucleotides 262–419 of SEQ ID NO:8), $nBmPLA2(19)_{242}$ (characterized by a coding strand having the nucleic acid sequence of SEQ ID NO:15), $nBmPLA2(19)_{163}$ (characterized by a coding strand having the nucleic acid sequence of SEQ ID NO:16), $nBmPLA2(25)_{255}$ (characterized by a coding strand having the nucleic acid sequence of SEQ ID NO:18), and $nBmPLA2(25)_{163}$ (characterized by a coding strand having the nucleic acid sequence of SEQ ID NO:19).

3. The nucleic acid molecule of claim 1, wherein said nucleic acid molecule is selected from the group consisting of (a) a nucleic acid molecule comprising nucleic acid sequence SEQ ID NO:1, a nucleic acid molecule comprising nucleic acid sequence SEQ ID NO:3, a nucleic acid molecule comprising nucleic acid sequence SEQ ID NO:4, a nucleic acid molecule comprising nucleic acid sequence SEQ ID NO:6, a nucleic acid molecule comprising nucleic acid sequence SEQ ID NO:8, a nucleic acid molecule comprising nucleic acid sequence SEQ ID NO:10, a nucleic acid molecule comprising nucleic acid sequence SEQ ID NO:11, a nucleic acid molecule comprising nucleic acid sequence SEQ ID NO:13, a nucleic acid molecule comprising nucleic acid sequence SEQ ID NO:15, a nucleic acid molecule comprising nucleic acid sequence SEQ ID NO:16, a nucleic acid molecule comprising nucleic acid sequence SEQ ID NO:18, a nucleic acid molecule comprising nucleic acid sequence SEQ ID NO:19, and (b) a nucleic acid molecule that is fully complementary to any of said nucleic acid molecules of (a).

4. The nucleic acid molecule of claim 1, wherein said nucleic acid molecule encodes a protein that selectively binds to immune serum derived from an animal that is immune to infection by *Dirofilaria immitis*.

5. The nucleic acid molecule of claim 4, wherein said immune serum is derived from an animal immunized with a composition comprising *Dirofilaria immitis* larvae selected from the group consisting of third stage larvae, fourth stage larvae, and mixtures thereof.

6. A recombinant molecule comprising a nucleic acid molecule as set forth in claim 1 operatively linked to a transcription control sequence.

7. A recombinant virus comprising a recombinant molecule as set forth in claim 6.

8. An isolated recombinant cell comprising a nucleic acid molecule as set forth in claim 1, said cell being capable of expressing said nucleic acid molecule.

9. The nucleic acid molecule of claim 1, wherein said nucleic acid molecule is selected from the group consisting of: (a) a nucleic acid molecule that encodes a protein comprising an amino acid sequence selected from the group consisting of SEQ ID NO:2, SEQ ID NO:5, SEQ ID NO:7, SEQ ID NO:9, SEQ ID NO:12, SEQ ID NO:14, SEQ ID NO:17, and SEQ ID NO:20; and (b) a nucleic acid molecule comprising a homologue of a nucleic acid molecule comprising a nucleic acid sequence that encodes a protein comprising an amino acid sequence selected from the group consisting of SEQ ID NO:2, SEQ ID NO:5 and SEQ ID NO:7; wherein said nucleic acid homologue encodes a protein containing one or more amino acid deletions, substitutions, or insertions, wherein said protein encoded by said homologue comprises at least one epitope comprising at least 5 contiguous amino acids that elicits an immune response against a protein comprising an amino acid sequence selected from the group consisting of SEQ ID NO:2, SEQ ID NO:5 and SEQ ID NO:7, wherein said homologue has at least a 15 contiguous nucleic acid portion identical in sequence to a contiguous 15 nucleic acid portion of sequence selected from the group consisting of SEQ ID NO:1, SEQ ID NO:3, SEQ ID NO:4, SEQ ID NO:6, and wherein said homologue is of a *D. immitis* nucleic acid molecule.

10. A method to produce a protein, said method comprising culturing an isolated cell capable of expressing said protein, said protein being encoded by an isolated nucleic acid molecule, as claimed in claim 1.

* * * * *